US006521412B1

(12) United States Patent
Yang et al.

(10) Patent No.: US 6,521,412 B1
(45) Date of Patent: Feb. 18, 2003

(54) **HSREQ\*1 AND HSREQ\*2PROTEINS AND USE THEREOF TO DETECT CDK2**

(75) Inventors: Meijia Yang, East Lyme, CT (US); Krishnan Nandabalan, Guilford, CT (US); Vincent Peter Schulz, Madison, CT (US)

(73) Assignee: CuraGen Corporation, New Haven, CT (US)

( * ) Notice: Subject to any disclaimer, the term of this patent is extended or adjusted under 35 U.S.C. 154(b) by 0 days.

(21) Appl. No.: 09/338,125

(22) Filed: Jun. 22, 1999

Related U.S. Application Data

(62) Division of application No. 08/969,106, filed on Nov. 13, 1997, now Pat. No. 5,986,055.

(51) Int. Cl.$^7$ .............................. C12Q 1/02; C12Q 1/68; G01N 33/53; C07K 14/00; C07K 5/00

(52) U.S. Cl. ............................ 435/7.1; 435/6; 435/29; 530/300; 530/350; 514/2; 514/12

(58) Field of Search ................... 514/2, 12; 530/300, 530/350; 435/6, 29, 7.1

(56) References Cited

FOREIGN PATENT DOCUMENTS

| EP | 0 863 204 A | 9/1998 |
|---|---|---|
| WO | WO 97/11176 | 3/1997 |
| WO | WO 97/12973 | 4/1997 |
| WO | WO 97/25345 | 7/1997 |
| WO | WO 97/27297 | 7/1997 |

OTHER PUBLICATIONS

Adams et al., 1996, "Identification of a cyclin–cdk2 recognition motif present in substrates and p21–like cyclin–dependent kinase inhibitors", Mol. Cell. Biol. 16:6623–6633.
Amundadittir et al., 1996, "Transgenic mouse models of breast cancer", Breast Cancer Res. Treat. 39:119–135.
Applebaum, 1997, "Graft versus leukemia (GVL) in the therapy of acute lymphoblastic leukemia (All)", Leukemia 11 (Supp4):S15–S17.
Callow, 1995, "Molecular biology of graft occlusion", Curr. Opin. Cardiol. 10:569–576.
Carlson et al., 1996, "Flavopiridol induces G$_1$ arrest with inhibition of cyclin–dependent kinase (CDK) 2 and CDK4 in human breast carcinoma cells", Cancer Res. 56:2973–2978.
Chen et al., 1997, "Downregulation of cyclin–dependent kinase 2 activity and cyclin A promoter AF activity in vascular smooth muscle cells by p27$^{KIP1}$, an inhibitor of neointima formation in the rat carotid artery", J. Clin. Invest. 99:2334–2341.
Dankort and Muller, 1996, "Transgenic models of breast cancer metastasis", Cancer Treat. Res. 83:71–88.
Donehower, 1996, The p53–deficient mouse: a model for basic and applied cancer studies, Semin. Cancer. Biol. 7:269–278.

Drapkin et al., 1996, "Human cyclin–dependent kinase–activating kinase exists in three distinct complexes", Proc. Nati. Acad. Sd. USA 93:6488–6493.
Ellege and Spottswood, 1991, "A new human p34 protein kinase, CDK2, identified by complementation of a cdc28 mutation in *Saccharomyces cerevisiae*, is a homolog of Xenopus Eg 1", EMBO J. 10:2653–2659.
Farber et al., 1992, "Cytokine secretion by human aortic endothelial cells is related to degree of atherosclerosis", Am. J. Physiol. 262:H 1088–1085.
Farine, 1997, "Animal models in autoimmune disease in immunotoxicity assessment", Toxicol. 199:29–35.
Fisher and Morgan, 1994, "A novel cyclin associated with MO1S/CDK7 to form the CDK–activating kinase", Cell 78:713–724.
Frey, 1997, "Study of immune response to tumors in the rat", Methods 12:173–188.
Frostegard et al., 1996, "Induction of heat shock protein in monocyte cells by oxidized low density lipoprotein", Atherosclerosis 121:93–103.
Gabig et al., 1994, "Requiem: a novel zinc finger gene essential for apoptosis in myeloid cells", J. Biol. Chem. 269:29515–29519.
Elledge and Spottswood, (1992) "A new human p34 protein kinase, CDK2, identified by complementation of a cdc28 mutation in *Saccharomyces cerevisiae*, is a homolog of Xenopus Eg1." *EMBO J.* 10(9): 2653–2659, Accession No. X61622, Jan. 15, 1992.
Ohnishi, (1996) "Direct Submission." *GenBank,* Accession No. D85785, Feb. 6, 1999.
Nakamura, (1995) "Direct Submission." *GenBank,* Accession No. D50310, Feb. 10, 1999.
Gabig, et al., (1994) "Requiem: a novel zinc finger gene essential for apoptosis in myeloid cells." *J. Biol. Chem.* 269(47): 29515–29519, Accession No. U94585, May 27, 1997.
Makela, et al.. (1994) "A cyclin associated with the CDK–activating kinase MO15." *Nature* 371:254–257, Accession No. U11791, Sep. 8, 1994.

(List continued on next page.)

*Primary Examiner*—David Guzo
*Assistant Examiner*—Gerald G. Leffers, Jr.
(74) *Attorney, Agent, or Firm*—Mintz, Levin, Cohn, Ferris, Glovsky and Popeo, P.C.; Ivor R. Elrifi, Esq.

(57) ABSTRACT

The present invention relates to complexes of the CDK2 protein with proteins identified as interacting with CDK2 by a modified yeast two hybrid assay system. The proteins identified to interact with CDK2 are cyclin H, cyclin I, ERH, and two gene products, hsReq*-1 and hsReq*-2, which are splice variants of the gene hsReq. Thus, the invention provides complexes of CDK2 and cyclin H, cyclin I, ERH, hsReq*-1, and hsReq*-2, and derivatives, fragments and analogs thereof. The invention also provides nucleic acids encoding the hsReq*-1 and hsReq*-2, and proteins and derivatives, fragments and analogs thereof. Methods of screening the complexes for efficacy in treating and/or preventing certain diseases and disorders, particularly cancer, atherosclerosis and neurodegenerative disease are also provided.

14 Claims, 16 Drawing Sheets

OTHER PUBLICATIONS

Figure 8:
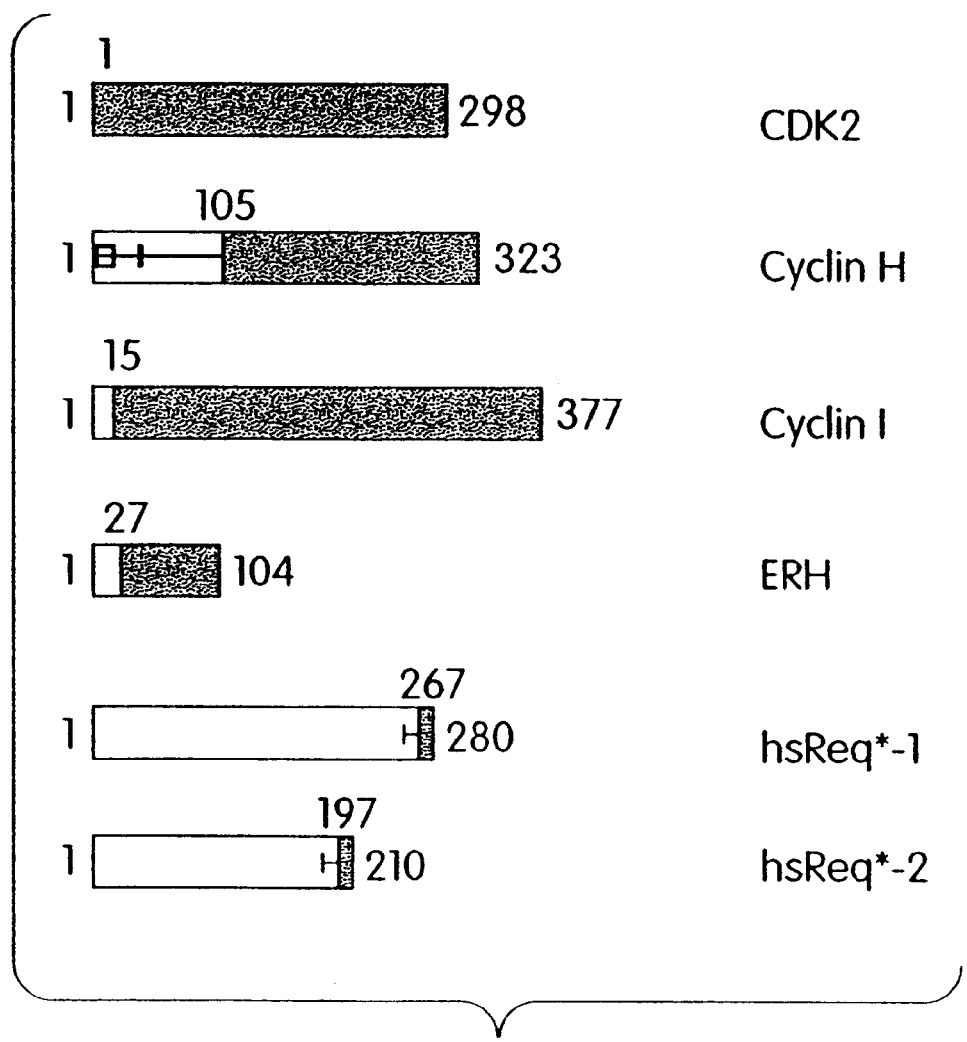

Gibson et al., 1994, "Evidence for a protein domain superfamily shared by the cyclins, TFIIB and RB/p107", Nucl. Acids Res. 22:946–952.

Gutman and Fidler, 1995, "Biology of human colon cancer metastasis", World J. Surg. 19:226–234.

Higashi et al., 1996, "Cyclin–dependent kinase-2 (Cdk2) forms an active complex with cyclin DI since Cdk2 associated with cyclin DI is not phosphorylated by Cdk7–cyclin–H", Eur. J. Biochem. 237:460–467.

Holtzman et al., 1996, "Developmental abnormalities and age–related neurodegeneration in a mouse model of Down syndrome", Proc. Natl. Acad. Sci. USA 93:13333–13338.

Hung et al., 1992, "Increased expression of beta–amyloid precursor protein during neuronal differentiation is not accompanied by secretory cleavage", Proc. Natl. Acad. Sci. USA 89:9439–9443.

Isselbacher et al., "Principals of Neoplasia" Harrison's Principals of Internal Medicine, 13th Edition (McGraw Hill, New York) p. 1814.

Jarrett et al., 1995, "Model of human transitional cell carcinoma: tumor xenografts in upper urinary of nude rat", J. Endurol. 9:1–7.

Johnson–Wood et al., 1997, "Amyloid precursor protein processing and A beta42 deposition in a transgenic mouse model of Alzheimer disease", Proc. Natl. Acad. Sci. USA 94:1550–1 555.

Kappel et al., 1994, "Evolving concepts in molecular patholgy", FASEB J. 8:583–592.

Katz et al., 1994, "Serotonin–stimulated aortic endothelial cells secrete a novel T lymphocyte chemotactic and growth factor", J. leukoc. Biol. 55:567–573.

Kokunai et al., 1997, "Induction of differentiation by wild–type p53 gene in a human glioma cell", J. Neuro–oncol. 32:125–133.

Kurabayashi and Yazaki, 1996, "Molecular genetic approach to the pathophysiology of cardiovascular disease", Int. Angiol. 15:187–1 94.

Libby et al., 1996, "Macrophages and atherosclerotic plaque stability", Curr. Opin. Lipidol. 7:330–335.

Lovejoy et al., 1997, "Animal models and the molecular pathology of cancer", J. Pathol. 181:130–135.

Makela et al., 1994, "A cyclin associated with the CDK–activating kinase MOI 5", Nature 371:254–257.

Maneiro et al., 1997, "An experimental model to study the cytotoxic effects induced by fi–amyloid, histamine, LPS and serum from Alzheimer patients on cultured rat endothelial cells", Methods Find. Exp. din. Pharmacol. 19:5–12.

Mendelsohn, 1992, "Principles of neoplasia" Harrison's Principles of Internal Medicine (McGraw–Hill, Inc., New York) pp. 1814–1826.

Mendelsohn, 1994, "Applications of interaction traps/two–hybrid systems to biotechnology research", Current Biology 5:482–486.

Milne et al., 1994, "Phosphorylation of the tumor suppressor protein p53 by mitogen–activated protein kinases", J. Biol. Chem. 269:9253–9260.

Muir, 1997, "Acetylcholine aging, and Alzheimre's disease", Pharmacol. Biochem. Behav. 56:687–696.

Nakajima et al., 1985, "Dissociated cell culture of cholinergic neurons from nucleus basalis of Meynert and other basal forebrain nuclei", Proc. Natl. Acad. Sci USA 82:6325–6329.

Nakamura et al., 1995, "Cyclin I: a new cyclin encoded by a gene isolated from human brain", Exp. Cell Res. 221:534–542.

Nevisn, 1992, "E2F: a link between the Rb tumor suppressor protein and viral oncoproteins", Science 258:424–429.

Ninomiya–Tsuji et al., 1991, "Cloning of a human cDNA encoding a CDC2–related kinase by complementation of a budding yeast cdc28 mutation", Proc. Natl. Acad. Sci. USA 88:9006–9010.

Oron et al., 1997, "Animal model and in vitro studies of anti neurofilament antibodies mediated neurodegeneration in Alzhemier's disease", J. Neural Transm. Suppl 49:77–84.

Oyasu, 1995, "Epithelial tumours of the lower urinary tract in humans and rodents", Food Chem. Toxicol. 33:747–755.

Padgett et al., 1984, "Splicing of messenger RNA precursors", Ann. Rev. Biochem. 55:1119–1150.

Paigen et al., 1994, "The mouse as a model for human cardiovascular disease and hyperlipidemia", Curr. Opin. Lipidol. 5:258–264.

Polakis, 1997, "The adenomatous polyposis coli (APC) tumor suppressor", Biochem. Biophys. Acta 1 332:F1 27–FI 47.

Poon and Hunter, 1995, "Dephosphorylation of Cdk2 Thri 60 by the cyclin–dependent kinase interacting phosphatase RAP in the absence of cyclin", Science 270:90–93.

Popovic et al., 1996, "Behavioral and adaptive status in an experimental model of Alzheimer's disease in rats", Int. J. Neurosci. 86:281–299.

Rechsteiner, 1990, "Pest sequences are signals for rapid intracellular proteolysis", Semin. Cell. Biol. 1:433–440.

Reed and Maniatis 1988, "The role of the mammalian branchpoint sequence in pre–mRNA splicing", Genes Dev. 2:1268–1276.

Rosenfeld, 1996, "Cellular mechanisms in the development of atherosclerosis", Diabetes Res. Clin. Pract. 30 Suppl.:1–11.

Royai et al., 1996, "Preclinical models of prostate cancer", Semin. Oncol. 23:35–40.

Russo and Russo, 1996, "Experimentally induced mammary tumors in rats", Breast Cancer Res. Treat. 39:7–20.

Seroz et al., 1995, "TFIIH: a link between transcription, DNA repair and cell cycle regulation", Curr. Opin. Genet. Dev. 5:217–222.

Shoemaker et al, 1997, "Studies of neoplasia in the Mm mouse", Biochem. Biophys. Acta 1 332:F25–F48.

Sigal et al., 1994, "Oxidation, lipoxygenase, and atherogenesis", Ann. N.Y. Acad. Sci. 714:211–224.

Suttles et al., 1995, "T cell—vascular smooth muscle cell interactions: antigen–specific activation and cell cycle blockade of T helper clones by cloned vascular smooth muscle cells", Exp. Cell. Res. 218:331–338.

Taylor, 1997, "Transgenic rabbit models for the study of atherosclerosis", Ann. N.Y. Acad. Sci. 811:146–152.

Wang et al., 1997, "Establishment of an experimental intrapulmonary tumor nodule model", Ann. Thorac. Surg. 64:21 6–219.

Warren, 1996, "Cytokines in the cotton top tamarin model of human ulcerative colitis", Aliment. Pharmacol. Ther. 10 (Suppl2) 45–47.

Watts et al, 1995, "Antiestrogen inhibition of cell cycle progression in breast cancer cells is associated with inhibition of cyclin–dependent kinase activity and decreased retinoblastoma protein phosphorylation", Mol. Endocrinol. 9:1804–1813.

Harper, et al., "The p21 Cdk–Interacting protein Cip1 is a potent inhibitor of G1 cyclin–dependent kinases" *Cell* 75:805–816 (1993).

```
ATG GAG AAC TTC CAA AAG GTG GAA AAG ATC GGA GAG GGC ACG TAC GGA  48
Met Glu Asn Phe Gln Lys Val Glu Lys Ile Gly Glu Gly Thr Tyr Gly
 1               5                  10                  15

GTT GTG TAC AAA GCC AGA AAC AAG TTG ACG GGA GAG GTG GTG GCG CTT  96
Val Val Tyr Lys Ala Arg Asn Lys Leu Thr Gly Glu Val Val Ala Leu
                20                  25                  30

AAG AAA ATC CGC CTG GAC ACT GAG ACT GAG GGT GTG CCC AGT ACT GCC 144
Lys Lys Ile Arg Leu Asp Thr Glu Thr Glu Gly Val Pro Ser Thr Ala
                35                  40                  45

ATC CGA GAG ATC TCT CTG CTT AAG GAG CTT AAC CAT CCT AAT ATT GTC 192
Ile Arg Glu Ile Ser Leu Leu Lys Glu Leu Asn His Pro Asn Ile Val
            50                  55                  60

AAG CTG CTG GAT GTC ATT CAC ACA GAA AAT AAA CTC TAC CTG GTT TTT 240
Lys Leu Leu Asp Val Ile His Thr Glu Asn Lys Leu Tyr Leu Val Phe
65                  70                  75                  80

GAA TTT CTG CAC CAA GAT CTC AAG AAA TTC ATG GAT GCC TCT GCT CTC 288
Glu Phe Leu His Gln Asp Leu Lys Lys Phe Met Asp Ala Ser Ala Leu
                85                  90                  95

ACT GGC ATT CCT CTT CCC CTC ATC AAG AGC TAT CTG TTC CAG CTG CTC 336
Thr Gly Ile Pro Leu Pro Leu Ile Lys Ser Tyr Leu Phe Gln Leu Leu
                100                 105                 110

CAG GGC CTA GCT TTC TGC CAT TCT CAT CGG GTC CTC CAC CGA GAC CTT 384
Gln Gly Leu Ala Phe Cys His Ser His Arg Val Leu His Arg Asp Leu
            115                 120                 125

AAA CCT CAG AAT CTG CTT ATT AAC ACA GAG GGG GCC ATC AAG CTA GCA 432
Lys Pro Gln Asn Leu Leu Ile Asn Thr Glu Gly Ala Ile Lys Leu Ala
            130                 135                 140

GAC TTT GGA CTA GCC AGA GCT TTT GGA GTC CCT GTT CGT ACT TAC ACC 480
Asp Phe Gly Leu Ala Arg Ala Phe Gly Val Pro Val Arg Thr Tyr Thr
145                 150                 155                 160

CAT GAG GTG GTG ACC CTG TGG TAC CGA GCT CCT GAA ATC CTC CTG GGC 528
His Glu Val Val Thr Leu Trp Tyr Arg Ala Pro Glu Ile Leu Leu Gly
                165                 170                 175

TCG AAA TAT TAT TCC ACA GCT GTG GAC ATC TGG AGC CTG GGC TGC ATC 576
Ser Lys Tyr Tyr Ser Thr Ala Val Asp Ile Trp Ser Leu Gly Cys Ile
                180                 185                 190

TTT GCT GAG ATG GTG ACT CGC CGG GCC CTG TTC CCT GGA GAT TCT GAG 624
Phe Ala Glu Met Val Thr Arg Arg Ala Leu Phe Pro Gly Asp Ser Glu
                195                 200                 205
```

Fig. 1A

```
ATT GAC CAG CTC TTC CGG ATC TTT CGG ACT CTG GGG ACC CCA GAT GAG 672
Ile Asp Gln Leu Phe Arg Ile Phe Arg Thr Leu Gly Thr Pro Asp Glu
    210             215                 220

GTG GTG TGG CCA GGA GTT ACT TCT ATG CCT GAT TAC AAG CCA AGT TTC 720
Val Val Trp Pro Gly Val Thr Ser Met Pro Asp Tyr Lys Pro Ser Phe
225             230                 235                 240

CCC AAG TGG GCC CGG CAA GAT TTT AGT AAA GTT GTA CCT CCC CTG GAT 768
Pro Lys Trp Ala Arg Gln Asp Phe Ser Lys Val Val Pro Pro Leu Asp
            245                 250                 255

GAA GAT GGA CGG AGC TTG TTA TCG CAA ATG CTG CAC TAC GAC CCT AAC 816
Glu Asp Gly Arg Ser Leu Leu Ser Gln Met Leu His Tyr Asp Pro Asn
        260                 265                 270

AAG CGG ATT TCG GCC AAG GCA GCC CTG GCT CAC CCT TTC TTC CAG GAT 864
Lys Arg Ile Ser Ala Lys Ala Ala Leu Ala His Pro Phe Phe Gln Asp
    275                 280                 285

GTG ACC AAG CCA GTA CCC CAT CTT CGA CTC TGATAGCCTT CTTGAAGCCC CCG 917
Val Thr Lys Pro Val Pro His Leu Arg Leu
    290             295         298

ACCCTAATCG GCTCACCCTC TCCTCCAGTG TGGGCTTGAC CAGCTTGGCC TTGGGCTATT  977

TGGACTCAGG TGGGCCCTCT GAACTTGCCT TAAACACTCA CCTTCTAGTC TTAACCAGCC 1037

AACTCTGGGA ATACAGGGGT GAAAGGGGGG AACCAGTGAA AATGAAAGGA AGTTTCAGTA 1097

TTAGATGCAC TTAAGTTAGC CTCCACCACC CTTTCCCCCT TCTCTTAGTT ATTGCTGAAG 1157

AGGGTTGGTA TAAAAATAAT TTTAAAAAAG CCTTCCTACA CGTTAGATTT GCCGTACCAA 1217

TCTCTGAATG CCCCATAATT ATTATTTCCA GTGTTTGGGA TGACCAGGAT CCCAAGCCTC 1277

CTGCTGCCAC AATGTTTATA AAGGCCAAAT GATAGCGGGG GCTAAGTTGG TGCTTTTGAG 1337

AATTAAGTAA AACAAAACCA CTGGGAGGAG TCTATTTTAA AGAATTCGGT TAAAAAATAG 1397

ATCCAATCAG TTTATACCCT AGTTAGTGTT TTCCTCACCT AATAGGCTGG GAGACTGAAG 1457

ACTCAGCCCG GGTGGGGGT                                             1476
```

Fig. 1B

```
GGACGCTGAT GCGTTTGGGT TCTCGTCTGC AGACCCTCTG GACCTGGTCA CGATTCCATA    60
           ↓          ↓     ↓              ↓   ↓   ↓   ↓
ATG TAC CAC AAC AGT AGT CAG AAG CGG CAC TGG ACC TTC TCC AGC GAG    108
Met Tyr His Asn Ser Ser Gln Lys Arg His Trp Thr Phe Ser Ser Glu
1               5               10              15

GAG CAG CTG GCA AGA CTG CGG GCT GAC GCC AAC CGC AAA TTC AGA TGC    156
Glu Gln Leu Ala Arg Leu Arg Ala Asp Ala Asn Arg Lys Phe Arg Cys
            20              25              30
        ↓   ↓
AAA GCC GTG GCC AAC GGG AAG GTT CTT CCG AAT GAT CCA GTC TTT CTT    204
Lys Ala Val Ala Asn Gly Lys Val Leu Pro Asn Asp Pro Val Phe Leu
        35              40              45

GAG CCT CAT GAA GAA ATG ACA CTC TGC AAA TAC TAT GAG AAA AGG TTA    252
Glu Pro His Glu Glu Met Thr Leu Cys Lys Tyr Tyr Glu Lys Arg Leu
50              55              60

TTG GAA TTC TGT TCG GTG TTT AAG CCA GCA ATG CCA AGA TCT GTT GTG    300
Leu Glu Phe Cys Ser Val Phe Lys Pro Ala Met Pro Arg Ser Val Val
65              70              75              80

GGT ACG GCT TGT ATG TAT TTC AAA CGT TTT TAT CTT AAT AAC TCA GTA    348
Gly Thr Ala Cys Met Tyr Phe Lys Arg Phe Tyr Leu Asn Asn Ser Val
            85              90              95
                                    ↓
ATG GAA TAT CAC CCC AGG ATA ATA ATG CTC ACT TGT GCA TTT TTG GCC    396
Met Glu Tyr His Pro Arg Ile Ile Met Leu Thr Cys Ala Phe Leu Ala
            100             105             110

TGC AAA GTA GAT GAA TTC AAT GTA TCT AGT CCT CAG TTT GTT GGA AAC    444
Cys Lys Val Asp Glu Phe Asn Val Ser Ser Pro Gln Phe Val Gly Asn
        115             120             125

CTC CGG GAG AGT CCT CTT GGA CAG GAG AAG GCA CTT GAA CAG ATA CTG    492
Leu Arg Glu Ser Pro Leu Gly Gln Glu Lys Ala Leu Glu Gln Ile Leu
    130             135             140

GAA TAT GAA CTA CTT CTT ATA CAG CAA CTT AAT TTC CAC CTT ATT GTC    540
Glu Tyr Glu Leu Leu Leu Ile Gln Gln Leu Asn Phe His Leu Ile Val
145             150             155             160

CAC AAT CCT TAC AGA CCA TTT GAG GGC TTC CTC ATC GAC TTA AAG ACC    588
His Asn Pro Tyr Arg Pro Phe Glu Gly Phe Leu Ile Asp Leu Lys Thr
            165             170             175

CGC TAT CCC ATA TTG GAG AAT CCA GAG ATT TTG AGG AAA ACA GCT GAT    636
Arg Tyr Pro Ile Leu Glu Asn Pro Glu Ile Leu Arg Lys Thr Ala Asp
            180             185             190
```

Fig. 2A

```
GAC TTT CTT AAT AGA ATT GCA TTG ACG GAT GCT TAC CTT TTA TAC ACA    684
Asp Phe Leu Asn Arg Ile Ala Leu Thr Asp Ala Tyr Leu Leu Tyr Thr
        195                 200                 205

CCT TCC CAA ATT GCC CTG ACT GCC ATT TTA TCT AGT GCC TCC AGG GCT    732
Pro Ser Gln Ile Ala Leu Thr Ala Ile Leu Ser Ser Ala Ser Arg Ala
        210                 215                 220

GGA ATT ACT ATG GAA AGT TAT TTA TCA GAG AGT CTG ATG CTG AAA GAG    780
Gly Ile Thr Met Glu Ser Tyr Leu Ser Glu Ser Leu Met Leu Lys Glu
225                 230                 235                 240

AAC AGA ACT TGC CTG TCA CAG TTA CTA GAT ATA ATG AAA AGC ATG AGA    828
Asn Arg Thr Cys Leu Ser Gln Leu Leu Asp Ile Met Lys Ser Met Arg
                245                 250                 255

AAC TTA GTA AAG AAG TAT GAA CCA CCC AGA TCT GAA GAA GTT GCT GTT    876
Asn Leu Val Lys Lys Tyr Glu Pro Pro Arg Ser Glu Glu Val Ala Val
            260                 265                 270

CTG AAA CAG AAG TTG GAG CGA TGT CAT TCT GCT GAG CTT GCA CTT AAC    924
Leu Lys Gln Lys Leu Glu Arg Cys His Ser Ala Glu Leu Ala Leu Asn
        275                 280                 285

GTA ATC ACG AAG AAG AGG AAA GGC TAT GAA GAT GAT GAT TAC GTC TCA    972
Val Ile Thr Lys Lys Arg Lys Gly Tyr Glu Asp Asp Asp Tyr Val Ser
        290                 295                 300

AAG AAA TCC AAA CAT GAG GAG GAA GAA TGG ACT GAT GAC GAC CTG GTA   1020
Lys Lys Ser Lys His Glu Glu Glu Glu Trp Thr Asp Asp Asp Leu Val
305                 310                 315                 320

GAA TCT CTC TAACCATTTG AAGTTGATTT CTCAATGCTA ACTAATCAAG AGAAGTAGG 1078
Glu Ser Leu
        323

AAGCATATCA AACGTTTAAC TTTATTTAAA AAGTATAATG TGAAAACATA AAATATATTA 1138
AAACTTTTCT ATTGTTTTCT TTCCCTTTCA CAGTAACTTT ATGTAAAATA AACCATCTTC 1198
AAAAG                                                             1203
```

Fig. 2B

```
ATG AAG TTT CCA GGG CCT TTG GAA AAC CAG AGA TTG TCT TTC CTG TTG   48
Met Lys Phe Pro Gly Pro Leu Glu Asn Gln Arg Leu Ser Phe Leu Leu
 1            5                  10                 15

GAA AAG GCA ATC ACT AGG GAA GCA CAG ATG TGG AAA GTG AAT GTG CGG   96
Glu Lys Ala Ile Thr Arg Glu Ala Gln Met Trp Lys Val Asn Val Arg
            20                  25                 30

AAA ATG CCT TCA AAT CAG AAT GTT TCT CCA TCC CAG AGA GAT GAA GTA  144
Lys Met Pro Ser Asn Gln Asn Val Ser Pro Ser Gln Arg Asp Glu Val
        35                  40                  45

ATT CAA TGG CTG GCC AAA CTC AAG TAC CAA TTC AAC CTT TAC CCA GAA  192
Ile Gln Trp Leu Ala Lys Leu Lys Tyr Gln Phe Asn Leu Tyr Pro Glu
    50                  55                  60

ACA TTT GCT CTG GCT AGC AGT CTT TTG GAT AGG TTT TTA GCT ACC GTA  240
Thr Phe Ala Leu Ala Ser Ser Leu Leu Asp Arg Phe Leu Ala Thr Val
65                  70                  75                  80

AAG GCT CAT CCA AAA TAC TTG AGT TGT ATT GCA ATC AGC TGT TTT TTC  288
Lys Ala His Pro Lys Tyr Leu Ser Cys Ile Ala Ile Ser Cys Phe Phe
            85                  90                  95

CTA GCT GCC AAG ACT GTT GAG GAA GAT GAG AGA ATT CCA GTA CTA AAG  336
Leu Ala Ala Lys Thr Val Glu Glu Asp Glu Arg Ile Pro Val Leu Lys
                100                 105                 110

GTA TTG GCA AGA GAC AGT TTC TGT GGA TGT TCC TCA TCT GAA ATT TTG  384
Val Leu Ala Arg Asp Ser Phe Cys Gly Cys Ser Ser Ser Glu Ile Leu
            115                 120                 125

AGA ATG GAG AGA ATT ATT CTG GAT AAG TTG AAT TGG GAT CTT CAC ACA  432
Arg Met Glu Arg Ile Ile Leu Asp Lys Leu Asn Trp Asp Leu His Thr
        130                 135                 140

GCC ACA CCA TTG GAT TTT CTT CAT ATT TTC CAT GCC ATT GCA GTG TCA  480
Ala Thr Pro Leu Asp Phe Leu His Ile Phe His Ala Ile Ala Val Ser
145                 150                 155                 160

ACT AGG CCT CAG TTA CTT TTC AGT TTG CCC AAA TTG AGC CCA TCT CAA  528
Thr Arg Pro Gln Leu Leu Phe Ser Leu Pro Lys Leu Ser Pro Ser Gln
            165                 170                 175

CAT TTG GCA GTC CTT ACC AAG CAA CTA CTT CAC TGT ATG GCC TGC AAC  576
His Leu Ala Val Leu Thr Lys Gln Leu Leu His Cys Met Ala Cys Asn
        180                 185                 190
```

Fig. 3A

```
CAA CTT CTG CAA TTC AGA GGA TCC ATG CTT GCT CTG GCC ATG GTT AGT   624
Gln Leu Leu Gln Phe Arg Gly Ser Met Leu Ala Leu Ala Met Val Ser
        195                 200                 205

CTG GAA ATG GAG AAA CTC ATT CCT GAT TGG CTT TCT CTT ACA ATT GAA   672
Leu Glu Met Glu Lys Leu Ile Pro Asp Trp Leu Ser Leu Thr Ile Glu
    210                 215                 220

CTG CTT CAG AAA GCA CAG ATG GAT AGC TCC CAG TTG ATC CAT TGT CGG   720
Leu Leu Gln Lys Ala Gln Met Asp Ser Ser Gln Leu Ile His Cys Arg
225                 230                 235                 240

GAG CTT GTG GCA CAT CAC CTT TCT ACT CTG CAG TCT TCC CTG CCT CTG   768
Glu Leu Val Ala His His Leu Ser Thr Leu Gln Ser Ser Leu Pro Leu
                245                 250                 255

AAT TCC GTT TAT GTC TAC CGT CCC CTC AAG CAC ACC CTG GTG ACC TGT   816
Asn Ser Val Tyr Val Tyr Arg Pro Leu Lys His Thr Leu Val Thr Cys
            260                 265                 270

GAC AAA GGA GTG TTC AGA TTA CAT CCC TCC TCT GTC CCA GGC CCA GAC   864
Asp Lys Gly Val Phe Arg Leu His Pro Ser Ser Val Pro Gly Pro Asp
        275                 280                 285

TTC TCC AAG GAC AAC AGC AAG CCA GAA GTG CCA GTC AGA GGT ACA GCA   912
Phe Ser Lys Asp Asn Ser Lys Pro Glu Val Pro Val Arg Gly Thr Ala
    290                 295                 300

GCC TTT TAC CAT CAT CTC CCA GCT GCC AGT GGG TGC AAG CAG ACC TCT   960
Ala Phe Tyr His His Leu Pro Ala Ala Ser Gly Cys Lys Gln Thr Ser
305                 310                 315                 320

ACT AAA CGC AAA GTA GAG GAA ATG GAA GTG GAT GAC TTC TAT GAT GGA  1008
Thr Lys Arg Lys Val Glu Glu Met Glu Val Asp Asp Phe Tyr Asp Gly
                325                 330                 335

ATC AAA CGG CTC TAT AAT GAA GAT AAT GTC TCA GAA AAT GTG GGT TCT  1056
Ile Lys Arg Leu Tyr Asn Glu Asp Asn Val Ser Glu Asn Val Gly Ser
            340                 345                 350

GTG TGT GGC ACT GAT TTA TCA AGA CAA GAG GGA CAT GCT TCC CCT TGT  1104
Val Cys Gly Thr Asp Leu Ser Arg Gln Glu Gly His Ala Ser Pro Cys
        355                 360                 365

CCA CCT TTG CAG CCT GTT TCT GTC ATG TAGTTTCAAC AAGTGCTACC TTTGAGT 1158
Pro Pro Leu Gln Pro Val Ser Val Met
    370                 375 377

GTAAACTAAG GTAGACTACT TTGGGAATGA GAACATCCAA AATCAGGAAA GGCTGTAGAA 1218
GGAAATATAC CTTAACAGGC TGATTTGGAG TGACCCAGAA AA                 1260
```

Fig. 3B

```
GGCACGAGGT TGTAGTTAAG CTCGTGTAAC GGCGGCGGTG TCGGTAGCTG CTGTAGCGAA  60

GAGAGTTTGG CGCG ATG TCT CAC ACC ATT TTG CTG GTA CAG CCT ACC AAG  110
                Met Ser His Thr Ile Leu Leu Val Gln Pro Thr Lys
                 1       5                       10

AGG CCA GAA GGC AGA ACT TAT GCT GAC TAC GAA TCT GTG AAT GAA TGC  158
Arg Pro Glu Gly Arg Thr Tyr Ala Asp Tyr Glu Ser Val Asn Glu Cys
         15              20                  25

ATG GAA GGT GTT TGT AAA ATG TAT GAA GAA CAT CTG AAA AGA ATG AAT  206
Met Glu Gly Val Cys Lys Met Tyr Glu Glu His Leu Lys Arg Met Asn
     30              35                  40

CCC AAC AGT CCC TCT ATC ACA TAT GAC ATC AGT CAG TTG TTT GAT TTC  254
Pro Asn Ser Pro Ser Ile Thr Tyr Asp Ile Ser Gln Leu Phe Asp Phe
45              50                  55                      60

ATC GAT GAT CTG GCA GAC CTC AGC TGC CTG GTT TAC CGA GCT GAT ACC  302
Ile Asp Asp Leu Ala Asp Leu Ser Cys Leu Val Tyr Arg Ala Asp Thr
                 65                  70                  75

CAG ACA TAC CAG CCT TAT AAC AAA GAC TGG ATT AAA GAG AAG ATC TAC  350
Gln Thr Tyr Gln Pro Tyr Asn Lys Asp Trp Ile Lys Glu Lys Ile Tyr
             80                  85                  90

GTG CTC CTT CGT CGG CAG GCC CAA CAG GCT GGG AAA TAATTGTGTT GGAAGC  402
Val Leu Leu Arg Arg Gln Ala Gln Gln Ala Gly Lys
         95                 100             104

ACTGGGGGGG TTGGGGTGGG CTTGGAACAC AGGTGTGTAC AGCGTGCTGT AGTGGAAGTT  462
TTGTATCATA GTAATCCTGT TTCCACTTTG TTATACTCTA GCCAAGATTG ACTGTATTAG  522
ATGAAATGTG AGGATCTTGT TCAATCGGAA ACCCCCGTTA CCTCCTCTTT TTCTTTCTCT  582
TTCTTTTTTT TTTTTTACTT AAACATTTTT ATGATGATTT AGATGGAAGT TGTTCTTCGT  642
CACTTAATGT TGGTTCCAGT CCTTCAACTG TTCATATCTA CTTTATAACA TTCACATACT  702
AACCCTTCTG GGGTTCAAGA TGGGGGGTGG CAAATGCAGT TTAGCCATGT CCTCAAGATA  762
AAGTCTTGGT AAAAATAAAT AAATGTCCTT TAGTT                             797
```

Fig. 4

```
  1 GGAAGATGGC GGCTGTGGTG GAGAATGTAG TGAAGCTCCT TGGGGAGCAG TACTACAAAG
 61 ATGCCATGGA GCAGTGCCAC AATTACAATG CTCGCCTCTG TGCTGAGCGC AGCGTGCGCC
121 TGCCTTTCTT GGACTCACAG ACCGGAGTAG CCCAGAGCAA TTGTTACATC TGGATGGAAA
181 AGCGACACCG GGGTCCAGGA TTGGCCTCCG GACAGCTGTA CTCCTACCCT GCCCGGCGCT
241 GGCGGAAAAA GCGGCGAGCC CATCCCCCTG AGGATCCACG ACTTTCCTTC CCATCTATTA
301 AGCCAGACAC AGACCAGACC CTGAAGAAGG AGGGGCTGAT CTCTCAGGAT GGCAGTAGTT
361 TAGAGGCTCT GTTGCGCACT GACCCCCTGG AGAAGCGAGG TGCCCCGGAT CCCCGAGTTG
421 ATGATGACAG CCTGGGCGAG TTTCCTGTGA CCAACAGTCG AGCGCGAAAG CGGATCCTAG
481 AACCAGATGA CTTCCTGGAT GACCTCGATG ATGAAGACTA TGAAGAAGAT ACTCCCAAGC
541 GTCGGGGAAA GGGGAAATCC AAGGGTAAGG GTGTGGGCAG TGCCCGTAAG AAGCTGGATG
601 CTTCCATCCT GGAGGACCGG GATAAGCCCT ATGCCTGTGA CATTTGTGGA AAACGTTACA
661 AGAACCGACC AGGCCTCAGT TACCACTATG CCCACTCCCA CTTGGCTGAG GAGGAGGGCG
721 AGGACAAGGA AGACTCTCAA CCACCCACTC CTGTTTCCCA GAGGTCTGAG GAGCAGAAAT
781 CCAAAAAGGG TCCTGATGGA TTGGCCTTGC CCAACAACTA CTGTGACTTC TGCCTGGGGG
841 ACTCAAAGAT TAACAAGAAG ACGGGACAAC CCGAGGAGCT GGTGTCTTGT TCTGACTGTG
901 GCCGCTCAGG GCATCCATCT TGCCTCCAAT TTACCCCCGT GATGATGGCG GCAGTGAAGA
961 CATACCGCTG GCAGTGCATC GAGTGCAAAT GTTGCAATAT CTGCGGCACC TCCGAGAATG
1021 ACGACCAGTT GCTCTTCTGT GATGACTGCG ATCGTGGCTA CCACATGTAC TGTCTCACCC
1081 CGTCCATGTC TGAGCCCCCT GAAGGAAGTT GGAGCTGCCA CCTGTGTCTG GACCTGTTGA
1141 AAGAGAAAGC TTCCATCTAC CAGAACCAGA ACTCCTCTTG ATGTGGCCAC CCACCTGCTC
1201 CCCGACATAT CTAAGGCTGT TTCTCTCCTC CACTTCATAT TTCATACCCA TCTTTCCCTT
```

Fig. 5A

```
1261 CTTCCTCCTC TCCTTCACAA ATCCAGAGAA CCTTGGGGTG GTTGTGCCAG CCTGCCTTTG

1321 GCAGCTGCAA GCTGAGGTGG CAGCTCTGAC CACCTCTGGC CCCAGGCCTC AGGGAGAAAG

1381 GAGCAACACA CTGCCCCTAG GCGTGCGTGT GGCCCAGTTT CTCTCTGCTC TCCATTAAGT

1441 GCATTCACTC TGCTTGCCTT GGGCCCAGCC CCTGGTGATC ACAGGGTTCA AACAGTGTCC

1501 TCCTAGAAAG AGTGGGAGAG CAGCTCACTT CTCTGTGTTC TGCCTCCCCT CTGGTCTCCA

1561 GAGTTTTCCT GTCCTCTAGA GGCAAGCCAG GCCAGGGAGC TGGGAGCGAG CAAGCTGAGG

1621 CCACGTCCAC AAGGAGCTTT TCATGCCCCT GTGCCGCATA GCCTCACCTC TTTCCTCCAG

1681 AGTGGCTCTC TGCGGCCCTG TGTTCCTGCT ACAGAGTGTT CTTTTCTGGA GTCAGGATGT

1741 TCTCGGTCAC CCTCCTGGTT CTGCCCTGTC CCATTCCACC CCACCCCAGG GGGAACAGTA

1801 GCTTCACCTT GTTATTCCCA TTGCTCTCCT GGCTCACTCT TACGGTCGGT CTCCAGTGAC

1861 TGAAGCATTC CCCACCCTTG GAATTTCTCA TCTTCTGCCT CCCTTCCTAC TCCTTTTGGT

1921 TTTGTGGGGA GAGGGGAAGG ATCAGGGGGC AAGGCCAGCA GCTCGGGGGC CACAAGGAGA

1981 TGGATAATGT GCCTGTTTTT TAACACAACA AAAAAGCCTA CCTCCAAAAT CCCCTTTTTG

2041 TTCTTCCTGG ACCTGGGCAT TCAGCCTCCT GCTCTTAACT GAATTGGGAG CCTCTGCCAC

2101 CTGCCCCGTG TATCCTGGCT CTCAGCTCAT GGGGAAGCCA CATAGACATC CCTTTCTTCC

2161 CTTGCACGCT CGCTAGCAGC TGGTAGGTCT TCACACCCTG ATTCCTCAAG TTTTCTGCTT

2221 AGTGGCACTG ACATTAAGTA GTGGGGGGAC AGTCCATGCC AGGACACCCT GGAGTAGCCT

2281 TCCCCCTTGG CCGTGGGCAG GCCCTAACTC ACTGTCGCTT TGGAGTTGAG GTGTCTTTTT

2341 TTTTCTTTC TTTAGTTCCT GTATTCTAAA CATTAGTAAA AATAAATGTT TTTACACAG
                                                                2400
```

Fig. 5B

```
  1 ATG GCG GCT GTG GTG GAG AAT GTA GTG AAG CTC CTT GGG GAG CAG
    Met Ala Ala Val Val Glu Gln Val Val Lys Leu Leu Gly Glu Gln
    1               5                   10                  15

46 TAC TAC AAA GAT GCC ATG GAG CAG TGC CAC AAT TAC AAT GCT CGC
    Tyr Tyr Lys Asp Ala Met Glu Gln Cys His Asn Tyr Asn Ala Arg
                    20                  25                  30

91 CTC TGT GCT GAG CGC AGC GTG CGC CTG CCT TTC TTG GAC TCA CAG
    Leu Cys Ala Glu Arg Ser Val Arg Leu Pro Phe Leu Asp Ser Gln
                    35                  40                  45

136 ACC GGA GTA GCC CAG AGC AAT TGT TAC ATC TGG ATG GAA AAG CGA
    Thr Gly Val Ala Gln Ser Asn Cys Tyr Ile Trp Met Glu Lys Arg
                    50                  55                  60

181 CAC CGG GGT CCA GGA TTG GCC TCC GGA CAG CTG TAC TCC TAC CCT
    His Arg Gly Pro Gly Leu Ala Ser Gly Gln Ley Tyr Ser Tyr Pro
                    65                  70                  75

226 GCC CGG CGC TGG CGG AAA AAG CGG CGA GCC CAT CCC CCT GAG GAT
    Ala Arg Arg Trp Arg Lys Lys Arg Arg Ala His Pro Pro Glu Asp
                    80                  85                  90

271 CCA CGA CTT TCC TTC CCA TCT ATT AAG CCA GAC ACA GAC CAG ACC
    Pro Arg Leu Ser Phe Pro Ser Ile Lys Pro Asp Thr Asp Gln Thr
                    95                  100                 105

316 CTG AAG AAG GAG GGG CTG ATC TCT CAG GAT GGC AGT AGT TTA GAG
    Leu Lys Lys Glu Gly Leu Ile Ser Gln Asp Gly Ser Ser Leu Glu
                    110                 115                 120
```

Fig. 6A

```
361  GCT CTG TTG CGC ACT GAC CCC CTG GAG AAG CGA GGT GCC CCG GAT
     Ala Leu Leu Arg Thr Asp Pro Leu Glu Lys Arg Gly Ala Pro Asp
                     125             130             135

406  CCC CGA GTT GAT GAT GAC AGC CTG GGC GAG TTT CCT GTG ACC AAC
     Pro Arg Val Asp Asp Asp Ser Leu Gly Glu Phe Pro Val Thr Asn
                     140             145             150

451  AGT CGA GCG CGA AAG CGG ATC CTA GAA CCA GAT GAC TTC CTG GAT
     Ser Arg Ala Arg Lys Arg Ile Leu Glu Pro Asp Asp Phe Leu Asp
                     155             160             165

496  GAC CTC GAT GAT GAA GAC TAT GAA GAA GAT ACT CCC AAG CGT CGG
     Asp Leu Asp Asp Glu Asp Tyr Glu Glu Asp Thr Pro Lys Arg Arg
                     170       Ⓐ      175             180
                              ↓
541  GGA AAG GGG AAA TCC AAG GAG GCA AGC CAG GCC AGG GAG CTG GGA
     Gly Lys Gly Lys Ser Lys Glu Ala Ser Gln Ala Arg Glu Leu Gly
                     185             190             195

586  GCG AGC AAG CTG AGG CCA CGT CCA CAA GGA GCT TTT CAT GCC CCT
     Ala Ser Lys Leu Arg Pro Arg Pro Gln Gly Ala Phe His Ala Pro
                     200             205             210

631  GTG CCG CAT AGC CTC ACC TCT TTC CTC CAG AGT GGC TCT CTG CGG
     Val Pro His Ser Leu Thr Ser Phe Leu Gln Ser Gly Ser Leu Arg
                     215             220             225
```

Fig. 6B

```
676 CCC TGT GTT CCT GCT ACA GAG TGT TCT TTT CTG GAG TCA GGA TGT
    Pro Cys Val Pro Ala Thr Glu Cys Ser Phe Leu Glu Ser Gly Cys
                        230                 235                 240

721 TCT CGG TCA CCC TCC TGG TTC TGC CCT GTC CCA TTC CAC CCC ACC
    Ser Arg Ser Pro Ser Trp Phe Cys Pro Val Pro Phe His Pro Thr
         ↓ⒷB        245                 250         ↓Ⓒ         255

766 CCA GGG GGA ACA GTA GCT TCA CCT TGT TAT TCC CAT TGC TCT CCT
    Pro Gly Gly Thr Val Ala Ser Pro Cys Tyr Ser His Cys Ser Pro
                        260                 265                 270

811 GGC TCA CTC TTA CGG TCG GTC TCC AGT GAC TGA 843
    Gly Ser Leu Leu Arg Ser Val Ser Ser Asp *
                        275                 280
```

Fig. 6C

```
  1 ATG GCG GCT GTG GTG GAG AAT GTA GTG AAG CTC CTT GGG GAG CAG
    Met Ala Ala Val Val Glu Asn Val Val Lys Leu Leu Gly Glu Gln
    1               5                   10                  15

46 TAC TAC AAA GAT GCC ATG GAG CAG TGC CAC AAT TAC AAT GCT CGC
    Tyr Tyr Lys Asp Ala Met Glu Gln Cys His Asn Tyr Asn Ala Arg
                    20                  25                  30

91 CTC TGT GCT GAG CGC AGC GTG CGC CTG CCT TTC TTG GAC TCA CAG
    Leu Cys Ala Glu Arg Ser Val Arg Leu Pro Phe Leu Asp Ser Gln
                    35                  40                  45

136 ACC GGA GTA GCC CAG AGC AAT TGT TAC ATC TGG ATG GAA AAG CGA
    Thr Gly Val Ala Gln Ser ASN Cys Tyr Ile Trp Met Glu Lys Arg
                    50                  55                  60

181 CAC CGG GGT CCA GGA TTG GCC TCC GGA CAG CTG TAC TCC TAC CCT
    His Arg Gly Pro Gly Leu Ala Ser Gly Gln Leu Tyr Ser Tyr Pro
                    65                  70                  75

226 GCC CGG CGC TGG CGG AAA AAG CGG CGA GCC CAT CCC CCT GAG GAT
    Ala Arg Arg Trp Arg Lys Lys Arg Arg Ala His Pro Pro Glu Asp
                    80                  85                  90

271 CCA CGA CTT TCC TTC CCA TCT ATT AAG CCA GAC ACA GAC CAG ACC
    Pro Arg Leu Ser Phe Pro Ser Ile Lys Pro Asp Thr Asp Gln Thr
                    95                  100                 105

316 CTG AAG AAG GAG GGG CTG ATC TCT CAG GAT GGC AGT AGT TTA GAG
    Leu Lys Lys Glu Gly Leu Ile Ser Gln Asp Gly Ser Ser Leu Glu
                    110                 115                 120
```

Fig. 7A

```
361  GCT CTG TTG CGC ACT GAC CCC CTG GAG AAG CGA GGT GCC CCG GAT
     Ala Leu Leu Arg Thr Asp Pro Leu Glu Lys Arg Gly Ala Pro Asp
                     125             130                     135

406  CCC CGA GTT GAT GAT GAC AGC CTG GGC GAG TTT CCT GTG ACC AAC
     Pro Arg Val Asp Asp Asp Ser Leu Gly Glu Phe Pro Val Thr Asn
                     140             145                     150

451  AGT CGA GCG CGA AAG CGG ATC CTA GAA CCA GAT GAC TTC CTG GAT
     Ser Arg Ala Arg Lys Arg Ile Glu Leu Pro Asp Asp Phe Leu Asp
                     155             160                     165

496  GAC CTC GAT GAT GAA GAC TAT GAA GAA GAT ACT CCC AAG CGT CGG
     Asp Leu Asp Asp Glu Asp Tyr Glu Glu Asp Thr Pro Lys Arg Arg
                     170             175                     180
                                      ↓Ⓐ
541  GGA AAG GGG AAA TCC AAG GGG GGA ACA GTA GCT TCA CCT TGT TAT
     Gly Lys Gly Lys Ser Lys Gly Gly Thr Val Ala Ser Pro Cys Tyr
       ↓Ⓑ              185             190                     195

586  TCC CAT TGC TCT CCT GGC TCA CTC TTA CGG TCG GTC TCC AGT GAC
     Ser His Cys Ser Pro Gly Ser Leu Leu Arg Ser Val Ser Ser Asp
                     200             205                     210

631  TGA 633
      *
```

Fig. 7B

PREY PROTEINS

|  | Cyc.H | ERH | p27 | P1 | p21 | hsReq |
|---|---|---|---|---|---|---|
| CDK2 | A + | B + | C + |  | D + | E + |
| B1 |  |  |  | F + |  |  |

BAIT PROTEINS

Fig. 9

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 1476 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: Coding Sequence
      (B) LOCATION: 1...894
      (D) OTHER INFORMATION:

(xi) SEQUENCE DESCRIPTION: SEQ ID NO:1:

```
ATG GAG AAC TTC CAA AAG GTG GAA AAG ATC GGA GAG GGC ACG TAC GGA      48
Met Glu Asn Phe Gln Lys Val Glu Lys Ile Gly Glu Gly Thr Tyr Gly
1               5                   10                  15

GTT GTG TAC AAA GCC AGA AAC AAG TTG ACG GGA GAG GTG GTG GCG CTT      96
Val Val Tyr Lys Ala Arg Asn Lys Leu Thr Gly Glu Val Val Ala Leu
            20                  25                  30

AAG AAA ATC CGC CTG GAC ACT GAG ACT GAG GGT GTG CCC AGT ACT GCC     144
Lys Lys Ile Arg Leu Asp Thr Glu Thr Glu Gly Val Pro Ser Thr Ala
        35                  40                  45

ATC CGA GAG ATC TCT CTG CTT AAG GAG CTT AAC CAT CCT AAT ATT GTC     192
Ile Arg Glu Ile Ser Leu Leu Lys Glu Leu Asn His Pro Asn Ile Val
    50                  55                  60

AAG CTG CTG GAT GTC ATT CAC ACA GAA AAT AAA CTC TAC CTG GTT TTT     240
Lys Leu Leu Asp Val Ile His Thr Glu Asn Lys Leu Tyr Leu Val Phe
65                  70                  75                  80
```

```
GAA TTT CTG CAC CAA GAT CTC AAG AAA TTC ATG GAT GCC TCT GCT CTC      288
Glu Phe Leu His Gln Asp Leu Lys Lys Phe Met Asp Ala Ser Ala Leu
                         85                  90                  95

ACT GGC ATT CCT CTT CCC CTC ATC AAG AGC TAT CTG TTC CAG CTG CTC      336
Thr Gly Ile Pro Leu Pro Leu Ile Lys Ser Tyr Leu Phe Gln Leu Leu
                100                 105                 110

CAG GGC CTA GCT TTC TGC CAT TCT CAT CGG GTC CTC CAC CGA GAC CTT      384
Gln Gly Leu Ala Phe Cys His Ser His Arg Val Leu His Arg Asp Leu
            115                 120                 125

AAA CCT CAG AAT CTG CTT ATT AAC ACA GAG GGG GCC ATC AAG CTA GCA      432
Lys Pro Gln Asn Leu Leu Ile Asn Thr Glu Gly Ala Ile Lys Leu Ala
        130                 135                 140

GAC TTT GGA CTA GCC AGA GCT TTT GGA GTC CCT GTT CGT ACT TAC ACC      480
Asp Phe Gly Leu Ala Arg Ala Phe Gly Val Pro Val Arg Thr Tyr Thr
145                 150                 155                 160

CAT GAG GTG GTG ACC CTG TGG TAC CGA GCT CCT GAA ATC CTC CTG GGC      528
His Glu Val Val Thr Leu Trp Tyr Arg Ala Pro Glu Ile Leu Leu Gly
                165                 170                 175

TCG AAA TAT TAT TCC ACA GCT GTG GAC ATC TGG AGC CTG GGC TGC ATC      576
Ser Lys Tyr Tyr Ser Thr Ala Val Asp Ile Trp Ser Leu Gly Cys Ile
                180                 185                 190

TTT GCT GAG ATG GTG ACT CGC CGG GCC CTG TTC CCT GGA GAT TCT GAG      624
Phe Ala Glu Met Val Thr Arg Arg Ala Leu Phe Pro Gly Asp Ser Glu
            195                 200                 205

ATT GAC CAG CTC TTC CGG ATC TTT CGG ACT CTG GGG ACC CCA GAT GAG      672
Ile Asp Gln Leu Phe Arg Ile Phe Arg Thr Leu Gly Thr Pro Asp Glu
        210                 215                 220

GTG GTG TGG CCA GGA GTT ACT TCT ATG CCT GAT TAC AAG CCA AGT TTC      720
Val Val Trp Pro Gly Val Thr Ser Met Pro Asp Tyr Lys Pro Ser Phe
225                 230                 235                 240

CCC AAG TGG GCC CGG CAA GAT TTT AGT AAA GTT GTA CCT CCC CTG GAT      768
Pro Lys Trp Ala Arg Gln Asp Phe Ser Lys Val Val Pro Pro Leu Asp
                245                 250                 255

GAA GAT GGA CGG AGC TTG TTA TCG CAA ATG CTG CAC TAC GAC CCT AAC      816
Glu Asp Gly Arg Ser Leu Leu Ser Gln Met Leu His Tyr Asp Pro Asn
                260                 265                 270

AAG CGG ATT TCG GCC AAG GCA GCC CTG GCT CAC CCT TTC TTC CAG GAT      864
Lys Arg Ile Ser Ala Lys Ala Ala Leu Ala His Pro Phe Phe Gln Asp
            275                 280                 285

GTG ACC AAG CCA GTA CCC CAT CTT CGA CTC TGATAGCCTT CTTGAAGCCC CCG    917
Val Thr Lys Pro Val Pro His Leu Arg Leu
        290                 295

ACCCTAATCG GCTCACCCTC TCCTCCAGTG TGGGCTTGAC CAGCTTGGCC TTGGGCTATT    977

TGGACTCAGG TGGGCCCTCT GAACTTGCCT TAAACACTCA CCTTCTAGTC TTAACCAGCC   1037

AACTCTGGGA ATACAGGGGT GAAAGGGGGG AACCAGTGAA AATGAAAGGA AGTTTCAGTA   1097

TTAGATGCAC TTAAGTTAGC CTCCACCACC CTTTCCCCCT TCTCTTAGTT ATTGCTGAAG   1157

AGGGTTGGTA TAAAAATAAT TTTAAAAAAG CCTTCCTACA CGTTAGATTT GCCGTACCAA   1217

TCTCTGAATG CCCCATAATT ATTATTTCCA GTGTTTGGGA TGACCAGGAT CCCAAGCCTC   1277

CTGCTGCCAC AATGTTTATA AAGGCCAAAT GATAGCGGGG GCTAAGTTGG TGCTTTTGAG   1337

AATTAAGTAA AACAAAACCA CTGGGAGGAG TCTATTTTAA AGAATTCGGT TAAAAAATAG   1397

ATCCAATCAG TTTATACCCT AGTTAGTGTT TTCCTCACCT AATAGGCTGG GAGACTGAAG   1457

ACTCAGCCCG GGTGGGGGT                                               1476
```

(2) INFORMATION FOR SEQ ID NO:2:

```
    (i) SEQUENCE CHARACTERISTICS:
        (A) LENGTH: 298 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:2:

Met Glu Asn Phe Gln Lys Val Glu Lys Ile Gly Glu Gly Thr Tyr Gly
 1               5                  10                  15

Val Val Tyr Lys Ala Arg Asn Lys Leu Thr Gly Glu Val Val Ala Leu
            20                  25                  30

Lys Lys Ile Arg Leu Asp Thr Glu Thr Glu Gly Val Pro Ser Thr Ala
        35                  40                  45

Ile Arg Glu Ile Ser Leu Leu Lys Glu Leu Asn His Pro Asn Ile Val
    50                  55                  60

Lys Leu Leu Asp Val Ile His Thr Glu Asn Lys Leu Tyr Leu Val Phe
65                  70                  75                  80

Glu Phe Leu His Gln Asp Leu Lys Lys Phe Met Asp Ala Ser Ala Leu
                85                  90                  95

Thr Gly Ile Pro Leu Pro Leu Ile Lys Ser Tyr Leu Phe Gln Leu Leu
            100                 105                 110

Gln Gly Leu Ala Phe Cys His Ser His Arg Val Leu His Arg Asp Leu
        115                 120                 125

Lys Pro Gln Asn Leu Leu Ile Asn Thr Glu Gly Ala Ile Lys Leu Ala
    130                 135                 140

Asp Phe Gly Leu Ala Arg Ala Phe Gly Val Pro Val Arg Thr Tyr Thr
145                 150                 155                 160

His Glu Val Val Thr Leu Trp Tyr Arg Ala Pro Glu Ile Leu Leu Gly
                165                 170                 175

Ser Lys Tyr Tyr Ser Thr Ala Val Asp Ile Trp Ser Leu Gly Cys Ile
            180                 185                 190

Phe Ala Glu Met Val Thr Arg Arg Ala Leu Phe Pro Gly Asp Ser Glu
        195                 200                 205

Ile Asp Gln Leu Phe Arg Ile Phe Arg Thr Leu Gly Thr Pro Asp Glu
    210                 215                 220

Val Val Trp Pro Gly Val Thr Ser Met Pro Asp Tyr Lys Pro Ser Phe
225                 230                 235                 240

Pro Lys Trp Ala Arg Gln Asp Phe Ser Lys Val Val Pro Pro Leu Asp
                245                 250                 255

Glu Asp Gly Arg Ser Leu Leu Ser Gln Met Leu His Tyr Asp Pro Asn
            260                 265                 270

Lys Arg Ile Ser Ala Lys Ala Ala Leu Ala His Pro Phe Phe Gln Asp
        275                 280                 285

Val Thr Lys Pro Val Pro His Leu Arg Leu
    290                 295

(2) INFORMATION FOR SEQ ID NO:3:

(i) SEQUENCE CHARACTERISTICS:
        (A) LENGTH: 1203 base pairs
        (B) TYPE: nucleic acid
        (C) STRANDEDNESS: single
        (D) TOPOLOGY: linear (ii) MOLECULE TYPE: DNA
```

(ix) FEATURE:
    (A) NAME/KEY: Coding Sequence
    (B) LOCATION: 61...1029
    (D) OTHER INFORMATION:

(xi) SEQUENCE DESCRIPTION: SEQ ID NO:3:

```
GGACGCTGAT GCGTTTGGGT TCTCGTCTGC AGACCCTCTG GACCTGGTCA CGATTCCATA    60

ATG TAC CAC AAC AGT AGT CAG AAG CGG CAC TGG ACC TTC TCC AGC GAG    108
Met Tyr His Asn Ser Ser Gln Lys Arg His Trp Thr Phe Ser Ser Glu
 1               5                  10                  15

GAG CAG CTG GCA AGA CTG CGG GCT GAC GCC AAC CGC AAA TTC AGA TGC    156
Glu Gln Leu Ala Arg Leu Arg Ala Asp Ala Asn Arg Lys Phe Arg Cys
              20                  25                  30

AAA GCC GTG GCC AAC GGG AAG GTT CTT CCG AAT GAT CCA GTC TTT CTT    204
Lys Ala Val Ala Asn Gly Lys Val Leu Pro Asn Asp Pro Val Phe Leu
         35                  40                  45

GAG CCT CAT GAA GAA ATG ACA CTC TGC AAA TAC TAT GAG AAA AGG TTA    252
Glu Pro His Glu Glu Met Thr Leu Cys Lys Tyr Tyr Glu Lys Arg Leu
     50                  55                  60

TTG GAA TTC TGT TCG GTG TTT AAG CCA GCA ATG CCA AGA TCT GTT GTG    300
Leu Glu Phe Cys Ser Val Phe Lys Pro Ala Met Pro Arg Ser Val Val
 65                  70                  75                  80

GGT ACG GCT TGT ATG TAT TTC AAA CGT TTT TAT CTT AAT AAC TCA GTA    348
Gly Thr Ala Cys Met Tyr Phe Lys Arg Phe Tyr Leu Asn Asn Ser Val
                 85                  90                  95

ATG GAA TAT CAC CCC AGG ATA ATA ATG CTC ACT TGT GCA TTT TTG GCC    396
Met Glu Tyr His Pro Arg Ile Ile Met Leu Thr Cys Ala Phe Leu Ala
            100                 105                 110

TGC AAA GTA GAT GAA TTC AAT GTA TCT AGT CCT CAG TTT GTT GGA AAC    444
Cys Lys Val Asp Glu Phe Asn Val Ser Ser Pro Gln Phe Val Gly Asn
        115                 120                 125

CTC CGG GAG AGT CCT CTT GGA CAG GAG AAG GCA CTT GAA CAG ATA CTG    492
Leu Arg Glu Ser Pro Leu Gly Gln Glu Lys Ala Leu Glu Gln Ile Leu
    130                 135                 140

GAA TAT GAA CTA CTT CTT ATA CAG CAA CTT AAT TTC CAC CTT ATT GTC    540
Glu Tyr Glu Leu Leu Leu Ile Gln Gln Leu Asn Phe His Leu Ile Val
145                 150                 155                 160

CAC AAT CCT TAC AGA CCA TTT GAG GGC TTC CTC ATC GAC TTA AAG ACC    588
His Asn Pro Tyr Arg Pro Phe Glu Gly Phe Leu Ile Asp Leu Lys Thr
                165                 170                 175

CGC TAT CCC ATA TTG GAG AAT CCA GAG ATT TTG AGG AAA ACA GCT GAT    636
Arg Tyr Pro Ile Leu Glu Asn Pro Glu Ile Leu Arg Lys Thr Ala Asp
            180                 185                 190

GAC TTT CTT AAT AGA ATT GCA TTG ACG GAT GCT TAC CTT TTA TAC ACA    684
Asp Phe Leu Asn Arg Ile Ala Leu Thr Asp Ala Tyr Leu Leu Tyr Thr
        195                 200                 205

CCT TCC CAA ATT GCC CTG ACT GCC ATT TTA TCT AGT GCC TCC AGG GCT    732
Pro Ser Gln Ile Ala Leu Thr Ala Ile Leu Ser Ser Ala Ser Arg Ala
    210                 215                 220

GGA ATT ACT ATG GAA AGT TAT TTA TCA GAG AGT CTG ATG CTG AAA GAG    780
Gly Ile Thr Met Glu Ser Tyr Leu Ser Glu Ser Leu Met Leu Lys Glu
225                 230                 235                 240

AAC AGA ACT TGC CTG TCA CAG TTA CTA GAT ATA ATG AAA AGC ATG AGA    828
Asn Arg Thr Cys Leu Ser Gln Leu Leu Asp Ile Met Lys Ser Met Arg
                245                 250                 255

AAC TTA GTA AAG AAG TAT GAA CCA CCC AGA TCT GAA GAA GTT GCT GTT    876
Asn Leu Val Lys Lys Tyr Glu Pro Pro Arg Ser Glu Glu Val Ala Val
            260                 265                 270

CTG AAA CAG AAG TTG GAG CGA TGT CAT TCT GCT GAG CTT GCA CTT AAC    924
Leu Lys Gln Lys Leu Glu Arg Cys His Ser Ala Glu Leu Ala Leu Asn
```

```
                275                 280                 285
GTA ATC ACG AAG AAG AGG AAA GGC TAT GAA GAT GAT GAT TAC GTC TCA      972
Val Ile Thr Lys Lys Arg Lys Gly Tyr Glu Asp Asp Asp Tyr Val Ser
        290                 295                 300

AAG AAA TCC AAA CAT GAG GAG GAA GAA TGG ACT GAT GAC GAC CTG GTA     1020
Lys Lys Ser Lys His Glu Glu Glu Glu Trp Thr Asp Asp Asp Leu Val
305                 310                 315                 320

GAA TCT CTC TAACCATTTG AAGTTGATTT CTCAATGCTA ACTAATCAAG AGAAGTAGG   1078
Glu Ser Leu
AAGCATATCA AACGTTTAAC TTTATTTAAA AAGTATAATG TGAAAACATA AAATATATTA   1138

AAACTTTTCT ATTGTTTTCT TTCCCTTTCA CAGTAACTTT ATGTAAAATA AACCATCTTC   1198

AAAAG                                                               1203

(2) INFORMATION FOR SEQ ID NO:4:

(i) SEQUENCE CHARACTERISTICS:
        (A) LENGTH: 323 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:4:

Met Tyr His Asn Ser Ser Gln Lys Arg His Trp Thr Phe Ser Ser Glu
1               5                   10                  15

Glu Gln Leu Ala Arg Leu Arg Ala Asp Ala Asn Arg Lys Phe Arg Cys
                20                  25                  30

Lys Ala Val Ala Asn Gly Lys Val Leu Pro Asn Asp Pro Val Phe Leu
            35                  40                  45

Glu Pro His Glu Glu Met Thr Leu Cys Lys Tyr Tyr Glu Lys Arg Leu
        50                  55                  60

Leu Glu Phe Cys Ser Val Phe Lys Pro Ala Met Pro Arg Ser Val Val
65                  70                  75                  80

Gly Thr Ala Cys Met Tyr Phe Lys Arg Phe Tyr Leu Asn Asn Ser Val
                85                  90                  95

Met Glu Tyr His Pro Arg Ile Ile Met Leu Thr Cys Ala Phe Leu Ala
                100                 105                 110

Cys Lys Val Asp Glu Phe Asn Val Ser Ser Pro Gln Phe Val Gly Asn
            115                 120                 125

Leu Arg Glu Ser Pro Leu Gly Gln Glu Lys Ala Leu Glu Gln Ile Leu
        130                 135                 140

Glu Tyr Glu Leu Leu Leu Ile Gln Gln Leu Asn Phe His Leu Ile Val
145                 150                 155                 160

His Asn Pro Tyr Arg Pro Phe Glu Gly Phe Leu Ile Asp Leu Lys Thr
                165                 170                 175

Arg Tyr Pro Ile Leu Glu Asn Pro Glu Ile Leu Arg Lys Thr Ala Asp
            180                 185                 190

Asp Phe Leu Asn Arg Ile Ala Leu Thr Asp Ala Tyr Leu Leu Tyr Thr
        195                 200                 205

Pro Ser Gln Ile Ala Leu Thr Ala Ile Leu Ser Ser Ala Ser Arg Ala
    210                 215                 220

Gly Ile Thr Met Glu Ser Tyr Leu Ser Glu Ser Leu Met Leu Lys Glu
225                 230                 235                 240

Asn Arg Thr Cys Leu Ser Gln Leu Leu Asp Ile Met Lys Ser Met Arg
                245                 250                 255
```

-continued

```
Asn Leu Val Lys Lys Tyr Glu Pro Pro Arg Ser Glu Glu Val Ala Val
            260                 265                 270

Leu Lys Gln Lys Leu Glu Arg Cys His Ser Ala Glu Leu Ala Leu Asn
        275                 280                 285

Val Ile Thr Lys Lys Arg Lys Gly Tyr Glu Asp Asp Tyr Val Ser
    290                 295                 300

Lys Lys Ser Lys His Glu Glu Glu Trp Thr Asp Asp Leu Val
305                 310                 315                 320

Glu Ser Leu
```

(2) INFORMATION FOR SEQ ID NO:5:

(i) SEQUENCE CHARACTERISTICS:
        (A) LENGTH: 1260 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 1...1131
        (D) OTHER INFORMATION:

(xi) SEQUENCE DESCRIPTION: SEQ ID NO:5:

```
ATG AAG TTT CCA GGG CCT TTG GAA AAC CAG AGA TTG TCT TTC CTG TTG      48
Met Lys Phe Pro Gly Pro Leu Glu Asn Gln Arg Leu Ser Phe Leu Leu
1               5                   10                  15

GAA AAG GCA ATC ACT AGG GAA GCA CAG ATG TGG AAA GTG AAT GTG CGG      96
Glu Lys Ala Ile Thr Arg Glu Ala Gln Met Trp Lys Val Asn Val Arg
                20                  25                  30

AAA ATG CCT TCA AAT CAG AAT GTT TCT CCA TCC CAG AGA GAT GAA GTA     144
Lys Met Pro Ser Asn Gln Asn Val Ser Pro Ser Gln Arg Asp Glu Val
            35                  40                  45

ATT CAA TGG CTG GCC AAA CTC AAG TAC CAA TTC AAC CTT TAC CCA GAA     192
Ile Gln Trp Leu Ala Lys Leu Lys Tyr Gln Phe Asn Leu Tyr Pro Glu
        50                  55                  60

ACA TTT GCT CTG GCT AGC AGT CTT TTG GAT AGG TTT TTA GCT ACC GTA     240
Thr Phe Ala Leu Ala Ser Ser Leu Leu Asp Arg Phe Leu Ala Thr Val
65                  70                  75                  80

AAG GCT CAT CCA AAA TAC TTG AGT TGT ATT GCA ATC AGC TGT TTT TTC     288
Lys Ala His Pro Lys Tyr Leu Ser Cys Ile Ala Ile Ser Cys Phe Phe
                85                  90                  95

CTA GCT GCC AAG ACT GTT GAG GAA GAT GAG AGA ATT CCA GTA CTA AAG     336
Leu Ala Ala Lys Thr Val Glu Glu Asp Glu Arg Ile Pro Val Leu Lys
            100                 105                 110

GTA TTG GCA AGA GAC AGT TTC TGT GGA TGT TCC TCA TCT GAA ATT TTG     384
Val Leu Ala Arg Asp Ser Phe Cys Gly Cys Ser Ser Ser Glu Ile Leu
        115                 120                 125

AGA ATG GAG AGA ATT ATT CTG GAT AAG TTG AAT TGG GAT CTT CAC ACA     432
Arg Met Glu Arg Ile Ile Leu Asp Lys Leu Asn Trp Asp Leu His Thr
    130                 135                 140

GCC ACA CCA TTG GAT TTT CTT CAT ATT TTC CAT GCC ATT GCA GTG TCA     480
Ala Thr Pro Leu Asp Phe Leu His Ile Phe His Ala Ile Ala Val Ser
145                 150                 155                 160

ACT AGG CCT CAG TTA CTT TTC AGT TTG CCC AAA TTG AGC CCA TCT CAA     528
Thr Arg Pro Gln Leu Leu Phe Ser Leu Pro Lys Leu Ser Pro Ser Gln
                165                 170                 175

CAT TTG GCA GTC CTT ACC AAG CAA CTA CTT CAC TGT ATG GCC TGC AAC     576
His Leu Ala Val Leu Thr Lys Gln Leu Leu His Cys Met Ala Cys Asn
            180                 185                 190
```

-continued

```
CAA CTT CTG CAA TTC AGA GGA TCC ATG CTT GCT CTG GCC ATG GTT AGT      624
Gln Leu Leu Gln Phe Arg Gly Ser Met Leu Ala Leu Ala Met Val Ser
            195                 200                 205

CTG GAA ATG GAG AAA CTC ATT CCT GAT TGG CTT TCT CTT ACA ATT GAA      672
Leu Glu Met Glu Lys Leu Ile Pro Asp Trp Leu Ser Leu Thr Ile Glu
        210                 215                 220

CTG CTT CAG AAA GCA CAG ATG GAT AGC TCC CAG TTG ATC CAT TGT CGG      720
Leu Leu Gln Lys Ala Gln Met Asp Ser Ser Gln Leu Ile His Cys Arg
225                 230                 235                 240

GAG CTT GTG GCA CAT CAC CTT TCT ACT CTG CAG TCT TCC CTG CCT CTG      768
Glu Leu Val Ala His His Leu Ser Thr Leu Gln Ser Ser Leu Pro Leu
                245                 250                 255

AAT TCC GTT TAT GTC TAC CGT CCC CTC AAG CAC ACC CTG GTG ACC TGT      816
Asn Ser Val Tyr Val Tyr Arg Pro Leu Lys His Thr Leu Val Thr Cys
            260                 265                 270

GAC AAA GGA GTG TTC AGA TTA CAT CCC TCC TCT GTC CCA GGC CCA GAC      864
Asp Lys Gly Val Phe Arg Leu His Pro Ser Ser Val Pro Gly Pro Asp
        275                 280                 285

TTC TCC AAG GAC AAC AGC AAG CCA GAA GTG CCA GTC AGA GGT ACA GCA      912
Phe Ser Lys Asp Asn Ser Lys Pro Glu Val Pro Val Arg Gly Thr Ala
290                 295                 300

GCC TTT TAC CAT CAT CTC CCA GCT GCC AGT GGG TGC AAG CAG ACC TCT      960
Ala Phe Tyr His His Leu Pro Ala Ala Ser Gly Cys Lys Gln Thr Ser
305                 310                 315                 320

ACT AAA CGC AAA GTA GAG GAA ATG GAA GTG GAT GAC TTC TAT GAT GGA     1008
Thr Lys Arg Lys Val Glu Glu Met Glu Val Asp Asp Phe Tyr Asp Gly
                325                 330                 335

ATC AAA CGG CTC TAT AAT GAA GAT AAT GTC TCA GAA AAT GTG GGT TCT     1056
Ile Lys Arg Leu Tyr Asn Glu Asp Asn Val Ser Glu Asn Val Gly Ser
            340                 345                 350

GTG TGT GGC ACT GAT TTA TCA AGA CAA GAG GGA CAT GCT TCC CCT TGT     1104
Val Cys Gly Thr Asp Leu Ser Arg Gln Glu Gly His Ala Ser Pro Cys
        355                 360                 365

CCA CCT TTG CAG CCT GTT TCT GTC ATG TAGTTTCAAC AAGTGCTACC TTTGAGT   1158
Pro Pro Leu Gln Pro Val Ser Val Met
370                 375

GTAAACTAAG GTAGACTACT TTGGGAATGA GAACATCCAA AATCAGGAAA GGCTGTAGAA  1218

GGAAATATAC CTTAACAGGC TGATTTGGAG TGACCCAGAA AA                    1260
```

(2) INFORMATION FOR SEQ ID NO:6:

(i) SEQUENCE CHARACTERISTICS:
        (A) LENGTH: 377 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:6:

```
Met Lys Phe Pro Gly Pro Leu Glu Asn Gln Arg Leu Ser Phe Leu Leu
1               5                   10                  15

Glu Lys Ala Ile Thr Arg Glu Ala Gln Met Trp Lys Val Asn Val Arg
            20                  25                  30

Lys Met Pro Ser Asn Gln Asn Val Ser Pro Ser Gln Arg Asp Glu Val
        35                  40                  45

Ile Gln Trp Leu Ala Lys Leu Lys Tyr Gln Phe Asn Leu Tyr Pro Glu
    50                  55                  60

Thr Phe Ala Leu Ala Ser Ser Leu Leu Asp Arg Phe Leu Ala Thr Val
```

```
                65                  70                  75                  80
Lys Ala His Pro Lys Tyr Leu Ser Cys Ile Ala Ile Ser Cys Phe Phe
                    85                  90                  95

Leu Ala Ala Lys Thr Val Glu Glu Asp Glu Arg Ile Pro Val Leu Lys
                100                 105                 110

Val Leu Ala Arg Asp Ser Phe Cys Gly Cys Ser Ser Glu Ile Leu
                115                 120                 125

Arg Met Glu Arg Ile Ile Leu Asp Lys Leu Asn Trp Asp Leu His Thr
            130                 135                 140

Ala Thr Pro Leu Asp Phe Leu His Ile Phe His Ala Ile Ala Val Ser
145                 150                 155                 160

Thr Arg Pro Gln Leu Leu Phe Ser Leu Pro Lys Leu Ser Pro Ser Gln
                165                 170                 175

His Leu Ala Val Leu Thr Lys Gln Leu Leu His Cys Met Ala Cys Asn
                180                 185                 190

Gln Leu Leu Gln Phe Arg Gly Ser Met Leu Ala Leu Ala Met Val Ser
            195                 200                 205

Leu Glu Met Glu Lys Leu Ile Pro Asp Trp Leu Ser Leu Thr Ile Glu
    210                 215                 220

Leu Leu Gln Lys Ala Gln Met Asp Ser Ser Gln Leu Ile His Cys Arg
225                 230                 235                 240

Glu Leu Val Ala His His Leu Ser Thr Leu Gln Ser Ser Leu Pro Leu
                245                 250                 255

Asn Ser Val Tyr Val Tyr Arg Pro Leu Lys His Thr Leu Val Thr Cys
                260                 265                 270

Asp Lys Gly Val Phe Arg Leu His Pro Ser Ser Val Pro Gly Pro Asp
            275                 280                 285

Phe Ser Lys Asp Asn Ser Lys Pro Glu Val Pro Val Arg Gly Thr Ala
    290                 295                 300

Ala Phe Tyr His His Leu Pro Ala Ala Ser Gly Cys Lys Gln Thr Ser
305                 310                 315                 320

Thr Lys Arg Lys Val Glu Glu Met Glu Val Asp Asp Phe Tyr Asp Gly
                325                 330                 335

Ile Lys Arg Leu Tyr Asn Glu Asp Asn Val Ser Glu Asn Val Gly Ser
                340                 345                 350

Val Cys Gly Thr Asp Leu Ser Arg Gln Glu Gly His Ala Ser Pro Cys
            355                 360                 365

Pro Pro Leu Gln Pro Val Ser Val Met
    370                 375

(2) INFORMATION FOR SEQ ID NO:7:

(i) SEQUENCE CHARACTERISTICS:
        (A) LENGTH: 797 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 75...386
        (D) OTHER INFORMATION:

(xi) SEQUENCE DESCRIPTION: SEQ ID NO:7:

GGCACGAGGT TGTAGTTAAG CTCGTGTAAC GGCGGCGGTG TCGGTAGCTG CTGTAGCGAA     60
```

```
GAGAGTTTGG CGCG ATG TCT CAC ACC ATT TTG CTG GTA CAG CCT ACC AAG    110
               Met Ser His Thr Ile Leu Leu Val Gln Pro Thr Lys
                 1               5                  10

AGG CCA GAA GGC AGA ACT TAT GCT GAC TAC GAA TCT GTG AAT GAA TGC    158
Arg Pro Glu Gly Arg Thr Tyr Ala Asp Tyr Glu Ser Val Asn Glu Cys
         15                  20                  25

ATG GAA GGT GTT TGT AAA ATG TAT GAA GAA CAT CTG AAA AGA ATG AAT    206
Met Glu Gly Val Cys Lys Met Tyr Glu Glu His Leu Lys Arg Met Asn
     30                  35                  40

CCC AAC AGT CCC TCT ATC ACA TAT GAC ATC AGT CAG TTG TTT GAT TTC    254
Pro Asn Ser Pro Ser Ile Thr Tyr Asp Ile Ser Gln Leu Phe Asp Phe
 45                  50                  55                  60

ATC GAT GAT CTG GCA GAC CTC AGC TGC CTG GTT TAC CGA GCT GAT ACC    302
Ile Asp Asp Leu Ala Asp Leu Ser Cys Leu Val Tyr Arg Ala Asp Thr
             65                  70                  75

CAG ACA TAC CAG CCT TAT AAC AAA GAC TGG ATT AAA GAG AAG ATC TAC    350
Gln Thr Tyr Gln Pro Tyr Asn Lys Asp Trp Ile Lys Glu Lys Ile Tyr
                 80                  85                  90

GTG CTC CTT CGT CGG CAG GCC CAA CAG GCT GGG AAA TAATTGTGTT GGAAGC  402
Val Leu Leu Arg Arg Gln Ala Gln Gln Ala Gly Lys
             95                  100

ACTGGGGGGG TTGGGGTGGG CTTGGAACAC AGGTGTGTAC AGCGTGCTGT AGTGGAAGTT  462

TTGTATCATA GTAATCCTGT TTCCACTTTG TTATACTCTA GCCAAGATTG ACTGTATTAG  522

ATGAAATGTG AGGATCTTGT TCAATCGGAA ACCCCCGTTA CCTCCTCTTT TTCTTTCTCT  582

TTCTTTTTTT TTTTTTACTT AAACATTTTT ATGATGATTT AGATGGAAGT TGTTCTTCGT  642

CACTTAATGT TGGTTCCAGT CCTTCAACTG TTCATATCTA CTTTATAACA TTCACATACT  702

AACCCTTCTG GGGTTCAAGA TGGGGGGTGG CAAATGCAGT TTAGCCATGT CCTCAAGATA  762

AAGTCTTGGT AAAAATAAAT AAATGTCCTT TAGTT                            797
```

(2) INFORMATION FOR SEQ ID NO:8:

(i) SEQUENCE CHARACTERISTICS:
        (A) LENGTH: 104 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:8:

```
Met Ser His Thr Ile Leu Leu Val Gln Pro Thr Lys Arg Pro Glu Gly
 1               5                  10                  15

Arg Thr Tyr Ala Asp Tyr Glu Ser Val Asn Glu Cys Met Glu Gly Val
             20                  25                  30

Cys Lys Met Tyr Glu Glu His Leu Lys Arg Met Asn Pro Asn Ser Pro
         35                  40                  45

Ser Ile Thr Tyr Asp Ile Ser Gln Leu Phe Asp Phe Ile Asp Asp Leu
 50                  55                  60

Ala Asp Leu Ser Cys Leu Val Tyr Arg Ala Asp Thr Gln Thr Tyr Gln
 65                  70                  75                  80

Pro Tyr Asn Lys Asp Trp Ile Lys Glu Lys Ile Tyr Val Leu Leu Arg
                 85                  90                  95

Arg Gln Ala Gln Gln Ala Gly Lys
            100
```

(2) INFORMATION FOR SEQ ID NO:9:

(i) SEQUENCE CHARACTERISTICS:
    (A) LENGTH: 2399 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:9:

```
GGAAGATGGC GGCTGTGGTG GAGAATGTAG TGAAGCTCCT TGGGGAGCAG TACTACAAAG      60

ATGCCATGGA GCAGTGCCAC AATTACAATG CTCGCCTCTG TGCTGAGCGC AGCGTGCGCC     120

TGCCTTTCTT GGACTCACAG ACCGGAGTAG CCCAGAGCAA TTGTTACATC TGGATGGAAA     180

AGCGACACCG GGGTCCAGGA TTGGCCTCCG GACAGCTGTA CTCCTACCCT GCCCGGCGCT     240

GGCGGAAAAA GCGGCGAGCC CATCCCCCTG AGGATCCACG ACTTTCCTTC CCATCTATTA     300

AGCCAGACAC AGACCAGACC CTGAAGAAGG AGGGGCTGAT CTCTCAGGAT GGCAGTAGTT     360

TAGAGGCTCT GTTGCGCACT GACCCCCTGG AGAAGCGAGG TGCCCCGGAT CCCCGAGTTG     420

ATGATGACAG CCTGGGCGAG TTTCCTGTGA CCAACAGTCG AGCGCGAAAG CGGATCCTAG     480

AACCAGATGA CTTCCTGGAT GACCTCGATG ATGAAGACTA TGAAGAAGAT ACTCCCAAGC     540

GTCGGGGAAA GGGGAAATCC AAGGGTAAGG GTGTGGGCAG TGCCCGTAAG AAGCTGGATG     600

CTTCCATCCT GGAGGACCGG GATAAGCCCT ATGCCTGTGA CATTTGTGGA AAACGTTACA     660

AGAACCGACC AGGCCTCAGT TACCACTATG CCCACTCCCA CTTGGCTGAG GAGGAGGGCG     720

AGGACAAGGA AGACTCTCAA CCACCCACTC CTGTTTCCCA GAGGTCTGAG GAGCAGAAAT     780

CCAAAAAGGG TCCTGATGGA TTGGCCTTGC CCAACAACTA CTGTGACTTC TGCCTGGGGG     840

ACTCAAAGAT TAACAAGAAG ACGGGACAAC CCGAGGAGCT GGTGTCTTGT TCTGACTGTG     900

GCCGCTCAGG GCATCCATCT TGCCTCCAAT TTACCCCCGT GATGATGGCG GCAGTGAAGA     960

CATACCGCTG GCAGTGCATC GAGTGCAAAT GTTGCAATAT CTGCGGCACC TCCGAGAATG    1020

ACGACCAGTT GCTCTTCTGT GATGACTGCG ATCGTGGCTA CCACATGTAC TGTCTCACCC    1080

CGTCCATGTC TGAGCCCCCT GAAGGAAGTT GGAGCTGCCA CCTGTGTCTG GACCTGTTGA    1140

AAGAGAAAGC TTCCATCTAC CAGAACCAGA ACTCCTCTTG ATGTGGCCAC CCACCTGCTC    1200

CCCGACATAT CTAAGGCTGT TTCTCTCCTC CACTTCATAT TTCATACCCA TCTTTCCCTT    1260

CTTCCTCCTC TCCTTCACAA ATCCAGAGAA CCTTGGGGTG GTTGTGCCAG CCTGCCTTTG    1320

GCAGCTGCAA GCTGAGGTGG CAGCTCTGAC CACCTCTGGC CCCAGGCCTC AGGGAGAAAG    1380

GAGCAACACA CTGCCCCTAG GCGTGCGTGT GGCCCAGTTT CTCTCTGCTC TCCATTAAGT    1440

GCATTCACTC TGCTTGCCTT GGGCCCAGCC CCTGGTGATC ACAGGGTTCA AACAGTGTCC    1500

TCCTAGAAAG AGTGGGAGAG CAGCTCACTT CTCTGTGTTC TGCCTCCCCT CTGGTCTCCA    1560

GAGTTTTCCT GTCCTCTAGA GGCAAGCCAG GCCAGGGAGC TGGGAGCGAG CAAGCTGAGG    1620

CCACGTCCAC AAGGAGCTTT TCATGCCCCT GTGCCGCATA GCCTCACCTC TTTCCTCCAG    1680

AGTGGCTCTC TGCGGCCCTG TGTTCCTGCT ACAGAGTGTT CTTTTCTGGA GTCAGGATGT    1740

TCTCGGTCAC CCTCCTGGTT CTGCCCTGTC CCATTCCACC CCACCCCAGG GGGAACAGTA    1800

GCTTCACCTT GTTATTCCCA TTGCTCTCCT GGCTCACTCT TACGGTCGGT CTCCAGTGAC    1860

TGAAGCATTC CCCACCCTTG GAATTTCTCA TCTTCTGCCT CCCTTCCTAC TCCTTTTGGT    1920

TTTGTGGGGA GAGGGGAAGG ATCAGGGGGC AAGGCCAGCA GCTCGGGGGC CACAAGGAGA    1980

TGGATAATGT GCCTGTTTTT TAACACAACA AAAAGCCTA CCTCCAAAAT CCCCTTTTTG    2040

TTCTTCCTGG ACCTGGGCAT TCAGCCTCCT GCTCTTAACT GAATTGGGAG CCTCTGCCAC    2100
```

```
CTGCCCCGTG TATCCTGGCT CTCAGCTCAT GGGGAAGCCA CATAGACATC CCTTTCTTCC   2160

CTTGCACGCT CGCTAGCAGC TGGTAGGTCT TCACACCCTG ATTCCTCAAG TTTTCTGCTT   2220

AGTGGCACTG ACATTAAGTA GTGGGGGGAC AGTCCATGCC AGGACACCCT GGAGTAGCCT   2280

TCCCCCTTGG CCGTGGGCAG GCCCTAACTC ACTGTCGCTT TGGAGTTGAG GTGTCTTTTT   2340

TTTTTCTTTC TTTAGTTCCT GTATTCTAAA CATTAGTAAA AATAAATGTT TTTACACAG    2399
```

(2) INFORMATION FOR SEQ ID NO:10:

(i) SEQUENCE CHARACTERISTICS:
        (A) LENGTH: 843 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 1...840
        (D) OTHER INFORMATION:

(xi) SEQUENCE DESCRIPTION: SEQ ID NO:10:

```
ATG GCG GCT GTG GTG GAG AAT GTA GTG AAG CTC CTT GGG GAG CAG TAC      48
Met Ala Ala Val Val Glu Asn Val Val Lys Leu Leu Gly Glu Gln Tyr
1               5                   10                  15

TAC AAA GAT GCC ATG GAG CAG TGC CAC AAT TAC AAT GCT CGC CTC TGT      96
Tyr Lys Asp Ala Met Glu Gln Cys His Asn Tyr Asn Ala Arg Leu Cys
                20                  25                  30

GCT GAG CGC AGC GTG CGC CTG CCT TTC TTG GAC TCA CAG ACC GGA GTA     144
Ala Glu Arg Ser Val Arg Leu Pro Phe Leu Asp Ser Gln Thr Gly Val
            35                  40                  45

GCC CAG AGC AAT TGT TAC ATC TGG ATG GAA AAG CGA CAC CGG GGT CCA     192
Ala Gln Ser Asn Cys Tyr Ile Trp Met Glu Lys Arg His Arg Gly Pro
        50                  55                  60

GGA TTG GCC TCC GGA CAG CTG TAC TCC TAC CCT GCC CGG CGC TGG CGG     240
Gly Leu Ala Ser Gly Gln Leu Tyr Ser Tyr Pro Ala Arg Arg Trp Arg
65                  70                  75                  80

AAA AAG CGG CGA GCC CAT CCC CCT GAG GAT CCA CGA CTT TCC TTC CCA     288
Lys Lys Arg Arg Ala His Pro Pro Glu Asp Pro Arg Leu Ser Phe Pro
                85                  90                  95

TCT ATT AAG CCA GAC ACA GAC CAG ACC CTG AAG AAG GAG GGG CTG ATC     336
Ser Ile Lys Pro Asp Thr Asp Gln Thr Leu Lys Lys Glu Gly Leu Ile
                100                 105                 110

TCT CAG GAT GGC AGT AGT TTA GAG GCT CTG TTG CGC ACT GAC CCC CTG     384
Ser Gln Asp Gly Ser Ser Leu Glu Ala Leu Leu Arg Thr Asp Pro Leu
            115                 120                 125

GAG AAG CGA GGT GCC CCG GAT CCC CGA GTT GAT GAT GAC AGC CTG GGC     432
Glu Lys Arg Gly Ala Pro Asp Pro Arg Val Asp Asp Asp Ser Leu Gly
        130                 135                 140

GAG TTT CCT GTG ACC AAC AGT CGA GCG CGA AAG CGG ATC CTA GAA CCA     480
Glu Phe Pro Val Thr Asn Ser Arg Ala Arg Lys Arg Ile Leu Glu Pro
145                 150                 155                 160

GAT GAC TTC CTG GAT GAC CTC GAT GAT GAA GAC TAT GAA GAA GAT ACT     528
Asp Asp Phe Leu Asp Asp Leu Asp Asp Glu Asp Tyr Glu Glu Asp Thr
                165                 170                 175

CCC AAG CGT CGG GGA AAG GGG AAA TCC AAG GAG GCA AGC CAG GCC AGG     576
Pro Lys Arg Arg Gly Lys Gly Lys Ser Lys Glu Ala Ser Gln Ala Arg
                180                 185                 190

GAG CTG GGA GCG AGC AAG CTG AGG CCA CGT CCA CAA GGA GCT TTT CAT     624
Glu Leu Gly Ala Ser Lys Leu Arg Pro Arg Pro Gln Gly Ala Phe His
```

```
                195                     200                     205
GCC CCT GTG CCG CAT AGC CTC ACC TCT TTC CTC CAG AGT GGC TCT CTG         672
Ala Pro Val Pro His Ser Leu Thr Ser Phe Leu Gln Ser Gly Ser Leu
    210                     215                     220

CGG CCC TGT GTT CCT GCT ACA GAG TGT TCT TTT CTG GAG TCA GGA TGT         720
Arg Pro Cys Val Pro Ala Thr Glu Cys Ser Phe Leu Glu Ser Gly Cys
225                     230                     235                     240

TCT CGG TCA CCC TCC TGG TTC TGC CCT GTC CCA TTC CAC CCC ACC CCA         768
Ser Arg Ser Pro Ser Trp Phe Cys Pro Val Pro Phe His Pro Thr Pro
                245                     250                     255

GGG GGA ACA GTA GCT TCA CCT TGT TAT TCC CAT TGC TCT CCT GGC TCA         816
Gly Gly Thr Val Ala Ser Pro Cys Tyr Ser His Cys Ser Pro Gly Ser
                260                     265                     270

CTC TTA CGG TCG GTC TCC AGT GAC TGA                                     843
Leu Leu Arg Ser Val Ser Ser Asp
            275                 280

(2) INFORMATION FOR SEQ ID NO:11:

(i) SEQUENCE CHARACTERISTICS:
         (A) LENGTH: 280 amino acids
         (B) TYPE: amino acid
         (C) STRANDEDNESS:
         (D) TOPOLOGY: unknown (ii) MOLECULE TYPE: protein (xi) SEQUENCE DESCRIPTION: SEQ ID NO:11:

Met Ala Ala Val Val Glu Asn Val Val Lys Leu Leu Gly Glu Gln Tyr
1               5                   10                  15

Tyr Lys Asp Ala Met Glu Gln Cys His Asn Tyr Asn Ala Arg Leu Cys
                20                  25                  30

Ala Glu Arg Ser Val Arg Leu Pro Phe Leu Asp Ser Gln Thr Gly Val
            35                  40                  45

Ala Gln Ser Asn Cys Tyr Ile Trp Met Glu Lys Arg His Arg Gly Pro
        50                  55                  60

Gly Leu Ala Ser Gly Gln Leu Tyr Ser Tyr Pro Ala Arg Arg Trp Arg
65                  70                  75                  80

Lys Lys Arg Arg Ala His Pro Pro Glu Asp Pro Arg Leu Ser Phe Pro
                85                  90                  95

Ser Ile Lys Pro Asp Thr Asp Gln Thr Leu Lys Lys Glu Gly Leu Ile
                100                 105                 110

Ser Gln Asp Gly Ser Ser Leu Glu Ala Leu Leu Arg Thr Asp Pro Leu
            115                 120                 125

Glu Lys Arg Gly Ala Pro Asp Pro Arg Val Asp Asp Asp Ser Leu Gly
        130                 135                 140

Glu Phe Pro Val Thr Asn Ser Arg Ala Arg Lys Arg Ile Leu Glu Pro
145                 150                 155                 160

Asp Asp Phe Leu Asp Asp Leu Asp Asp Glu Asp Tyr Glu Glu Asp Thr
                165                 170                 175

Pro Lys Arg Arg Gly Lys Gly Lys Ser Lys Glu Ala Ser Gln Ala Arg
            180                 185                 190

Glu Leu Gly Ala Ser Lys Leu Arg Pro Arg Pro Gln Gly Ala Phe His
        195                 200                 205

Ala Pro Val Pro His Ser Leu Thr Ser Phe Leu Gln Ser Gly Ser Leu
    210                     215                     220

Arg Pro Cys Val Pro Ala Thr Glu Cys Ser Phe Leu Glu Ser Gly Cys
225                     230                     235                     240
```

```
Ser Arg Ser Pro Ser Trp Phe Cys Pro Val Pro Phe His Pro Thr Pro
            245                 250                 255

Gly Gly Thr Val Ala Ser Pro Cys Tyr Ser His Cys Ser Pro Gly Ser
            260                 265                 270

Leu Leu Arg Ser Val Ser Ser Asp
            275             280

(2) INFORMATION FOR SEQ ID NO:12:

(i) SEQUENCE CHARACTERISTICS:
        (A) LENGTH: 633 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: Coding Sequence
         (B) LOCATION: 1...630
         (D) OTHER INFORMATION:

(xi) SEQUENCE DESCRIPTION: SEQ ID NO:12:
```

| | | | | | | | | | | | | | | | | |
|---|---|---|---|---|---|---|---|---|---|---|---|---|---|---|---|---|
| ATG | GCG | GCT | GTG | GTG | GAG | AAT | GTA | GTG | AAG | CTC | CTT | GGG | GAG | CAG | TAC | 48 |
| Met | Ala | Ala | Val | Val | Glu | Asn | Val | Val | Lys | Leu | Leu | Gly | Glu | Gln | Tyr | |
| 1 | | | | 5 | | | | | 10 | | | | | 15 | | |
| TAC | AAA | GAT | GCC | ATG | GAG | CAG | TGC | CAC | AAT | TAC | AAT | GCT | CGC | CTC | TGT | 96 |
| Tyr | Lys | Asp | Ala | Met | Glu | Gln | Cys | His | Asn | Tyr | Asn | Ala | Arg | Leu | Cys | |
| | | | 20 | | | | | 25 | | | | | 30 | | | |
| GCT | GAG | CGC | AGC | GTG | CGC | CTG | CCT | TTC | TTG | GAC | TCA | CAG | ACC | GGA | GTA | 144 |
| Ala | Glu | Arg | Ser | Val | Arg | Leu | Pro | Phe | Leu | Asp | Ser | Gln | Thr | Gly | Val | |
| | | 35 | | | | | 40 | | | | | 45 | | | | |
| GCC | CAG | AGC | AAT | TGT | TAC | ATC | TGG | ATG | GAA | AAG | CGA | CAC | CGG | GGT | CCA | 192 |
| Ala | Gln | Ser | Asn | Cys | Tyr | Ile | Trp | Met | Glu | Lys | Arg | His | Arg | Gly | Pro | |
| | 50 | | | | | 55 | | | | | 60 | | | | | |
| GGA | TTG | GCC | TCC | GGA | CAG | CTG | TAC | TCC | TAC | CCT | GCC | CGG | CGC | TGG | CGG | 240 |
| Gly | Leu | Ala | Ser | Gly | Gln | Leu | Tyr | Ser | Tyr | Pro | Ala | Arg | Arg | Trp | Arg | |
| 65 | | | | | 70 | | | | | 75 | | | | | 80 | |
| AAA | AAG | CGG | CGA | GCC | CAT | CCC | CCT | GAG | GAT | CCA | CGA | CTT | TCC | TTC | CCA | 288 |
| Lys | Lys | Arg | Arg | Ala | His | Pro | Pro | Glu | Asp | Pro | Arg | Leu | Ser | Phe | Pro | |
| | | | | 85 | | | | | 90 | | | | | 95 | | |
| TCT | ATT | AAG | CCA | GAC | ACA | GAC | CAG | ACC | CTG | AAG | AAG | GAG | GGG | CTG | ATC | 336 |
| Ser | Ile | Lys | Pro | Asp | Thr | Asp | Gln | Thr | Leu | Lys | Lys | Glu | Gly | Leu | Ile | |
| | | | 100 | | | | | 105 | | | | | 110 | | | |
| TCT | CAG | GAT | GGC | AGT | AGT | TTA | GAG | GCT | CTG | TTG | CGC | ACT | GAC | CCC | CTG | 384 |
| Ser | Gln | Asp | Gly | Ser | Ser | Leu | Glu | Ala | Leu | Leu | Arg | Thr | Asp | Pro | Leu | |
| | | 115 | | | | | 120 | | | | | 125 | | | | |
| GAG | AAG | CGA | GGT | GCC | CCG | GAT | CCC | CGA | GTT | GAT | GAT | GAC | AGC | CTG | GGC | 432 |
| Glu | Lys | Arg | Gly | Ala | Pro | Asp | Pro | Arg | Val | Asp | Asp | Asp | Ser | Leu | Gly | |
| | 130 | | | | | 135 | | | | | 140 | | | | | |
| GAG | TTT | CCT | GTG | ACC | AAC | AGT | CGA | GCG | CGA | AAG | CGG | ATC | CTA | GAA | CCA | 480 |
| Glu | Phe | Pro | Val | Thr | Asn | Ser | Arg | Ala | Arg | Lys | Arg | Ile | Leu | Glu | Pro | |
| 145 | | | | | 150 | | | | | 155 | | | | | 160 | |
| GAT | GAC | TTC | CTG | GAT | GAC | CTC | GAT | GAT | GAA | GAC | TAT | GAA | GAA | GAT | ACT | 528 |
| Asp | Asp | Phe | Leu | Asp | Asp | Leu | Asp | Asp | Glu | Asp | Tyr | Glu | Glu | Asp | Thr | |
| | | | | 165 | | | | | 170 | | | | | 175 | | |
| CCC | AAG | CGT | CGG | GGA | AAG | GGG | AAA | TCC | AAG | GGG | GGA | ACA | GTA | GCT | TCA | 576 |
| Pro | Lys | Arg | Arg | Gly | Lys | Gly | Lys | Ser | Lys | Gly | Gly | Thr | Val | Ala | Ser | |
| | | | 180 | | | | | 185 | | | | | 190 | | | |
| CCT | TGT | TAT | TCC | CAT | TGC | TCT | CCT | GGC | TCA | CTC | TTA | CGG | TCG | GTC | TCC | 624 |
| Pro | Cys | Tyr | Ser | His | Cys | Ser | Pro | Gly | Ser | Leu | Leu | Arg | Ser | Val | Ser | |
| | | 195 | | | | | 200 | | | | | 205 | | | | |

```
AGT GAC TGA                                                              633
Ser Asp
    210
```

(2) INFORMATION FOR SEQ ID NO:13:

(i) SEQUENCE CHARACTERISTICS:
        (A) LENGTH: 210 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:13:

```
Met Ala Ala Val Val Glu Asn Val Val Lys Leu Leu Gly Glu Gln Tyr
  1               5                  10                  15

Tyr Lys Asp Ala Met Glu Gln Cys His Asn Tyr Asn Ala Arg Leu Cys
                 20                  25                  30

Ala Glu Arg Ser Val Arg Leu Pro Phe Leu Asp Ser Gln Thr Gly Val
             35                  40                  45

Ala Gln Ser Asn Cys Tyr Ile Trp Met Glu Lys Arg His Arg Gly Pro
         50                  55                  60

Gly Leu Ala Ser Gly Gln Leu Tyr Ser Tyr Pro Ala Arg Arg Trp Arg
 65                  70                  75                  80

Lys Lys Arg Arg Ala His Pro Pro Glu Asp Pro Arg Leu Ser Phe Pro
                 85                  90                  95

Ser Ile Lys Pro Asp Thr Asp Gln Thr Leu Lys Lys Glu Gly Leu Ile
                100                 105                 110

Ser Gln Asp Gly Ser Ser Leu Glu Ala Leu Leu Arg Thr Asp Pro Leu
            115                 120                 125

Glu Lys Arg Gly Ala Pro Asp Pro Arg Val Asp Asp Asp Ser Leu Gly
        130                 135                 140

Glu Phe Pro Val Thr Asn Ser Arg Ala Arg Lys Arg Ile Leu Glu Pro
145                 150                 155                 160

Asp Asp Phe Leu Asp Asp Leu Asp Asp Glu Asp Tyr Glu Glu Asp Thr
                165                 170                 175

Pro Lys Arg Arg Gly Lys Gly Lys Ser Lys Gly Gly Thr Val Ala Ser
                180                 185                 190

Pro Cys Tyr Ser His Cys Ser Pro Gly Ser Leu Leu Arg Ser Val Ser
            195                 200                 205

Ser Asp
    210
```

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

```
GATGCAGAAT TCCGACATGA CTCAG                                               25
```

(2) INFORMATION FOR SEQ ID NO:15:

(i) SEQUENCE CHARACTERISTICS:

-continued

```
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

ATGGTGGGCG GTGTTGTCAT AGCG                                              24
```

HSREQ*1 AND HSREQ*2 PROTEINS AND USE THEREOF TO DETECT CDK2

RELATED APPLICATIONS

This application is a divisional application under 37 CFR §1.53(b) of U.S. Ser. No. 08/969,106, filed on Nov. 13, 1997, now U.S. Pat. No. 5,986,055, incorporated herein by reference.

This invention was made with United States Government support under award number 70NANB5H1066 awarded by the National Institute of Standards and Technology. The United States Government has certain rights in the invention.

1. FIELD OF THE INVENTION

The present invention relates to complexes of CDK2 protein with other proteins, in particular, complexes of CDK2 with cyclin H, CDK2 with cyclin I, CDK2 with ERH, CDK2 with hsReq*-1, and CDK2 with hsReq*-2 proteins. The invention includes antibodies to CDK2 complexes, and their use in, inter alia, screening, diagnosis, prognosis and therapy. The invention further relates to the hsReq*-1 and hsReq*-2 genes and proteins and derivatives, fragments and analogs, thereof.

2. BACKGROUND OF THE INVENTION

2.1 CDK2

Human cyclin-dependent kinase 2 or cell division kinase (CDK2; GenBank Accession No. X61622; Elledge and Spottswood, 1991, EMBO J. 10: 2653–2659; Ninomiya-Tsuji et al., 1991, Proc. Natl. Acad. Sci. USA 88: 9006–9010) is a serine-threonine protein kinase of 298 amino acids that has approximately 65% amino acid identity to a second critical cell cycle regulator, p34cdc2, more commonly known as CDC2. CDK2 is expressed late in G1 or early in S phase, slightly before CDC2, and is pivotal for G1/S transition. CDK2 cannot complement yeast CDC2/CDC28 mutations under all the conditions that CDC2 can, indicating that the two kinases regulate the cell cycle at distinct stages.

CDK2 activity is dependent upon phosphorylation of threonine 160 by CDK-activating kinase (CAK), which occurs when CDK2 complexes with cyclins A and E. Conversely, CDK2 kinase activity is inactivated by dephosphorylation by human KAP (CDK-Associated Phosphatase; Poon and Hunter, 1995, Science 270: 90–93). In particular, competition between KAP and cyclin A determines the phosphorylation state of CDK2. CDK2 phosphorylates pRb, p53, transcription factor E2F, histone H1, and other proteins central to cell cycle control (Higashi et al., 1996, Eur. J. Biochem. 237: 460–467). Other proteins, including $p21^{cip}$, and $p27^{kip}$, complex with CDK2 to block its interaction with downstream substrates, as well as blocking CDK2 phosphorylation itself (Adams et al., 1996, Mol. Cell. Biol. 16: 6623–6633). The complex interplay of phase-specific cyclin expression, phosphorylation/dephosphorylation cascades, and other CDK2 interacting proteins such as $p21^{waf}$ and $p27^{kip}$, ultimately plays out through CDK2 activity to determine cell cycle progression.

Deregulation of CDK2 is strongly implicated in mechanisms of carcinogenesis and in the treatment of cancer. DNA tumor viruses transform cells by directly inhibiting Rb tumor-suppressing function (e.g., papilloma viruses and cervical cancer). The Rb then releases negative control of E2F. Normally, the inhibition of Rb is accomplished by phosphorylation of Rb by CDK2 (Nevins, 1992, Science 258: 424–429). CDK2 is implicated in the differentiation of glioma cells (Kokunai et al., 1997, J. Neuro-oncol. 32: 125–133). In human breast carcinoma cells, the anti-cancer agent flavopiridol induces G1 arrest by inhibition of both CDK2 and CDK4 (Carlson et al., 1996, Cancer Res. 56: 2973–2978). Anti-estrogens up-regulate CDK2 inhibitors $p21^{cip}$ and $p27^{kip}$, thus causing reduction in pRb phosphorylation, and decreased cell progression into S phase (Watts et al., 1995, Mol. Endocrinol. 9: 1804–1813). Serum-deprivation of vascular smooth muscle cells is associated with CDK2/$p27^{kip}$ complex formation, leading to inhibition of CDK2 enzymatic activity (Chen et al., 1997, J. Clin. Invest. 99: 2334–2341). Thus, along with regulation of cyclin A expression, CDK2 activity is the mechanism through which $p27^{kip}$ acts to inhibit intimal hyperplasia during atherosclerosis and re-stenosis.

To review, CDK2 is implicated in the control of cell cycle progression, transcriptional regulation via E2F, control of cellular differentiation, intracellular signal transduction involving phosphorylation, mechanisms of tumorigenesis, tumor progression and spread, and athero-sclerosis and re-stenosis via effects on intimal proliferation.

2.2 Cyclin H

Human cyclin H (GenBank Accession No. U11791; Makela et al., 1994, Nature 371: 254–257) is a 323 amino acid protein that complexes with CDK7 to form CDK-activating kinase (CAK; Fisher and Morgan, 1994, Cell 78: 713–724). CAK, in turn, phosphorylates CDK2, as well as various cyclin complexes of CDK2 and CDK4. Thus, like CDK2, cyclin H is centrally implicated in control of cell cycle progression. CAK is also associated with the mammalian transcription factor IIH (TFIIH), a multisubunit complex that is required for transcription and DNA nucleotide excision repair (Drapkin et al., 1996, Proc. Natl. Acad. Sci. USA 93: 6488–6493). Therefore, the role of cyclin H extends beyond cell cycle control to include coordination of the cell cycle with transcription and DNA repair. Dysfunction of TFIIH is implicated in various genetic disorders including xeroderma pigmentosum, Cockayne's syndrome and trichothiodystrophy (Seroz et al., 1995, Curr. Opin. Genet. Dev. 5: 217–222). In summary, cyclin H is implicated in the control of cell cycle progression, transcriptional control via TFIIH, DNA repair, and various genetic disorders associated with impaired DNA repair.

2.3 Cyclin I

Cyclin I (GenBank Accession No. D50310; Nakamura et al., 1995, Exp. Cell Res. 221: 534–542), in contrast to other cyclin proteins, is widely expressed in many post-mitotic tissues at constant levels throughout the cell cycle. The protein contains a typical cyclin box near the N-terminus, implicating it in control of cell cycle progression and transcriptional control (Gibson et al., 1994, Nucleic Acids Res. 22: 946–952). It also has a PEST domain proximal to its C-terminus; thus, it may be the target of rapid inactivation via ubiquitin-based proteolysis, as are most transcription factors (Rechsteiner, 1990, Semin. Cell Biol. 1: 433–440).

2.4 ERH

A human cDNA (GenBank Accession No. D85785; Isomura et al., 1996) encoding a 104 amino acid protein termed ERH, homologous to DROER, the enhancer of the rudimentary gene in *Drosophila melanogaster*, was found to interact with CDK2. In Drosophila, the gene product is required for transcriptional regulation of the rudimentary gene. The enzyme functions in the pyrimidine metabolic pathway, and has a critical role in wing development. ERH is thus implicated in transcriptional control, DNA pyrimidine metabolism, and in development.

2.5 hsREQ*-1 AND hsREQ*-2

Two sequences were identified as CDK2 interactants which are identical to sequences within the human homolog of the mouse zinc finger protein Requiem (hsReq; GenBank Accession No. U94585; Gabig et al., 1994, J. Biol. Chem. 269: 29515–29519). HsReq is hypothesized to encode a transcription factor required for apoptosis following survival factor withdrawal from myeloid cells and to function as a tumor suppressor. However, as described infra, these hsReq regions identified as encoding a protein that interacts with CDK2 must occur with a splice variant of hsReq containing amino acids encoded by a nucleotide sequence of the 3' untranslated region of the hsReq mRNA, which was identified as encoding a CDK2 interacting protein. Two such splice variants are described in Section 5.2, and are referred to as hsReq*-1 and hsReq*-2.

CDK2 complexes with any of cyclin H, cyclin I, ERH, hsReq*-1 or hsReq*-2 have not been previously described.

Citation of a reference herein shall not be construed as an admission that such is prior art to the present invention.

3. SUMMARY OF THE INVENTION

The present invention provides compositions and methods of production of protein complexes of CDK2 with proteins that interact with (i.e. bind to) CDK2 (the proteins shown to bind with CDK2 are designated "CDK2-IP" for CDK2 interacting protein, and a complex of CDK2 and a CDK2-IP is designated as CDK2:CDK2-IP herein). Specifically, the invention relates to complexes of CDK2, and derivatives, fragments and analogs of CDK2 with cyclin H. with cyclin I, with ERH, with hsReq*-1 and with hsReq*-2, and their derivatives, analogs and fragments.

In their screen for proteins that interact with CDK2, the present inventors have identified novel proteins, hsReq*-1 and hsReq*-2, which are encoded by mRNA splice variants of the hsReq gene, i.e., the mRNAs encoding hsReq*-1 and hsReq*-2 are generated by RNA splicing at splice sites other than the splice sites used to process the mRNA encoding hsReq. Accordingly, the invention further relates to nucleotide sequences of hsReq*-1 and hsReq*-2 (human hsReq*-1 and hsReq*-2 genes and homologs of other species), as well as derivatives (e.g., fragments) and analogs thereof. Nucleic acids able to hybridize to or complementary to the foregoing nucleotide sequence, such as the inverse complement (i.e., has the complementary sequence running in reverse orientation to the strand so that the inverse complement would hybridize without mismatches to the nucleic acid strand; thus, for example, where the coding strand is hybridizable to a nucleic acid sequence with no mismatches between the coding strand and the hybridizable strand, then the inverse complement of the hybridizable strand is identical to the coding strand) of the foregoing sequences are provided. In particular, the invention provides nucleic acids that comprise, as well as nucleic acids (e.g., the inverse complement) that are hybridizable to or complementary to, at least a 5, 10, or 25 nucleotide portion of the nucleotide sequences encoding hsReq*-1 and hsReq*-2 that span the alternate splice junctions of the hsReq*-1 and hsReq*-2 mRNAs (i.e. the point in the hsReq*-1 or hsReq*-2 nucleotide sequence at which the 5' and 3' splice sites were joined in processing the hsReq*-1 or hsReq*-2 mRNA). The invention also relates to hsReq*-1 and hsReq*-2 derivatives and analogs that are functionally active, i.e., they are capable of displaying one or more known functional activities of a wild-type hsReq*-1 or hsReq*-2 protein. Such functional activities include, but are not limited to the ability to bind with [or compete for binding with] CDK2, antigenicity [ability to bind (or compete with hsReq*-1 or hsReq*-2 for binding) to an anti-hsReq*-1 or anti-hsReq*-2 antibody, respectively], and immunogenicity (ability to generate an antibody that binds hsReq*-1 or hsReq*-2, respectively). Specific embodiments relate to fragments, or derivatives or analogs thereof, comprising all or a portion of amino acids 187 to 280 of the hsReq*-1 amino acid sequence as depicted in FIG. 6 (SEQ ID NO:11) and comprising all or a portion of amino acids 188 to 210 of the hsReq*-2 amino acid sequence as depicted in FIG. 7 (SEQ ID NO:13).

Methods of production of the CDK2:CDK2-IP complexes and of hsReq*-1 and hsReq*-2 proteins, and derivatives and analogs of the complexes and proteins, e.g., by recombinant means, are also provided. Pharmaceutical compositions are also provided.

The invention further provides methods of modulating (i.e., inhibiting or enhancing) the activity of CDK2:CDK2-IP complexes, particularly CDK2:cyclin H, CDK2:cyclin I, CDK2:ERH, CDK2:hsReq*-1 or CDK2:hsReq*-2 complexes. The protein components of the complexes have been implicated in cellular functions, including but not limited to: control of cell cycle progression, cellular differentiation and apoptosis, hyperproliferative disorders including tumorigenesis and tumor progression; degenerative disorders; regulation of transcription; control of intracellular signal transduction involving phosphorylation; intimal hyperplasia, re-stenosis, atherosclerosis, and neovascularization; pyrimidine metabolism, and various genetic disorders associated with impaired DNA repair.

Accordingly, the invention provides methods of screening CDK2:CDK2-IP complexes, particularly complexes of CDK2 with cyclin H, cyclin I, ERH, hsReq*-1 or hsReq*-2, and the hsReq*-1 and hsReq*-2 proteins, as well as derivatives and analogs of the CDK2:CDK2-IP complexes and hsReq*-1 and hsReq*-2 proteins for the ability to alter cell functions, particularly those cell functions in which CDK2 and/or a CDK2-IP has been implicated, such as but not limited to tumorigenesis and other hyperproliferative disorders, arthritis and neurodegeneration, atherosclerosis and other cardiovascular diseases, and various genetic disorders.

The present invention also relates to therapeutic and prophylactic as well as diagnostic, prognostic, and screening methods and compositions based upon CDK2:CDK2-IP complexes (and the nucleic acids encoding the individual proteins that participate in the complexes) as well as hsReq*-1 and hsReq*-2 proteins and nucleic acids. Therapeutic compounds of the invention include, but are not limited to, CDK2:CDK2-IP complexes and complexes where one or both members of the complex is a derivative or analog of CDK2 or a CDK2-IP; hsReq*-1 and hsReq*-2 proteins and derivatives, fragments and analogs thereof; antibodies to and nucleic acids encoding the foregoing; and antisense nucleic acids to the nucleotide sequences encoding the complex components and hsReq*-1 and hsReq*-2 antisense nucleic acids. Diagnostic, prognostic and screening kits are also provided.

Animal models and methods of screening for modulators (i.e. agonists, antagonists and inhibitors) of the activity of CDK2:CDK2-IP complexes and hsReq*-1 and hsReq*-2 proteins are also provided.

Methods of identifying molecules that inhibit, or alternatively, that increase formation of CDK2:CDK2-IP complexes are also provided.

4. BRIEF DESCRIPTION OF THE DRAWINGS

FIGS. 1A and 1B. The nucleotide sequence of CDK2 (GenBank Accession No. X61622 (SEQ ID NO:1) and deduced amino acid sequence (SEQ ID NO:2). The coding sequence in its entirety was used as bait in the assays described in Section 6, infra.

FIGS. 2A and 2B. The nucleotide sequence (SEQ ID NO:3) and amino acid sequence (SEQ ID NO:4) of cyclin H (GenBank Accession No. U11791). The arrows indicate the 5' start sites of identified prey sequences at bases 64, 76, 82, 94, 97, 100, 103, 163, 166, and 379 (amino acids 2, 6, 8, 12, 13, 14, 15, 35, 36, and 106).

FIGS. 3A and 3B. The nucleotide sequence (SEQ ID NO:5) and corresponding amino acid sequence (SEQ ID NO:6) of the cyclin I protein (GenBank Accession No. D50310). The prey sequence identified in the assay described in Section 6, infra, begins at base 46 (amino acid 16) and is indicated by arrow "A".

FIG. 4. The nucleotide acid sequence (SEQ ID NO:7) and amino acid sequence (SEQ ID NO:8) of EPRH (GenBank Accession No. D85758). The prey sequence identified in the assay described in Section 6, infra, begins at base 153 (amino acid 27) and is indicated by arrow "A".

FIGS. 5A and 5B. The nucleotide sequence of hsReq (GenBank Accession No. U94585; SEQ ID NO:9). The prey sequence identified in Section 6 infra and beginning at base 1789, is underlined. The second prey sequence identified in Section 6, infra and beginning at base 1819, is overlined. The initiation methionine codon ATG of hsReq is marked as "A", and the stop codon TGA for hsReq is marked as "C". A 5' splice site, with bases identical to the known consensus sequence for 5' splice sites is shown in bold, and the last base of the exon (exon 1) is marked by arrow "B". A 3' splice site, with bases identical to the known consensus sequence for 3' splice sites is shown in bold, and the first base of the exon (exon 2) is marked by arrow "E", and the stop codon TGA for hsReq*-1 is marked by "H". The branch point consensus sequence for this exon, with bases matching the consensus bases shown in bold, is marked as "D". An alternate 3' splice site is marked as "G", with the associated branch splice point marked as "F". The stop codon TGA in this exon for hsReq*-2, is indicated as "H". The AAUAAA transcriptional stop signal near the end of the sequence is marked as I.

FIGS. 6A, 6B and 6C. The hsReq*-1 nucleotide acid sequence (SEQ ID NO:10) and amino acid sequence (SEQ ID NO:11). The N-terminal amino acid residue of the amino acid sequence that differs from hsReq because of alternate splicing is marked by arrow "A". One prey sequence identified in the assay described in Section 6, infra, begins at base 1789 of the hsReq sequence (FIGS. 5A and 5B), and is indicated by arrow "B". The second prey sequence identified in the assay described in Section 6, infra, begins at base 1819 of the hsReq sequence (FIGS. 5A and 5B) and is indicated by arrow "C".

FIGS. 7A and 7B. The hsReq*-2 nucleotide sequence (SEQ ID NO:12) and amino acid sequence (SEQ ID NO:13). The amino acid sequence C-terminal to the amino acid marked by the arrow "A" deviates from the amino acid sequence of hsReq because of alternate splicing. One prey sequence identified in the assay described in Section 6, infra, begins at base 1789 of the hsReq sequence (FIGS. 5A and 5B), and is indicated by arrow "A". The second prey sequence identified in the assay described in Section 6, infra, begins at base 1819 of the hsReq sequence (FIGS. 5A and 5B), and is indicated by arrow "B".

FIG. 8. Schematic of the portions of CDK2, cyclin H, cyclin I, ERH, hsReq*-1 and hsReq*-2 that form a CDK2:CDK2-IP complex in the modified yeast two hybrid assay system. The amino acid sequences of CDK2, cyclin H, cyclin I, ERH, hsReq*-1 and hsReq*-2 proteins are depicted as bars, with the starting and ending amino acid numbers indicated above the bars (as depicted for each protein in FIGS. 1A–4 and 5A–7B (SEQ ID NOS: 2, 4, 6, 8, 11 and 13, respectively)). The portions of CDK2 used as bait, or the shortest sequences identified as interacting in the assay ("prey sequence") in the case of cyclin H, cyclin I, ERH, hsReq*-1 and hsReq*-2, are blackened and the first amino acid number of that prey sequence is indicated above each bar. In cases where more than one independent prey isolate was identified, i.e., for cyclin H, hsReq*-1, and hsReq*-2, the start sites for the longer prey sequences are indicated by bars, drawn to scale, that extend towards the amino terminus.

FIG. 9. Matrix of results of the modified yeast two hybrid system assays. The results of assays using the bait proteins B1 and CDK2 are indicated to the left of the rows, and the prey proteins cyclin H (Cyc. H), ERH, $p27^{kip}$, P1, $p21^{waf}$, and hsReq are indicated above the columns. A positive interaction for a bait and prey protein is indicated as "+" in the box forming the intersection between the particular bait and prey proteins; a lack of interaction is designated by an empty box. Boxes labeled A, B, C, D and E indicate the results of matings and growth of yeast expressing CDK2 and Cyclin H (Cyc. H), ERH, $p27^{kip}$, $p21^{waf}$, and hsReq, respectively. The box labeled F indicates the mating and growth of yeast expressing B1 and P1.

5. DETAILED DESCRIPTION OF THE INVENTION

The present invention is based upon the identification of proteins that interact with CDK2 (termed herein "CDK2-IPs") using an improved, modified form of the yeast two hybrid system. Cyclin H, cyclin I, ERH, and hsReq*-1 and hsReq*-2 (hsReq*-1 and hsReq*-2 are splice variants of hsReq as described in Section 5.2 infra) were found to form complexes under physiological conditions with CDK2 (the complexes of CDK2 with a CDK2-IP are indicated as "CDK2:CDK2-IP" complexes herein). These CDK2:CDK2-IP complexes are implicated in modulating the functional activities of CDK2 and the functional activities of its binding partners. Such functional activities include, but are not limited to, physiological processes including cell cycle control, transcriptional regulation, cellular apoptosis and differentiation, intracellular signal transduction by phosphorylation, pyrimidine metabolism and DNA repair, and pathological processes including but not restricted to hyperproliferative disorders including tumorigenesis and tumor progression, degenerative disorders including neurodegenerative disease, atherosclerosis and other vascular diseases, and various genetic disorders resulting from impaired DNA repair.

The present invention relates to methods of screening for proteins that interact with (e.g. bind to) CDK2. The invention further relates to CDK2 complexes, in particular CDK2 complexed with one of the following proteins: cyclin H, cyclin I, ERH, hsReq*-1 or hsReq*-2. The invention further relates to complexes of CDK2 or derivatives, analogs and fragments of CDK2 with cyclin H, cyclin I, ERH, hsReq*-1 or hsReq*-2 or derivatives, analogs and fragments thereof. In a preferred embodiment, such complexes bind an anti-CDK2:CDK2-IP complex antibody. In a specific embodiment, complexes of human CDK2 with human proteins are provided.

The invention also provides methods of producing and/or isolating CDK2:CDK2-IP complexes. In a specific embodiment, the invention provides methods of using recombinant DNA techniques to express both CDK2 and its binding partner (or fragments, derivatives or homologs of one or both members of the complex) either where both binding partners are under the control of one heterologous promoter (i.e. a promoter not naturally associated with the native gene encoding the particular complex component) or where each is under the control of a separate heterologous promoter.

In another aspect, the invention provides the nucleotide sequences of hsReq*-1 and hsReq*-2 and their encoded proteins. The present inventors identified portions of proteins that interact with CDK2 and that are encoded, in part, by nucleotide sequences present in the 3' untranslated region of the mRNA encoding hsReq. The present inventors also identified alternate splice sites in the hsReq gene (by methods described infra), and splicing at these sites could result in mRNAs containing the nucleotide sequences identified as encoding portions of proteins that interact with CDK2. These mRNAs encode the proteins hsReq*-1 and hsReq*-2. The nucleotide and amino acid sequences of hsRes*-1 and hsRes*-2 are depicted in FIG. 6 (SEQ ID NOS:10 and 11) and 7 (SEQ ID NOS:12 and 13), respectively.

The invention further relates to hsReq*-1 and hsReq*-2 proteins, derivatives, fragments and homologs thereof, as well as nucleic acids encoding the hsReq*-1 and hsReq*-2 proteins, derivatives, fragments and homologs. The invention provides hsReq*-1 and hsReq*-2 proteins and genes encoding these proteins of many different species, particularly vertebrates, and more particularly mammals. In a preferred embodiment, the hsReq*-1 and hsReq*-2 proteins and genes are of human origin. Production of the foregoing proteins and derivatives, e.g., by recombinant methods, is provided. In specific embodiments, the invention provides fragments of hsReq*-1 and hsReq*-2 that comprise all or a portion of an amino acid sequence not present in hsReq, i.e., the portion of hsReq*-1 and hsReq*-2 encoded by the alternately spliced sequence. These fragments comprise all or an at least 10, 20, 30 or 50 amino acid portion of amino acids 187 to 280 of the hsReq*-1 amino acid sequence as depicted in FIG. 6 (SEQ ID NO:11) and all or an at least 10, 20, 30 or 50 amino acid portion of amino acids 188 to 210 of the hsReq*-2 amino acid sequence as depicted in FIG. 7 (SEQ ID NO:13).

The invention further relates to hsReq*-1 and hsReq*-2 derivatives and analogs that are functionally active, i.e., capable of displaying one or more known functional activities associated with a full length (wild-type) hsReq*-1 and/or hsReq*-2. Such functional activities include, but are not limited to, ability to form a complex with CDK2, antigenicity [ability to bind (or compete with hsReq*-1 or hsReq*-2 for binding) to an anti-hsReq*-1 or anti-hsReq*-2 antibody, respectively], immunogenicity (ability to generate an antibody that binds to hsReq*-1 or hsReq*-2, respectively), etc. Derivatives comprising all or an at least 10, 20, 30 or 50 amino acid portion of amino acids 187 to 280 of the hsReq*-1 amino acid sequence as depicted in FIG. 6 (SEQ ID NO:11) and all or an at least 10, 20, 30 or 50 amino acid portion of amino acids 188 to 210 of the hsReq*-1 amino acid sequence as depicted in FIG. 7 (SEQ ID NO:13).

Methods of diagnosis, prognosis, and screening for diseases and disorders associated with aberrant levels of CDK2:CDK2-IP complexes or of hsReq*-1 or hsReq*-2 are provided. The invention also provides methods of treating or preventing diseases or disorders associated with aberrant levels of CDK2:CDK2-IP complexes or hsReq*-1 and/or hsReq*-2, or aberrant levels or activity of one or more of the components of a CDK2:CDK2-IP complex by administration of the CDK2:CDK2-IP complexes, hsReq*-1 or hsReq*-2 or modulators of CDK2:CDK2-IP complex formation or activity (e.g., antibodies that bind the CDK2:CDK2-IP complex, or non-complexed CDK2 or its binding partner or a fragment thereof—preferably the fragment containing the portion of CDK2 or the CDK2-IP that is directly involved in complex formation), mutants of CDK2 or the CDK2-IP that increase or decrease binding affinity, small molecule inhibitors/enhancers of complex formation, antibodies that either stabilize or neutralize the complex, etc.

Methods of assaying CDK2:CDK2-IP complexes, hsReq*-1 or hsReq*-2, for activity as therapeutics or diagnostics as well as methods of screening for CDK2:CDK2-IP complex, hsReq*-1 or hsReq*-2 modulators (i.e., inhibitors, agonists and antagonists) are also provided.

For clarity of disclosure, and not by way of limitation, the detailed description of the invention is divided into the subsections which follow.

5.1 CDK2:CDK2-IP Complexes and hsREQ*-1 and hsREQ-2 Proteins and Derivatives and Analogs The invention provides CDK2:CDK2-IP complexes, and, in particular aspects, complexes of CDK2 and cyclin H, CDK2 and cyclin I, CDK2 and ERH, CDK2 and hsReq*-1, and CDK2 and hsReq*-2. In a preferred embodiment, the CDK2:CDK2-IP complexes are complexes of human proteins. The invention also relates to complexes of derivatives (including fragments) and analogs of CDK2 with a CDK2-IP, complexes of CDK2 with derivatives (including fragments) and analogs of a CDK2-IP, and complexes of derivatives (including fragments) and analogs of CDK2 and a CDK2-IP (as used herein, fragment, derivative or analog of a CDK2:CDK2-IP complex includes complexes where one or both members of the complex are fragments, derivatives or analogs of the wild-type CDK2 or CDK2-IP protein). Preferably, the CDK2:CDK2-IP complexes in which one or both members of the complex are a fragment, derivative or analog of the wild type protein are functionally active CDK2:CDK2-IP complexes. In particular aspects, the native proteins, derivatives or analogs of CDK2 and/or the CDK2-IP are of animals, e.g. mouse, rat, pig, cow, dog, monkey, human, fly, frog, or of plants. "Functionally active CDK2:CDK2-IP complex" as used herein refers to that material displaying one or more known functional attributes of a complex of full length CDK2 with a full length CDK2-IP (e.g., cyclin H, cyclin I, ERH, hsReq*-1, or hsReq*-2) including but not exclusive to control of cell cycle progression, cellular differentiation and apoptosis, hyperproliferative disorders including tumorigenesis and tumor progression; degenerative disorders; regulation of transcription; control of intracellular signal transduction involving phosphorylation; intimal hyperplasia, re-stenosis, atherosclerosis, and neovascularization; pyrimidine metabolism, and various genetic disorders associated with impaired DNA repair.

Accordingly, the invention provides methods of screening CDK2:CDK2-IP complexes, particularly complexes of CDK2 with cyclin H, cyclin I, ERH, hsReq*-1 or hsReq*-2, and the hsReq*-1 and hsReq*-2 proteins, as well as derivatives and analogs of the CDK2:CDK2-IP complexes and hsReq*-1 and hsReq*-2 proteins for the ability to alter cell functions, particularly those cell functions in which CDK2 and/or a CDK2-IP has been implicated, such as but not limited to physiological processes including cell cycle control, transcriptional regulation, cellular apoptosis and differentiation, intracellular signal transduction by phosphorylation, pyrimidine metabolism and DNA repair, and pathological processes including but not limited to hyperproliferative disorders including tumorigenesis and tumor progression, degenerative disorders including neurodegenerative disease, atherosclerosis and associated vascular diseases, and various genetic disorders resulting from impaired DNA repair, as well as other activities, for example but not limited to, binding to an anti-CDK2:CDK2-IP complex antibody, etc. For example, such derivatives or analogs which have the desired immunogenicity or antigenicity can be used in immunoassays, for immunization, for inhibition of CDK2:CDK2-IP complex activity, etc. Derivatives or analogs that retain, or alternatively lack or inhibit, a property of interest (e.g., participation in a CDK2:CDK2-IP complex) can be used as inducers, or inhibitors, respectively, of such a property and its physiological correlates. A specific embodiment relates to a CDK2:CDK2-IP complex of a fragment of CDK2 and/or a fragment of CDK2-IP that can be bound by an anti-CDK2 and/or anti-CDK2-IP antibody or antibody specific for a CDK2:CDK2-IP complex when such a fragment is included within a CDK2:CDK2-IP complex.

Fragments and other derivatives or analogs of CDK2:CDK2-IP complexes can be tested for the desired activity by procedures known in the art, including but not limited to the assays described in Section 5.6.

In specific embodiments, the invention provides CDK2:CDK2-IP complexes comprising fragments of one or both members of the complex. In a preferred embodiment, these fragments consist of, but are not exclusive to, fragments of cyclin H, cyclin I, ERH, hsReq*-1, or hsReq*-2, identified as interacting with CDK2 in an improved yeast two hybrid assay (e.g., amino acids 2–323, 6–323, 8–323, 12–323, 13–323, 14–323, 15–323, 35–323, 36–323 and 106–323 of cyclin H as depicted in FIG. 2 (SEQ ID NO:4), amino acids 16–377 of cyclin I as depicted in FIG. 3 (SEQ ID NO:6), amino acids 27–104 of ERH as depicted in FIG. 4 (SEQ ID NO:8), amino acids 257–280 and 267–280 of hsReq*-1 as depicted in FIG. 6 (SEQ ID NO:11), and amino acids 188–210 and 197–200 of hsReq*-2 as depicted in FIG. 7 (SEQ ID NO:13)). Fragments, or proteins comprising fragments, lacking some or all of the foregoing regions of either member of the complex assay, are also provided. Nucleic acids encoding the foregoing are provided.

The invention further relates to hsReq*-1 and hsReq*-2 proteins as well as derivatives and homologs and paralogs of hsReq*-1 and hsReq*-2 proteins. In one embodiment human hsReq*-1 and hsReq*-2 genes and proteins are provided. In specific aspects, the native proteins, fragments, derivatives or analogs of hsReq*-1 or hsReq*-2 are of animals, e.g. mouse, rat, pig, cow, dog, monkey, human, fly, frog, or of plants. In other specific embodiments, the fragment, derivative or analog is functionally active, i.e., capable of exhibiting one or more functional activities associated with full-length, wild-type hsReq*-1 or hsReq*-2, e.g., ability to bind CDK2, immunogenicity or antigenicity.

The nucleotide sequences encoding, and the corresponding amino acid sequences of, human CDK2, cyclin H, cyclin I, and ERH are known (GenBank Accession No. X61622; GenBank Accession No. U11791; GenBank Accession No. D50310; and GenBank Accession No. D85785, respectively), and are provided in FIGS. 1–4, respectively (SEQ ID NOS:1, 3, 5, and 7, respectively). The nucleotide and amino acid sequences of hsReq*-1 and hsReq*-2 are provided in FIGS. 6 and 7, respectively (SEQ ID NOS:10–13, respectively) and are described in detail in Section 5.2 infra. Nucleic acids encoding CDK2, cyclin H, cyclin I, ERH, hsReq*-1 or hsReq*-2 can be obtained by any method known in the art, e.g., by PCR amplification using synthetic primers hybridizable to the 3' and 5' ends of the sequence and/or by cloning from a cDNA or genomic library using an oligonucleotide specific for the gene sequence (e.g., as described in Section 5.2, infra).

Homologs (e.g., nucleic acids encoding CDK2, cyclin H, cyclin I, and ERH of species other than human) or other related sequences (e.g., paralogs) can also be obtained by low, moderate or high stringency hybridization with all or a portion of the particular human sequence as a probe using methods well known in the art for nucleic acid hybridization and cloning (e.g., as described in Section 5.2, infra, for hsReq*-1 and hsReq*-2 sequences).

The CDK2, cyclin H, cyclin I, ERH, hsReq*-1 and hsReq*-2 proteins, either alone or in a complex, can be obtained by methods well known in the art for protein purification and recombinant protein expression. For recombinant expression of one or more of the proteins, the nucleic acid containing all or a portion of the nucleotide sequence encoding the protein can be inserted into an appropriate expression vector, i.e., a vector that contains the necessary elements for the transcription and translation of the inserted protein coding sequence. In a preferred embodiment, the regulatory elements (e.g., promoter) are heterologous (i.e., not the native gene promoter). The necessary transcriptional and translational signals can also be supplied by the native promoter for CDK2 or any CDK2-IP genes, and/or their flanking regions.

A variety of host-vector systems may be utilized to express the protein coding sequence. These include but are not limited to mammalian cell systems infected with virus (e.g. vaccinia virus, adenovirus, etc.); insect cell systems infected with virus (e.g. baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

In a preferred embodiment, the CDK2:CDK2-IP complexes are obtained by expressing the entire CDK2 coding sequence and a CDK2-IP coding sequence in the same cell, either under the control of the same promoter or two separate promoters. In yet another embodiment, a derivative, fragment or homolog of CDK2 and/or a derivative, fragment or homolog of a CDK2-IP are recombinantly expressed. Preferably the derivative, fragment or homolog of CDK2 and/or the CDK2-IP protein form a complex with a binding partner identified by a binding assay, such as the modified yeast two hybrid system described in Section 5.7.1 infra, more preferably form a complex that binds to an anti-CDK2:CDK2-IP complex antibody.

Any of the methods described in Section 5.2, infra, for the insertion of DNA fragments into a vector may be used to construct expression vectors containing a chimeric gene consisting of appropriate transcriptional/translational control signals and protein coding sequences. These methods may include in vitro recombinant DNA and synthetic techniques and in vivo recombinants (genetic recombination). Expression of nucleic acid sequences encoding CDK2 and a CDK2-IP (e.g., cyclin H, cyclin I, ERH, hsReq*-1, or hsReq*-2), or derivatives, fragments or homologs thereof, may be regulated by a second nucleic acid sequence so that the genes or fragments thereof are expressed in a host transformed with the recombinant DNA molecule(s). For example, expression of the proteins may be controlled by any promoter/enhancer known in the art. In a specific embodiment, the promoter is not native to the CDK2 or the CDK2-IP gene. Promoters which may be used include but are not limited to the SV40 early promoter (Bernoist and Chambon, 1981, Nature 290: 304–310), the promoter contained in the 3' long terminal repeat of Rous sarcoma virus (Yamamoto et al., 1980, Cell 22: 787–797), the herpes thymidine kinase promoter (Wagner et al., 1981, Proc. Natl. Acad. Sci. USA 78: 1441–1445), the regulatory sequences of the metallothionein gene (Brinster et al., 1982, Nature 296: 39–42); prokaryotic expression vectors such as the β-lactamase promoter (Villa-Kamaroff et al., 1978, Proc. Natl. Acad. Sci. USA 75: 3727–3731) or the tac promoter (DeBoer et al., 1983, Proc. Natl. Acad. Sci. USA 80: 21–25; see also "Useful Proteins from Recombinant Bacteria": in Scientific American 1980, 242:79–94); plant expression vectors comprising the nopaline synthetase promoter (Herrar-Estrella et al., 1984, Nature 303: 209–213) or the cauliflower mosaic virus 35S RNA promoter (Garder et al., 1981, Nucleic Acids Res. 9:2871), and the promoter of the photosynthetic enzyme ribulose bisphosphate carboxylase (Herrera-Estrella et al., 1984, Nature 310: 115–120); promoter elements from yeast and other fungi such as the Gal4 promoter, the alcohol dehydrogenase promoter, the phosphoglycerol kinase promoter, the alkaline phosphatase promoter, and the following animal transcriptional control regions that exhibit tissue specificity and have been utilized in transgenic animals: elastase I gene control region which is active in pancreatic acinar cells (Swift et al., 1984, Cell 38: 639–646; Ornitz et al., 1986, Cold Spring Harbor Symp. Quant. Biol. 50: 399–409; MacDonald 1987, Hepatology 7: 425–515); insulin gene control region which is active in pancreatic beta cells (Hanahan et al., 1985, Nature 315: 115–122), immunoglobulin gene control region which is active in lymphoid cells (Grosschedl et al., 1984, Cell 38: 647–658; Adams et al., 1985, Nature 318: 533–538; Alexander et al., 1987, Mol. Cell Biol. 7: 1436–1444), mouse mammary tumor virus control region which is active in testicular, breast, lymphoid and mast cells (Leder et al., 1986, Cell 45: 485–495), albumin gene control region which is active in liver (Pinckert et al., 1987, Genes and Devel. 1: 268–276), alpha-fetoprotein gene control region which is active in liver (Krumlauf et al., 1985, Mol. Cell. Biol. 5: 1639–1648; Hammer et al., 1987, Science 235: 53–58), alpha-1 antitrypsin gene control region which is active in liver (Kelsey et al., 1987, Genes and Devel. 1: 161–171), beta globin gene control region which is active in myeloid cells (Mogram et al., 1985, Nature 315: 338–340; Kollias et al., 1986, Cell 46: 89–94), myelin basic protein gene control region which is active in oligodendrocyte cells of the brain (Readhead et al., 1987, Cell 48: 703–712), myosin light chain-2 gene control region which is active in skeletal muscle (Sani 1985, Nature 314: 283–286), and gonadotrophic releasing hormone gene control region which is active in gonadotrophs of the hypothalamus (Mason et al., 1986, Science 234: 1372–1378).

In a specific embodiment, a vector is used that comprises a promoter operably linked to nucleic acid sequences encoding CDK2 and/or a CDK2-IP (e.g. cyclin H, cyclin I, ERH, hsReq*-1 or hsReq*-2), or a fragment, derivative or homolog, thereof, one or more origins of replication, and optionally, one or more selectable markers (e.g., an antibiotic resistance gene). In a preferred embodiment, a vector is used that comprises a promoter operably linked to nucleic acid sequences encoding both CDK2 and a CDK2-IP, one or more origins of replication, and optionally, one or more selectable markers.

In another specific embodiment, an expression vector containing the coding sequences, or portions thereof, of CDK2 and a CDK2-IP (e.g., cyclin H, cyclin I, ERH, hsReq*-1, or hsReq*-2), either together or separately, is made by subcloning the gene sequences into the EcoRI restriction site of each of the three pGEX vectors (glutathione S-transferase expression vectors; Smith and Johnson, 1988, Gene 7:31–40). This allows for the expression of products in the correct reading frame.

Expression vectors containing the sequences of interest can be identified by three general approaches: (a) nucleic acid hybridization, (b) presence or absence of "marker" gene function, and (c) expression of the inserted sequences. In the first approach, CDK2, cyclin H, cyclin I, ERH, hsReq*-1, or hsReq*-2, or other CDK2-IP sequences, can be detected by nucleic acid hybridization to probes comprising sequences homologous and complementary to the inserted sequences. In the second approach, the recombinant vector/host system can be identified and selected based upon the presence or absence of certain "marker" functions (e.g., binding to an anti-CDK2, anti-CDK2-IP, or anti-CDK2:CDK2-IP complex antibody, resistance to antibiotics, occlusion body formation in baculovirus, etc.) caused by insertion of the sequences of interest in the vector. For example, if CDK2 or a CDK2-IP gene, or portion thereof, is inserted within the marker gene sequence of the vector, recombinants containing the CDK2 or CDK2-IP fragment will be identified by the absence of the marker gene function. In the third approach, recombinant expression vectors can be identified by assaying for the CDK2, cyclin H, cyclin I, ERH, hsReq*-1, hsReq*-2, or other CDK2-IP product expressed by the recombinant vector. Such assays can be based, for example, on the physical or functional properties of the interacting species in in vitro assay systems, e.g., formation of a CDK2:CDK2-IP complex, immunoreactivity to antibodies specific for the protein, etc.

Once recombinant CDK2, cyclin H, cyclin I, ERH, hsReq*-1, hsReq*-2, or other CDK2-IP molecules are identified and the complexes or individual proteins isolated, several methods known in the art can be used to propagate them. Once a suitable host system and growth conditions have been established, recombinant expression vectors can be propagated and amplified in quantity. As previously described, the expression vectors or derivatives which can be used include, but are not limited to: human or animal viruses such as vaccinia virus or adenovirus; insect viruses such as baculovirus; yeast vectors; bacteriophage vectors such as lambda phage; and plasmid and cosmid vectors.

In addition, a host cell strain may be chosen that modulates the expression of the inserted sequences, or modifies or processes the expressed proteins in the specific fashion desired. Expression from certain promoters can be elevated in the presence of certain inducers; thus expression of the genetically-engineered CDK2 and/or CDK2-IP gene may be controlled. Furthermore, different host cells have characteristic and specific mechanisms for the translational and post-translational processing and modification (e.g. glycosylation, phosphorylation, etc.) of proteins. Appropriate cell lines or host systems can be chosen to ensure the desired modification and processing of the foreign protein is achieved. For example, expression in a bacterial system can be used to produce an unglycosylated core protein, while expression in mammalian cells ensures "native" glycosylation of a heterologous protein. Furthermore, different vector/host expression systems may effect processing reactions to different extents.

In other specific embodiments, the CDK2 and/or CDK2-IPs or fragments, homologs or derivatives thereof, may be expressed as fusion or chimeric protein products comprising the protein, fragment, homolog, or derivative joined via a peptide bond to a heterologous protein sequence of a different protein. Such chimeric products can be made by ligating the appropriate nucleic acid sequences encoding the desired amino acids to each other in the proper coding frame by methods known in the art, and expressing the chimeric products in a suitable host by methods commonly known in the art. Alternatively, such a chimeric product can be made by protein synthetic techniques, e.g., by use of a peptide synthesizer. Chimeric genes comprising portions of CDK2 and/or a CDK2-IP fused to any heterologous protein-encoding sequences may be constructed. A specific embodiment relates to a chimeric protein comprising a fragment of CDK2 and/or a CDK2-IP, or hsReq*-1, or hsReq*-2 of at least six amino acids.

In a specific embodiment, fusion proteins are provided that contain the domains of the CDK2 protein and a CDK2-IP that directly form CDK2:CDK2-IP complexes and, optionally, a heterofunctional reagent, such as a peptide linker, linking the two domains, where such a heterofunctional reagent, such as a reagent or linker promotes the interaction of the CDK2 and CDK2-IP binding domains. These fusion proteins may be particularly useful where the stability of the interaction is desirable (due to the formation of the complex as an intramolecular reaction), for example in production of antibodies specific to the CDK2:CDK2-IP complex.

In particular, CDK2 and/or CDK2-IP derivatives can be made by altering their sequences by substitutions, additions or deletions that provide for functionally equivalent molecules. Due to the degeneracy of nucleotide coding sequences, other DNA sequences that encode substantially the same amino acid sequence as a CDK2 or CDK2-IP gene can be used in the practice of the present invention. These include but are not limited to nucleotide sequences comprising all or portions of CDK2, cyclin H, cyclin I, ERH, hsReq*-1, or hsReq*-2, that are altered by the substitution of different codons that encode the same amino acid residue within the sequence, thus producing a silent change. Likewise, the CDK2 or CDK2-IP derivatives of the invention include, but are not limited to, those containing, as a primary amino acid sequence, all or part of the amino acid sequence of CDK2 or a CDK2-IP, including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, the nucleic acids encoding proteins and proteins consisting of or comprising a fragment of CDK2 or a CDK2-IP consisting of at least 6 (continuous) amino acids of CDK2 and/or a CDK2-IP are provided. In other embodiments, the fragment consists of at least 10, 20, 30, 40, or 50 amino acids of CDK2 or CDK2-IP. In specific embodiments, such fragments are not larger than 35, 100 or 200 amino acids. Derivatives or analogs of CDK2 and CDK2-IPs include but are not limited to molecules comprising regions that are substantially homologous to CDK2 or the CDK2-IPs in various embodiments, at least 30%, 40%, 50%, 60%, 70%, 80%, 90% or 95% identity over an amino acid sequence of identical size or when compared to an aligned sequence in which the alignment is done by a computer homology program known in the art or whose encoding nucleic acid is capable of hybridizing to a sequence encoding CDK2 or a CDK2-IP under stringent, moderately stringent, or nonstringent conditions (e.g., as described in Section 5.2 infra). In another specific embodiment, fragments and other derivatives and analogs of hsReq*-1 and hsReq*-2 are provided that comprise an at least 5, 10 or 25 amino acid portion of hsReq*-1 or hsReq*-2, respectively, which portion contains the amino acid sequence encoded by the splice junction. Nucleic acids are also provided that comprise, as well as nucleic acids (e.g., the inverse complement) that are hybridizable to or complementary to, an at least 5, 10 or 25 nucleotide portion of the nucleotide sequences encoding hsReq*-1 and hsReq*-2 that span the alternate splice junctions of the hsReq*-1 and hsReq*-2 coding sequence.

The CDK2 or CDK2-IP derivatives and analogs of the invention can be produced by various methods known in the art. The manipulations which result in their production can occur at the gene or protein level. For example, the cloned CDK2 and CDK2-IP gene sequence can be modified by any of numerous strategies known in the art (Sambrook et al., 1990, Molecular Cloning, A Laboratory Manual, 2d ed., Cold Spring Harbor Laboratory, Cold Spring Harbor, N.Y.). The sequences can be cleaved at appropriate sites with restriction endonuclease(s), followed by further enzymatic modification if desired, isolated, and ligated in vitro. In the production of the gene encoding a derivative or analog of CDK2 or a CDK2-IP, care should be taken to ensure that the modified gene retains the original translational reading frame, uninterrupted by translational stop signals, in the gene region where the desired activity is encoded.

Additionally, the CDK2- or CDK2-IP-encoding nucleic acid sequence or hsReq*-1 - or hsReq*-2-encoding nucleic acid sequence can be mutated in vitro or in vivo, e.g., to create variations in coding regions, to create and/or destroy translation, initiation, and/or termination sequences, and/or to form new restriction endonuclease sites or destroy pre-existing ones, to facilitate further in vitro modification. Any technique for mutagenesis known in the art can be used, including but not limited to, chemical mutagenesis and in vitro site-directed mutagenesis (Hutchinson et al., 1978, J. Biol. Chem 253:6551–6558), use of TAB™ linkers (Pharmacia), etc.

Once a recombinant cell expressing CDK2 and/or a CDK2-IP or hsReq*-1 or hsReq*-1 protein, or fragment or derivative thereof, is identified, the individual gene product or complex can be isolated and analyzed. This is achieved by assays based on the physical and/or functional properties of the protein or complex, including, but not limited to, radioactive labeling of the product followed by analysis by gel electrophoresis, immunoassay, cross-linking to marker-labeled product, etc.

The CDK2:CDK2-IP complexes, and hsReq*-1 and hsReq*-1 proteins may be isolated and purified by standard methods known in the art (either from natural sources or recombinant host cells expressing the complexes or proteins), including but not restricted to column chromatography (e.g., ion exchange, affinity, gel exclusion, reversed-phase high pressure, fast protein liquid, etc.), differential centrifugation, differential solubility, or by any other standard technique used for the purification of proteins. Functional properties may be evaluated using any suitable assay known in the art.

Alternatively, once CDK2 or CDK2-IP or its derivative is identified, the amino acid sequence of the protein can be deduced from the nucleic acid sequence of the chimeric gene from which it was encoded. As a result, the protein or its derivative can be synthesized by standard chemical methods known in the art (see, e.g., Hunkapiller et al., 1984, Nature 310: 105–111).

In a specific embodiment of the present invention, such CDK2:CDK2-IP complexes, and hsReq*-1 and hsReq*-2 proteins, whether produced by recombinant DNA techniques, chemical synthesis methods, or by purification from native sources, include but are not limited to those containing, as a primary amino acid sequence, all or part of the amino acid sequences substantially as depicted in FIGS. 1–4, 6 and 7 (SEQ ID NOS:2, 4, 6, 8, 11 and 13), as well as fragments and other analogs and derivatives thereof, including proteins homologous thereto.

Manipulations of CDK2 and/or CDK2-IP sequences, or hsReq*-1 or hsReq*-2 sequences may be made at the protein level. Included within the scope of the invention are complexes of CDK2 or CDK2-IP fragments, derivatives or analogs and hsReq*-1 and hsReq*-2 fragments, derivatives and analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, NaBH4, acetylation, formylation, oxidation, reduction, metabolic synthesis in the presence of tunicamycin, etc.

In specific embodiments, the CDK2 and/or CDK2-IP sequences are modified to include a fluorescent label. In another specific embodiment, the CDK2 and/or the CDK2-IP are modified to have a heterofunctional reagent, such heterofunctional reagents can be used to crosslink the members of the complex.

In addition, complexes of analogs and derivatives of CDK2 and/or a CDK2-IP, or analogs and derivatives of hsReq*-1 or hsReq*-2 can be chemically synthesized. For example, a peptide corresponding to a portion of CDK2 and/or a CDK2-IP, or hsReq*-1 or hsReq*-2, which comprises the desired domain or which mediates the desired activity in vitro (e.g., CDK2:CDK2-IP complex formation), can be synthesized by use of a peptide synthesizer. Furthermore, if desired, nonclassical amino acids or chemical amino acid analogs can be introduced as a substitution or addition into the CDK2 and/or CDK2-IP, or hsReq*-1 or hsReq*-2 sequence. Non-classical amino acids include but are not limited to the D-isomers of the common amino acids, α-amino isobutyric acid, 4-aminobutyric acid, Abu, 2-aminobutyric acid, Abu, Ahx, 6-amino hexanoic acid, Aib, 2-amino isobutyric acid, 3-amino propionoic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In cases where natural products are suspected of being mutant or are isolated from new species, the amino acid sequence of CDK2, a CDK2-IP, hsReq*-1, or hsReq*-2 isolated from the natural source, as well as those expressed in vitro, or from synthesized expression vectors in vivo or in vitro, can be determined from analysis of the DNA sequence, or alternatively, by direct sequencing of the isolated protein. Such analysis may be performed by manual sequencing or through use of an automated amino acid sequenator.

The CDK2:CDK2-IP complexes, and hsReq*-1 or hsReq*-2 proteins may also be analyzed by hydrophilicity analysis (Hopp and Woods, 1981, Proc. Natl. Acad. Sci. USA 78: 3824–3828). A hydrophilicity profile can be used to identify the hydrophobic and hydrophilic regions of the proteins, and help predict their orientation in designing substrates for experimental manipulation, such as in binding experiments, antibody synthesis, etc. Secondary structural analysis can also be done to identify regions of the CDK2 and/or a CDK2-IP, or hsReq*-1 or hsReq*-2 that assume specific structures (Chou and Fasman, 1974, Biochemistry 13: 222–23). Manipulation, translation, secondary structure prediction, hydrophilicity and hydrophobicity profiles, open reading frame prediction and plotting, and determination of sequence homologies, can be accomplished using computer software programs available in the art.

Other methods of structural analysis including but not limited to X-ray crystallography (Engstrom, 1974, Biochem. Exp. Biol. 11:7–13), mass spectroscopy and gas chromatography (Methods in Protein Science, J. Wiley and Sons, New York, 1997), and computer modeling (Fletterick and Zoller, eds., 1986, Computer Graphics and Molecular Modeling, In: Current Communications in Molecular Biology, Cold Spring Harbor Laboratory, Cold Spring Harbor Laboratory Press, New York) can also be employed.

5.2 hsREQ*-1 and hsREQ*-2 Genes and Other Nucleic Acids

The invention relates to the nucleotide sequences of nucleic acids encoding hsReq*-1 and hsReq*-2. In specific embodiments, the hsReq*-1 and hsReq*-2 nucleic acids comprise the sequences of SEQ ID NO:10 and SEQ ID NO:12, respectively, or portions thereof, or proteins comprising the amino acid sequences of SEQ ID NO:11 or SEQ ID NO:13, respectively, or portions thereof. The invention provides purified nucleic acids consisting of at least 8 nucleotides (i.e., a hybridizable portion) of an hsReq*-1 or hsReq*-2 sequence, which portion spans the splice junction (i.e., containing at least one residue on either side of the splice junction) specific to hsReq*-1 or hsReq*-2 (i.e., the portion of the hsReq*-1 or hsReq*-2 nucleotide sequence containing the sequence at which the 5' and 3' splice sites utilized in processing hsReq*-1 and hsReq*-2 mRNAs and not the hsReq mRNA were joined) for example, but are not limited to, a nucleic acid consisting of nucleotides both 5' and 3' of nucleotide number 559 of the hsReq*-1 nucleotide sequence as depicted in FIG. 6 (SEQ ID NO:10) or nucleotide number 559 of the hsReq*-2 nucleotide sequence as depicted in FIG. 7 (SEQ ID NO:12); in other embodiments, the nucleic acids consist of at least 10 (continuous) nucleotides, 25 nucleotides, 50 nucleotides, 100 nucleotides, 150 nucleotides, or 200 nucleotides of the hsReq*-1 or hsReq*-2 sequence that includes an at least 5, 10 or 25 nucleotide portion of the hsReq*-1 or hsReq*-2 nucleotide sequence both 3' and 5' to the splice junction sequences, or a full-length hsReq*-1 or hsReq*-2 coding sequence. In another embodiment, the nucleic acids are smaller than 35, 200 or 500 nucleotides in length. Nucleic acids can be single or double stranded. The invention also relates to nucleic acids hybridizable to or complementary to the foregoing sequences, which nucleic acids contain an at least 5, 10 or 25 nucleotide sequence spanning the alternate splice junction of hsReq*-1 or hsReq*-2 or an at least 5, 10 or 25 nucleotide sequence absolutely complementary to the sequence spanning the alternate splice junction of hsReq*-1 or hsReq*-2. In particular, the invention provides the inverse complement to nucleic acids hybridizable to the foregoing sequences (i.e., the inverse complement of a nucleic acid strand has the complementary sequence running in reverse orientation to the strand so that the inverse complement would hybridize without mismatches to the nucleic acid strand; thus, for example, where the coding strand is hybridizable to a nucleic acid with no mismatches between the coding strand and the hybridizable strand, then the inverse complementary of the hybridizable strand is identical to the coding strand). In specific aspects, nucleic acids are provided which comprise a sequence complementary to (specifically, are the inverse complement of) at least 10, 25, 50, 100, or 200 nucleotides, or the entire coding region, of an hsReq*-1 or hsReq*-2 gene, that includes the portion of the hsReq*-1 or hsReq*-2 nucleotide sequence that spans the alternate splice junction (i.e., not the splice junction formed in hsReq mRNA processing) of hsReq*-1 or hsReq*-2.

In a specific embodiment, a nucleic acid which is hybridizable to an hsReq*-1 or hsReq*-2 nucleic acid (e.g., having sequence antisense to SEQ ID NO:10 or 12, respectively), which nucleic acid contains an at least 5, 10 or 25 nucleotide sequence spanning the alternate splice junction of hsReq*-1 or hsReq*-2, or an at least 5, 10 or 25 nucleotide sequence absolutely complementary to the sequence spanning the alternate splice junction of hsReq*-1 or hsReq*-2, or to a nucleic acid encoding an hsReq*-1 or hsReq*-2 derivative, under conditions of low stringency is provided. By way of example and not limitation, procedures using such conditions of low stringency are as follows (see also Shilo and Weinberg, 1981, Proc. Natl. Acad. Sci. USA 78:6789–6792): Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 hours at 40° C., and then washed for 1.5 hours at 55° C. in a solution containing 2×SSC, 25 mM Tris-Cl (pH 7.4), 5 mM EDTA, and 0.1% SDS. The wash solution is replaced with fresh solution and incubated an additional 1.5 hours at 60° C. Filters are blotted dry and exposed for autoradiography. If necessary, filters are washed for a third time at 65–68° C. and reexposed to film. Other conditions of low stringency which may be used are well known in the art (e.g., as employed for cross-species hybridizations).

In another specific embodiment, a nucleic acid which is hybridizable to an hsReq*-1 or hsReq*-2 nucleic acid, which nucleic acid contains an at least 5, 10 or 25 nucleotide sequence spanning the alternate splice junction of hsReq*-1 or hsReq*-2, or an at least 5, 10 or 25 nucleotide sequence absolutely complementary to the sequence spanning the alternate splice junction of hsReq*-1 or hsReq*-2, under conditions of high stringency is provided. By way of example and not limitation, procedures using such conditions of high stringency are as follows: Pre-hybridization of filters containing DNA is carried out for 8 hours to overnight at 65° C. in buffer composed of 6×SSC, 50 mM Tris-Cl (pH 7.5), 1 mM EDTA, 0.02% PVP, 0.02% Ficoll, 0.02% BSA, and 500 µg/ml denatured salmon sperm DNA. Filters are hybridized for 48 hours at 65° C. in pre-hybridization mixture containing 100 µg/ml denatured salmon sperm DNA and 5–20×10$^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 minutes before autoradiography. Other conditions of high stringency which may be used are well known in the art.

In another specific embodiment, a nucleic acid, which is hybridizable to an hsReq*-1 or hsReq*-2 nucleic acid, which nucleic acid contains an at least 5, 10 or 25 nucleotide sequence spanning the alternate splice junction of hsReq*-1 or hsReq-2, or an at least 5, 10 or 25 nucleotide sequence absolutely complementary to the sequence spanning the alternate splice junction of hsReq*-1 or hsReq*-2, under conditions of moderate stringency is provided. For example, but not limited to, procedures using such conditions of moderate stringency are as follows: Filters containing DNA are pretreated for 6 hours at 55° C. in a solution containing 6×SSC, 5×Denhart's solution, 0.5% SDS and 100 µg/ml denatured salmon sperm DNA. Hybridizations are carried out in the same solution and 5–20×10$^6$ cpm $^{32}$P-labeled probe is used. Filters are incubated in hybridization mixture for 18–20 hours at 55° C., and then washed twice for 30 minutes at 60° C. in a solution containing 1×SSC and 0.1% SDS. Filters are blotted dry and exposed for autoradiography. Other conditions of moderate stringency which may be used are well-known in the art. Washing of filters is done at 37° C. for 1 hour in a solution containing 2×SSC, 0.1% SDS.

Nucleic acids encoding derivatives (including fragments) and analogs of hsReq*-1 or hsReq*-2 proteins (see Section 5.1), and hsReq*-1 or hsReq*-2 antisense nucleic acids (see Section 5.5.7) are additionally provided. As is readily apparent, as used herein, a "nucleic acid encoding a fragment or portion of an hsReq*-1 or hsReq*-2" shall be construed as referring to a nucleic acid encoding only the recited fragment or portion of hsReq*-1 or hsReq*-2 protein and not the other contiguous portions of hsReq*-1 or hsReq*-2 as a continuous sequence.

Fragments of hsReq*-1 or hsReq*-2 nucleic acids comprising regions conserved between (with homology to) other hsReq*-1 or hsReq*-2 nucleic acids, of the same or different species, are also provided. Specifically, the invention relates to fragments of hsReq*-1 and hsReq*-2 nucleic acids comprising a portion of the hsReq*-1 or hsReq*-2 nucleotide sequence that spans the alternate splice junction of hsReq*-1 or hsReq*-2.

Regions within the 3' untranslated regions of the known protein cDNAs for hsReq were identified as encoding a protein or proteins that interact with CDK2 using the improved version of the yeast two hybrid system (e.g., as described in in Section 6.1 infra). The present inventors determined that the nucleotide sequences encoding the interacting proteins are identical to an untranslated portion of the hsReq nucleotide sequence from nucleotides 1789 to 2400 and from nucleotides 1819 to 2400 (as depicted in FIG. 7 (SEQ ID NO:9)).

That the nucleotide sequence encoding the portions of the hsReq*-1 and hsReq*-2 identified as interacting with CDK2 are in the 3' untranslated region of hsReq indicates that hsReq*-1 and hsReq*-2 are encoded by mRNAs resulting from splicing of the unprocessed hsReq gene mRNA at splice sites other than the splice sites used in processing hsReq mRNA. These hsReq*-1 and hsReq*-2 sequences were determined by identifying alternate 5' and 3' splice sites in the hsReq sequence.

Determination of 5' and 3' splice points for protein splice variants can be performed by any method known in the art. For example, but not by way of limitation, the 5' and 3' splice points can be determined as follows:

First, potential 5' splice sites can be identified in the coding sequence of the known protein, i.e., hsReq. The sequence of 5' splice sites has an invariant GT sequence at the start of the intron, and the remaining bases are not invariant, but the preferred consensus sequence is AG:GTAAGT, with the colon indicating the splice point (Padgett et al., 1984, Ann. Rev. Biochem. 55:1119–1150). Potential splice sites can be identified in order of the number of residues matching this consensus sequence, requiring at a minimum, the invariant GT and 4/6 matches in the other consensus bases.

Next, potential 3' intron:exon splice sites can also be identified based on the consensus analysis described by Padgett et al. (1984, Ann. Rev. Biochem. 55:1119–1150). The 3' intron:exon splice site must have an AG sequence just 5' to the splice site (denoted as "AG:") and the base just 5' to (preceding) the AG: sequence must be a C or a T. Then, the nucleotides which are 5 to 14 nucleotides 5' of the last G nucleotide of the intron can contain at most two non-T, non-C bases (Padgett et al., 1984, Ann. Rev. Biochem. 55:1119–1150). To identify such a potential 3' intron-:exon splice site, the sequence between a potential 5' splice site and the start of the nucleotide sequence encoding the detected interacting protein or protein fragment is scanned for the invariant AG: sequence, where the base preceding the invariant region must be a C or T.

Next, based on the known translational frame of the mature protein and each predicted 5' splice site, compatible translational frames for successful splicing are defined for potential 3' splice sites. Nucleotide sequences can be analyzed by a number of nucleotide sequence analysis programs available in the art to define possible protein translation products. Translation in the three forward translation frames defines possible open reading frames (contiguous spans of codons for amino acids without the presence of a stop codon). Only those 3' sites that match the necessary translational frame of a 5' prime splice junction are retained. Unmatched 5' or 3' splice sites are eliminated. In cases where no ideal 3' splice site match is found, sites containing three non-C, non-T bases upstream of the splice site are then examined.

Finally, for each possible 5':3' splice site pair, a search for a mammalian branch point consensus sequence is performed (Reed and Maniatis, 1988, Genes Dev. 2:1268–1276). The branch point is identified by the consensus sequence T/CNCTGAC to which 5 of the 6 defined bases must match and the consensus sequence must be 20–60 nucleotides 5' of the 3' splice site. Though not absolutely required for pre mRNA splicing, the presence of the consensus sequence increases splicing efficiency. Thus, 5':3' splice site pairs with a branch point consensus sequence are retained over splice site pairs that do not have a branch point consensus sequence.

Finally, new splice variant proteins must encode at least 60 amino acid residues to constitute a viable in vivo product. Further, the 3' end of slice variants must, by definition, extend into the identified interacting sequence. The amino acid and nucleotide sequences for two splice variants of hsReq, named hsReq*-1 and hsReq*-2 and depicted in FIGS. 6 and 7, respectively, were determined in silico as described above and as exemplified in Section 6.3 infra. For hsReq*-1, a 5' splice site was identified at nucleotides 563–570 of the hsReq nucleotide sequence (indicated by "B" on the hsReq nucleotide sequence in FIG. 5), with the last base of the first exon being nucleotide number 564, as indicated by an arrow in FIG. 5, and a 3' splice site was identified at nucleotides 1566 to 1580 of the hsReq nucleotide sequence (indicated by "E" on the hsReq nucleotide sequence in FIG. 5), with the first base of the second exon being nucleotide number 1580, as indicated by an arrow in FIG. 5. The translation stop codon of hsReq*-1 was identified as nucleotides 1861 to 1863 of the hsReq nucleotide sequence (indicated as "H" in FIG. 5 (SEQ ID NO:9)). The branch point consensus region for hsReq*-1 splicing was identified at nucleotides 1538 to 1544 of the hsReq nucleotide sequence as depicted in FIG. 5 (SEQ ID NO: 9) (indicated by a "D" in FIG. 5).

For hsReq*-2, a 5' splice site was identified at nucleotides 563–570 of the hsReq sequence, as depicted in FIG. 5 (SEQ ID NO: 9) and as indicated by "B", with the last base of the first exon being nucleotide number 564, as indicated by an arrow in FIG. 5, and a 3' splice site was identified at nucleotides 1776–1790 of the hsReq nucleotide sequence, as depicted in FIG. 5 (SEQ ID NO:9) and indicated as "G" in FIG. 5, with the last base of the second exon being nucleotide number 1790, as indicated by an arrow in FIG. 5. The branch point site associated with this 3' splice site is at nucleotides 1759 to 1765 of the hsReq sequence in FIG. 5 (SEQ ID NO:9) and is indicated as "F" in FIG. 5, and the translation stop codon for hsReq*-2 is nucleotides 1861 to 1863 of the hsReq nucleotide sequence (indicated as "H" in FIG. 5).

Any method available in the art can be used to obtain a full length (i.e., encompassing the entire coding region) cDNA clone encoding hsReq*-1 and hsReq*-2. In particular, the polymerase chain reaction (PCR) can be used to amplify the splice variant sequence in a cDNA library. Oligonucleotide primers that hybridize to sequences at the 3' and 5' termini of splice variants can be used as primers to amplify by PCR sequences from a nucleic acid sample (RNA or DNA), preferably a cDNA library, from an appropriate source (e.g. the sample from which the initial cDNA library for the modified yeast two hybrid assay fusion population was derived).

PCR can be carried out, e.g., by use of a Perkin-Elmer Cetus thermal cycler and Taq polymerase (Gene Amp™).

The DNA being amplified is preferably cDNA from any eukaryotic species. One can choose to synthesize several different degenerate primers, for use in the PCR reactions. It is also possible to vary the stringency of hybridization conditions used in priming the PCR reactions, to amplify nucleic acid homologs (e.g., to obtain hsReq*-1 or hsReq*-2 sequences from species other than humans or to obtain human sequences with homology to hsReq*-1 or hsReq*-2) by allowing for greater or lesser degrees of nucleotide sequence similarity between the known nucleotide sequence and the nucleic acid homolog being isolated. For cross species hybridization, low stringency conditions are preferred. For same species hybridization, moderately stringent conditions are preferred.

After successful amplification of the nucleic acid containing all or a portion of a nucleic acid encoding all or a portion of an hsReq*-1 or hsReq*-2 homolog, that segment may be molecularly cloned and sequenced, and utilized as a probe to isolate a complete cDNA. This, in turn, will permit the determination of the gene's complete nucleotide sequence, the analysis of its expression, and the production of its protein product for functional analysis, as described infra. In this fashion, the nucleotide sequences of the entire hsReq*-1 or hsReq*-2 mRNA, as well as additional genes encoding hsReq*-1 or hsReq*-2 proteins and analogs may be identified.

Any eukaryotic cell potentially can serve as the nucleic acid source for the molecular cloning of the hsReq*-1 or hsReq*-2 sequences. The nucleic acids can be isolated from vertebrate, mammalian, human, porcine, bovine, feline, avian, equine, canine, as well as additional primate sources, insects, plants, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell (see, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

Preferably, hsReq*-1 and hsReq*-2 nucleic acids are isolated from a cDNA source. Identification of the specific cDNA containing the desired sequence may be accomplished in a number of ways. For example, a portion of the hsReq*-1 or hsReq*-2 (of any species) sequence (e.g., a PCR amplification product obtained as described above), or an oligonucleotide having a sequence of a portion of the known nucleotide sequence, or its specific RNA, or a fragment thereof, may be purified, amplified, and labeled, and the generated nucleic acid fragments may be screened by nucleic acid hybridization to the labeled probe (Benton, W. and Davis, R., 1977, Science 196:180; Grunstein, M. And Hogness, D., 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available or by DNA sequence analysis and comparison to the known nucleotide sequence of hsReq*-1 or hsReq*-2. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isolectric focusing behavior, proteolytic digestion maps, or antigenic properties or ability to bind CDK2, as known for hsReq*-1 or hsReq*-2. If an anti-hsReq*-1 or anti-hsReq*-2 antibody is available, the protein may be identified by binding of labeled antibody to the clone putatively synthesizing hsReq*-1, or hsReq*-2, in an ELISA (enzyme-linked immunosorbent assay)-type procedure.

Alternatives to isolating hsReq*-1 or hsReq*-2 DNA include, but are not limited to, chemically synthesizing the gene sequence itself from a known sequence. Other methods are possible and within the scope of the invention.

The identified and isolated nucleic acids can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid derivatives or the Bluescript vector (Stratagene). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and hsReq*-1 or hsReq*-2 gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionation, can be done before insertion into the cloning vector.

In specific embodiments, transformation of host cells with recombinant DNA molecules that incorporate the isolated hsReq*-1 or hsReq*-2 gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The hsReq*-1 or hsReq*-2 sequences provided by the instant invention include those nucleotide sequences encoding substantially the same amino acid sequences as found in native hsReq*-1 or hsReq*-2 proteins, and those encoded amino acid sequences with functionally equivalent amino acids, as well as those encoding other hsReq*-1 or hsReq*-2 derivatives or analogs, as described in Section 5.1 supra for CDK2 and CDK2-IP derivatives and analogs.

5.3 Antibodies to CDK2:CDK2-IP Complexes, hsReq*-1 and hsReq-2 Proteins

According to the invention, the CDK2:CDK2-IP complexes (e.g. CDK2-IP complexed with cyclin H, cyclin I, ERH, hsReq*-1 or hsReq*-2), or fragments, derivatives or homologs thereof, or hsReq*-1 or hsReq*-2 protein and fragments, homologs and derivatives thereof may be used as immunogens to generate antibodies which immunospecifically bind such immunogens. Such antibodies include but are not limited to polyclonal, monoclonal, chimeric, single chain, Fab fragments, and an Fab expression library. In a specific embodiment, antibodies to complexes of human CDK2 and human CDK2-IP are produced. In another embodiment, complexes formed from fragments of CDK2 and a CDK2-IP, which fragments contain the protein domain that interacts with the other member of the complex, are used as immunogens for antibody production. In another specific embodiment, hsReq*-1 and hsReq*-2, or fragments, derivatives, or homologs thereof are used as immunogens.

Various procedures known in the art may be used for the production of polyclonal antibodies to a CDK2:CDK2-IP complex, derivative or analog, or hsReq*-1 and hsReq*-2 proteins, derivatives, fragments or analogs.

For production of the antibody, various host animals can be immunized by injection with the native CDK2:CDK2-IP complex, hsReq*-1 or hsReq*-2 protein or a synthetic version, or a derivative of the foregoing, such as a cross-linked CDK2:CDK2-IP, such host animals include but are not limited to rabbits, mice, rats, etc. Various adjuvants can be used to increase the immunological response, depending on the host species, and include but are not limited to Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacille Calmette-Guerin (BCG) and corynebacterium parvum.

For preparation of monoclonal antibodies directed towards a CDK2:CDK2-IP complex, or hsReq*-1 or hsReq*-2, or derivatives, fragments or analogs thereof, any technique that provides for the production of antibody molecules by continuous cell lines in culture may be used. Such techniques include but are not restricted to the hybridoma technique originally developed by Kohler and Milstein (1975, Nature 256: 495–497), the trioma technique, the human B-cell hybridoma technique (Kozbor et al., 1983, Immunology Today 4: 72), and the EBV hybridoma technique to produce human monoclonal antibodies (Cole et al., 1985, In: Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. USA 80: 2026–2030), or by transforming human B cells with EBV virus in vitro (Cole et al., 1985, In: Monoclonal Antibodies and Cancer Therapy, Alan R. Liss, Inc., pp. 77–96). In fact, according to the invention, techniques developed for the production of "chimeric antibodies" (Morrison et al., 1984, Proc. Natl. Acad. Sci. USA 81: 6851–6855; Neuberger et al., 1984, Nature 312:604–608; Takeda et al., 1985, Nature 314: 452–454) by splicing the genes from a mouse antibody molecule specific for the CDK2:CDK2 complex or hsReq*-1 or hsReq*-2 protein together with genes from a human antibody molecule of appropriate biological activity can be used; such antibodies are within the scope of this invention.

According to the invention, techniques described for the production of single chain antibodies (e.g., as described in U.S. Pat. No. 4,946,778) can be adapted to produce CDK2:CDK2-IP complex-specific and hsReq*-1- and hsReq*-2-specific single chain antibodies. An additional embodiment of the invention utilizes the techniques described for the construction of Fab expression libraries (Huse et al., 1989, Science 246: 1275–1281) to allow rapid and easy identification of monoclonal Fab fragments with the desired specificity for CDK2:cyclin H, CDK2:cyclin I, CDK2:ERH, CDK2:hsReq*-1 or CDK2:hsReq*-2 complexes, hsReq*-1 or hsReq*-2 proteins or derivatives, or analogs thereof. Non-human antibodies can be "humanized" by known methods (see, e.g., U.S. Pat. No. 5,225,539).

Antibody fragments that contain the idiotypes of CDK2:CDK2-IP complexes or of hsReq*-1 and hsReq*-2 proteins, can be generated by techniques known in the art. For example, such fragments include but are not limited to: the F(ab')2 fragment that can be produced by pepsin digestion of the antibody molecule; the Fab' fragments that can be generated by reducing the disulfide bridges of the F(ab')2 fragment, the Fab fragments that can be generated by treating the antibody molecular with papain and a reducing agent, and Fv fragments.

In the production of antibodies, screening for the desired antibody can be accomplished by techniques known in the art, e.g., ELISA (enzyme-linked immunosorbent assay). To select antibodies specific to a particular domain of the CDK2:CDK2 complex, or hsReq*-1 or hsReq*-2, one may assay generated hybridomas for a product that binds to the fragment of the CDK2:CDK2-IP complex, or hsReq*-1 or hsReq*-2 that contains such a domain. For selection of an antibody that specifically binds a CDK2:CDK2-IP complex but that does not specifically bind to the individual proteins of the CDK2:CDK2-IP complex, one can select on the basis of positive binding to the CDK2:CDK2-IP complex and a lack of binding to the individual CDK2 and CDK2-IP proteins. Additionally, in specific embodiments, antibodies are generated that immunospecifically recognize the portion of the hsReq*-1 or hsReq*-2 having an amino acid sequence that differs from the hsReq amino acid sequence and that do not immunospecifically recognize hsReq.

Antibodies specific to a domain of the CDK2:CDK2-IP complex are also provided, as are antibodies to specific domains of hsReq*-1 and hsReq*-2.

The foregoing antibodies can be used in methods known in the art relating to the localization and/or quantitation of CDK2:CDK2-IP complexes and hsReq*-1 and hsReq*-2 proteins of the invention, e.g., for imaging these proteins, measuring levels thereof in appropriate physiological samples, in diagnostic methods, etc.

In another embodiment of the invention (see infra), anti-CDK2:CDK2-IP complex antibodies and fragments thereof, or anti-hsReq*-1 or anti-hsReq*-2 antibodies, or fragments thereof, containing the binding domain, are Therapeutics.

5.4 Diagnostic, Prognostic, and Screening Uses of CDK2:CDK2-IP Complexed and hsReq*-1 and hsReq*-2 Proteins CDK2:CDK2-IP complexes (particularly CDK2 complexed with cyclin H, cyclin I, ERH, hsReq*-1 or hsReq*-2), or hsReq*-1 or hsReq*-2 proteins, may be markers of specific disease states involving disruption of physiological processes including but not limited to cell cycle progression, cellular apoptosis and/or differentiation, intracellular signal transduction, transcriptional regulation, DNA repair, and pyrimidine metabolism and pathological processes including but not limited to hyperproliferative disorders, including tumorigenesis and tumor progression, degenerative disorders including neurodegeneration, vascular disorders, including atherosclerosis, and various genetic disorders resulting from aberrant DNA repair, and thus have diagnostic utility. Further, definition of particular groups of patients with elevations or deficiencies of a CDK2:CDK2-IP complex, or a hsReq*-1 or hsReq*-2 protein can lead to new nosological classifications of diseases, furthering diagnostic ability. Detecting levels of CDK2:CDK2-IP complexes, or individual proteins that have been shown to form complexes with CDK2, or the hsReq*-1 or hsReq*-2 proteins, or detecting levels of the mRNA encoding the components of the CDK2:CDK2-IP complexes, or the hsReq*-1 or hsReq*-2 proteins, may be used in diagnosis, prognosis, to follow the course of disease states, to follow therapeutic response, etc.

CDK2:CDK2-IP complexes and the individual components of the CDK2:CDK2-IP complexes (e.g., CDK2, cyclin H, cyclin I, ERH, hsReq*-1 and hsReq*-2), and derivatives, analogs and subsequences thereof, CDK2 and/or CDK2-IP, hsReq*-1 and hsReq*-2 nucleic acids (and sequences complementary thereto), and anti-CDK2:CDK2-IP complex antibodies and antibodies directed against the individual components that can form CDK2:CDK2-IP complexes and anti-hsReq*-1 and anti-hsReq*-2 antibodies, have uses in diagnostics. Such molecules can be used in assays, such as immunoassays, to detect, prognose, diagnose, or monitor various conditions, diseases, and disorders characterized by aberrant levels of CDK2:CDK2-IP complexes, or hsReq*-1 or hsReq*-2 proteins, or monitor the treatment thereof.

In particular, such an immunoassay is carried out by a method comprising contacting a sample derived from a patient with an anti-CDK2:CDK2-IP complex antibody or anti-hsReq*-1 or anti-hsReq*-2 antibody under conditions such that immunospecific binding can occur, and detecting or measuring the amount of any immunospecific binding by the antibody. In a specific aspect, such binding of antibody, in tissue sections, can be used to detect aberrant CDK2:CDK2-IP complex, or hsReq*-1 or hsReq*-2 protein localization or aberrant (e.g., high, low or absent) levels of CDK2:CDK2-IP complex or complexes or hsReq*-1 or hsReq*-2 proteins. In a specific embodiment, antibody to CDK2:CDK2-IP complex can be used to assay in a patient tissue or serum sample for the presence of CDK2:CDK2-IP complex where an aberrant level of CDK2:CDK2-IP complex is an indication of a diseased condition. In another embodiment, antibody to hsReq*-1 or hsReq*-2 can be used to assay in a patient tissue or serum sample for the presence of hsReq*-1 or hsReq*-2 where an aberrant level of hsReq*-1 or hsReq*-2 is an indication of a diseased condition. By "aberrant levels" is meant an increased or decreased level relative to that present, or a standard level representing that present, in an analogous sample from a portion of the body or from a subject not having the disorder.

The immunoassays which can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

Nucleic acids encoding the components of the CDK2:CDK2-IP complexes (e.g., CDK2, cyclin H, cyclin I, ERH, hsReq*-1 and hsReq*-2) and the hsReq*-1 and hsReq*-2 proteins and related nucleotide sequences and subsequences, including complementary sequences, can also be used in hybridization assays. The CDK2, CDK2-IP, hsReq*-1 and hsReq*-2 nucleotide sequences (specifically portions of the hsReq*-1 and hsReq*-2 nucleotide sequences that span the alternate splice junctions of hsReq*-1 and hsReq*-2 mRNAs), or subsequences thereof comprising about at least 8 nucleotides, can be used as hybridization probes. Hybridization assays can be used to detect, prognose, diagnose, or monitor conditions, disorders, or disease states associated with aberrant levels of the mRNAs encoding the components of a CDK2:CDK2-IP complex or hsReq*-1 or hsReq*-2 protein as described supra. In particular, such a hybridization assay is carried out by a method comprising contacting a sample containing nucleic acid with a nucleic acid probe capable of hybridizing to CDK2, a CDK2-IP, or hsReq*-1 or hsReq*-2 DNA or RNA, under conditions such that hybridization can occur, and detecting or measuring any resulting hybridization. In a preferred aspect, the hybridization assay is carried out using nucleic acid probes capable of hybridizing to CDK2 and to a binding partner of CDK2 (e.g. cyclin H, cyclin I, ERH, hsReq*-1 or hsReq*-2) to measure concurrently the expression of both members of a CDK2:CDK2-IP complex. In other specific embodiments, the hybridization assay is carried out using nucleic acid probes capable of hybridizing to hsReq*-1 or hsReq*-2 but not hsReq, e.g., a probe specific for the splice junction of the 5' and 3' splice sites used to process the mRNA encoding hsReq*-1 and hsReq*-2.

In specific embodiments, diseases and disorders involving or characterized by aberrant levels of CDK2:CDK2-IP complexes (e.g., complexes of CDK2 with cyclin H, cyclin I, ERH, hsReq*-1 or hsReq*-2) can be diagnosed, or their suspected presence can be screened for, or a predisposition to develop such disorders can be detected, by detecting aberrant levels of CDK2:CDK2-IP complexes, or un-complexed CDK2 and/or CDK2-IP (e.g. cyclin H, cyclin I, ERH, hsReq*-1 or hsReq*-2) proteins or nucleic acids or functional activity, including but not restricted to, binding to an interacting partner (e.g. CDK2, cyclin H, cyclin I, ERH, hsReq*-1 or hsReq*-2), or by detecting mutations in CDK2 and/or a CDK2-IP RNA, DNA or protein (e.g., translocations, truncations, changes in nucleotide or amino acid sequence relative to wild-type CDK2 and/or the CDK2-IP) that cause increased or decreased expression or activity of a CDK2:CDK2-IP complex and/or CDK2 and/or a protein that binds to CDK2. Such diseases and disorders include but are not limited to those described in Section 5.5 and its subsections.

By way of example, levels of CDK2:CDK2-IP complexes and the individual components of CDK2:CDK2-IP complexes can be detected by immunoassay, levels of CDK2 and/or CDK2-IP mRNA can be detected by hybridization assays (e.g., Northern blots, dot blots), binding of CDK2 to a CDK2-IP can be done by binding assays commonly known in the art, translocations and point mutations in CDK2 and/or in genes encoding CDK2-IPs can be detected by Southern blotting, RFLP analysis, PCR using primers that preferably generate a fragment spanning at least most of the CDK2 and/or CDK2-IP gene, sequencing of the CDK2 and/or CDK2-IP genomic DNA or cDNA obtained from the patient, etc.

Assays well known in the art (e.g. assays described above such as immunoassays, nucleic acid hybridization assays, activity assays, etc.) can be used to determine whether one or more particular CDK2:CDK2-IP complexes are present at either increased or decreased levels or are absent in samples from patients suffering from a particular disease or disorder or having a predisposition to develop such a disease or disorder as compared to the levels in samples from subjects not having such a disease or disorder. Additionally, these assays can be used to determine whether the ratio of the CDK2:CDK2-IP complex to the un-complexed components of the CDK2:CDK2-IP complex, i.e. CDK2 and/or the specific CDK2-IP in the complex of interest (e.g., cyclin H, cyclin I, ERH, hsReq*-1 or hsReq*-2) is increased or decreased in samples from patients suffering from a particular disease or disorder or having a predisposition to develop such a disease or disorder as compared to the ratio in samples from subjects not having such a disease or disorder. In the event that levels of one or more particular CDK2:CDK2-IP complexes are determined to be increased in patients suffering from a particular disease or disorder or having a predisposition to develop such a disease or disorder, then the particular disease or disorder or predisposition for a disease or disorder can be diagnosed, have prognosis defined for, be screened for, or be monitored by detecting increased levels of the one or more CDK2:CDK2-IP complexes, the mRNA that encodes the members of the one or more particular CDK2:CDK2-IP complexes, or CDK2:CDK2-IP complex functional activity.

Accordingly, in a specific embodiment of the invention, diseases and disorders involving increased levels of one or more CDK2:CDK2-IP complexes can be diagnosed, or their suspected presence can be screened for, or a predisposition to develop such diseases and disorders can be detected, by detecting increased levels of the one or more CDK2:CDK2-IP complexes, the mRNA encoding both members of the complex, or complex functional activity, or by detecting mutations in CDK2 or the CDK2-IP (e.g., translocations in nucleic acids, truncations in the gene or protein, changes in nucleotide or amino acid sequence relative to wild-type CDK2 or the CDK2-IP) that enhance or stabilize CDK2:CDK2-IP complex formation.

In the event that levels of one or more particular CDK2:CDK2-IP complexes are determined to be decreased in patients suffering from a particular disease or disorder or having a predisposition to develop such a disease or disorder, then the particular disease or disorder or predisposition for a disease or disorder can be diagnosed, have its prognosis determined, be screened for, or be monitored by detecting decreased levels of the one or more CDK2:CDK2-IP complexes, the mRNA that encodes the members of the particular one or more CDK2:CDK2-IP complexes, or CDK2:CDK2-IP complex functional activity.

Accordingly, in a specific embodiment of the invention, diseases and disorders involving decreased levels of one or more CDK2:CDK2-IP complexes can be diagnosed, or their suspected presence can be screened for, or a predisposition to develop such disorders can be detected, by detecting decreased levels of the one or more CDK2:CDK2-IP complexes, the mRNA encoding the members of the one or more complexes, or complex functional activity, or by detecting mutations in CDK2 or the CDK2-IP (e.g., translocations in nucleic acids, truncations in the gene or protein, changes in nucleotide or amino acid sequence relative to wild-type CDK2 or the CDK2-IP) that inhibit or destabilize CDK2:CDK2-IP complex formation.

In another specific embodiment, diseases and disorders involving aberrant expression of hsReq*-1 and hsReq*-2 are diagnosed, or their suspected presence can be screened for, or a predisposition to develop such disorders can be detected, by detecting aberrant levels of hsReq*-1 or hsReq*-2 protein, RNA, or functional activity, or by detecting mutations in hsReq*-1 or hsReq*-2 RNA, DNA or protein (e.g., translocations in nucleic acids, truncations in the gene or protein, changes in nucleotide or amino acid sequence relative to wild-type hsReq*-1 or hsReq*-2) that cause aberrant expression (including aberrant splicing) or activity of hsReq*-1 or hsReq*-2. Such diseases and disorders include but are not limited to those described infra Section 5.5. By way of example, levels of hsReq*-1 or hsReq*-2 RNA and protein, CDK2 binding activity, and the presence of translocations or point mutations, can be determined as described above.

Assays well known in the art (e.g. assays described above such as immunoassays, nucleic acid hybridization assays, activity assays, etc.) can be used to determine whether hsReq*-1 or hsReq*-2 are present at either increased or decreased levels or are absent in samples from patients suffering from a particular disease or disorder or having a predisposition to develop such a disease or disorder as compared to the levels in samples from subjects not having such a disease or disorder. In the event that levels of hsReq*-1 or hsReq*-2 are determined to be increased in patients suffering from a particular disease or disorder or having a predisposition to develop such a disease or disorder, then the particular disease or disorder or predisposition for a disease or disorder can be diagnosed, have its prognosis determined, be screened for, or be monitored by detecting increased levels of hsReq*-1 or hsReq*-2 protein or mRNA, or hsReq*-1 or hsReq*-2 functional activity (e.g. binding to CDK2).

Accordingly, in a specific embodiment of the invention, diseases and disorders involving increased levels of hsReq*-1 or hsReq*-2 can be diagnosed, or their suspected presence can be screened for, or a predisposition to develop such disorders can be detected, by detecting increased levels of hsReq*-1 or hsReq*-2 proteins or nucleic acids, increased hsReq*-1 or hsReq*-2 functional activity, or by detecting mutations in hsReq*-1 or hsReq*-2 (e.g., translocations in nucleic acids, truncations in the gene or protein, changes in nucleotide or amino acid sequence relative to wild-type hsReq*-1 or hsReq*-2) that increase or stabilize hsReq*-1 or hsReq*-2 functional activity.

In the event that levels of hsReq*-1 or hsReq*-2 are determined to be decreased in patients suffering from a particular disease or disorder or having a predisposition to develop such a disease or disorder, then the particular disease or disorder or predisposition for a disease or disorder can be diagnosed, or prognosis determined, be screened for, or be monitored by detecting decreased levels of the hsReq*-1 or hsReq*-2 proteins or nucleic acids, or hsReq*-1 or hsReq*-2 functional activity.

Accordingly, in a specific embodiment of the invention, diseases and disorders involving decreased levels of hsReq*-1 or hsReq*-2 can be diagnosed, or their suspected presence can be screened for, or a predisposition to develop such disorders can be detected, by detecting decreased levels of hsReq*-1 or hsReq*-2 proteins or nucleic acids, decreased hsReq*-1 or hsReq*-2 functional activity or by detecting mutations in hsReq*-1 or hsReq*-2 (e.g., translocations in nucleic acids, truncations in the gene or protein, changes in nucleotide or amino acid sequence relative to wild-type hsReq*-1 or hsReq*-2) that destabilize or reduce hsReq*-1 or hsReq*-2 activity.

The use of detection techniques, especially those involving antibodies against the CDK2:CDK2-IP complexes or hsReq*-1 or hsReq*-2, provides methods of detecting specific cells that express the complex or protein. Using such assays, specific cell types can be defined in which one or more particular CDK2:CDK2-IP complex, or hsReq*-1 or hsReq*-2 protein are expressed, and the presence of the complex or protein can be correlated with cell viability by cell sorting techniques well known in the art.

Also embodied are methods to detect a CDK2:CDK2-IP complex, or hsReq*-1 or hsReq*-2 protein, in cell culture models that express particular CDK2:CDK2-IP complexes or hsReq*-1 or hsReq*-2, or derivatives thereof, for the purpose of characterizing or preparing CDK2:CDK2-IP complexes, or hsReq*-1 or hsReq*-2 for harvest. This embodiment includes cell sorting of prokaryotes such as but not restricted to, bacteria (Davey and Kell, 1996, Microbiol. Rev. 60: 641–696), primary cultures and tissue specimens from eukaryotes, including mammalian species such as human (Steele et al., 1996, Clin. Obstet. Gynecol 39: 801–813), and continuous cell cultures (Orfao and Ruiz-Arguelles, 1996, Clin. Biochem. 29: 5–9). Such isolations can be used as methods of diagnosis, described supra.

Kits for diagnostic use are also provided, that comprise in one or more containers an anti-CDK2:CDK2-IP complex antibody or an anti-hsReq*-1 or anti-hsReq*-2 antibody, and, optionally, a labeled binding partner to the antibody. Alternatively, the anti-CDK2:CDK2-IP complex antibody, or anti-hsReq*-1 or anti-hsReq*-2 antibody can be labeled (with a detectable marker, e.g., a chemiluminescent, enzymatic, fluorescent, or radioactive moiety). A kit is also provided that comprises in one or more containers a nucleic acid probe or probes capable of hybridizing to CDK2 and/or a CDK2-IP (e.g., cyclin H, cyclin I, ERH, hsReq*-1 or hsReq*-2) mRNA. In a specific embodiment, a kit can comprise in one or more containers a pair of primers (e.g., each in the size range of 6–30 nucleotides) that are capable of priming amplification [e.g., by polymerase chain reaction (see e.g., Innis et al., 1990, PCR Protocols, Academic Press, Inc., San Diego, Calif.), ligase chain reaction (see EP 320,308) use of β-replicase, cyclic probe reaction, or other methods known in the art], under appropriate reaction conditions of at least a portion of a CDK2 and/or a CDK2-IP, or hsReq*-1 or hsReq*-2 nucleic acid. A kit can optionally further comprise in a container a predetermined amount of a purified CDK2:CDK2-IP complex, CDK2 and/or a CDK2-IP, or hsReq*-1 or hsReq*-2 or nucleic acids thereof, e.g., for use as a standard or control.

5.5 Therapeutic Uses of CDK2:CDK2-IP Complexes and hsReq*-1 and hsReq*-2

The invention provides for treatment or prevention of various diseases and disorders by administration of a therapeutic compound (termed herein "Therapeutic"). Such "Therapeutics" include but are not limited to: CDK2:CDK2-IP complexes (e.g. CDK2 complexed with cyclin H, cyclin I, ERH, hsReq*-1 or hsReq*-2), CDK2 and the individual CDK2-IPs (e.g., cyclin H, cyclin I, ERH, hsReq*-1 and hsReq*-2) proteins and analogs and derivatives (including fragments) of the foregoing (e.g., as described hereinabove); antibodies thereto (as described hereinabove); nucleic acids encoding the CDK2 and the CDK2-IP and hsReq*-1 and hsReq*-2, and analogs or derivatives, thereof (e.g., as described hereinabove); CDK2, CDK2-IP, hsreq*-1 and hsReq*-2 antisense nucleic acids, and CDK2:CDK2-IP complex and hsReq*-1 or hsReq*-2 modulators (i.e., inhibitors, agonists and antagonists).

CDK2 and several of its binding partners, as identified herein (e.g., cyclin H, cyclin I, ERH, hsReq*-1 and hsReq*-2), are implicated significantly in disorders of cell cycle progression, cell differentiation, and transcriptional control, including cancer and tumorigenesis and tumor progression. Disorders of neurodegeneration resulting from altered cellular apoptosis, differentiation, and DNA repair can likewise involve these same proteins. Aberrant DNA repair and transcriptional control also results in various genetic disorders, including xeroderma pigmentosum, Cockayne's syndrome and trichothiodystrophy (Seroz et al., 1995, Curr. Opin. Genet. Dev. 5: 217–222). A wide range of cell diseases affected by intracellular signal transduction, are treated or prevented by administration of a Therapeutic that modulates (i.e. inhibits, antagonizes or promotes) CDK2:CDK2-IP complex activity, or hsReq*-1 and hsReq*-2 activity. ERH is specifically implicated in disorders of pyrimidine metabolism.

Diseases and disorders associated with aberrant levels of CDK2:CDK2-IP complex levels or activity or aberrant levels of CDK2 and/or a CDK2-IP, hsReq*-1 or hsReq*-2 may be treated or prevented by administration of a Therapeutic that modulates CDK2:CDK2-IP complex formation or activity, or hsReq*-1 and hsReq*-2 levels or activity. In a specific embodiment, the activity or level of CDK2 is modulated by administration of a CDK2-IP. In another specific embodiment, the activity or level of a CDK2-IP is modulated by administration of CDK2.

Diseases and disorders characterized by increased (relative to a subject not suffering from the disease or disorder) CDK2:CDK2-IP levels or activity, or increased hsReq*-1 or hsReq*-2 levels or activity can be treated with Therapeutics that antagonize (i.e., reduce or inhibit) CDK2:CDK2-IP complex formation or activity, or hsReq*-1 or hsReq*-2 levels or activity. Therapeutics that can be used include but are not limited to CDK2 or a CDK2-IP or analogs, derivatives or fragments thereof, anti-CDK2:CDK2-IP complex antibodies (e.g. antibodies specific for CDK2:cyclin H, CDK2:cyclin I, CDK2:ERH, CDK2:hsReq*-1 or CDK2hsReq*-2 complexes) and anti-hsReq*-1 and anti-hsReq*-2 antibodies (fragments and derivatives thereof containing the binding region thereof), nucleic acids encoding CDK2 or a CDK2-IP, concurrent administration of CDK2 and a CDK2-IP antisense nucleic acid, or an hsreq*-1 or an hsReq*-2 anti-sense nucleic acid, and CDK2 and/or CDK2-IP, or hsreq*-l or hsReq*-2 nucleic acids that are dysfunctional (e.g., due to a heterologous (non-CDK2 and/or non-CDK2-IP, or non-hsReq*-1 or non-hsReq*-2) insertion within the coding sequences of the CDK2, CDK2-IP, hsReq*-1 or hsReq*-2 coding sequences) that are used to "knockout" endogenous CDK2 and/or CDK2-IP, or individual hsReq*-1 or hsReq*-2 function by homologous recombination (see, e.g., Capecchi, 1989, Science 244: 1288–1292). In a specific embodiment of the invention, a nucleic acid containing a portion of a CDK2 and/or a CDK2-IP, or hsReq*-1 or hsReq*-2 gene in which the CDK2, CDK2-IP, or individual hsReq*-1 or hsReq*-2 sequences flank (are both 5' and 3' to) a different gene sequence, is used, as a CDK2 and/or CDK2-IP or individual hsReq*-1 and hsReq*-2 antagonist, to promote CDK2 and/or CDK2-IP, or individual hsReq*-1 or hsReq*-2 inactivation by homologous recombination (see also Koller and Smithies, 1989, Proc. Natl. Acad. Sci. USA 86: 8932–8935; Zijlstra et al., 1989, Nature 342: 435–438). Additionally, mutants or derivatives of a first CDK2-IP protein that have greater affinity for CDK2 than the wild type first CDK2-IP may be administered with a second CDK2-IP protein for CDK2 binding, thereby reducing the levels of CDK2 complexes with the second CDK2-IP. Other Therapeutics that inhibit CDK2:CDK2-IP complex, hsReq*-1 or hsReq*-2 function can be identified by use of known convenient in vitro assays, e.g., based on their ability to inhibit CDK2:CDK2-IP binding or as described in Section 5.6 infra .

In specific embodiments, Therapeutics that antagonize CDK2:CDK2-IP complex formation or activity or hsReq*-1 or hsReq*-2 activity are administered therapeutically (including prophylactically): (1) in diseases or disorders involving an increased (relative to normal or desired) level of CDK2:CDK2-IP complex, or hsReq*-1 or hsReq*-2 proteins, for example, in patients where CDK2:CDK2-IP complexes or hsReq*-1 or hsReq*-2 are overactive or overexpressed; or (2) in diseases or disorders wherein in vitro (or in vivo) assays (see infra) indicate the utility of CDK2:CDK2-IP complex or hsReq*-1 or hsReq*-2 antagonist administration. Increased levels of CDK2:CDK2-IP complexes or hsReq*-1 or hsReq*-2 protein can be readily detected, e.g., by quantifying protein and/or RNA, by obtaining a patient tissue sample (e.g., from biopsy tissue) and assaying it in vitro for RNA or protein levels, structure and/or activity of the expressed CDK2:CDK2-IP complex (or the CDK2 and CDK2-IP mRNA), or hsReq*-1 or hsReq*-2 protein or mRNA. Many methods standard in the art can be thus employed, including but not limited to, immunoassays to detect CDK2:CDK2-IP complexes or hsReq*-1 or hsReq*-2 and/or visualize CDK2:CDK2-IP complexes or hsReq*-1 or hsReq*-2 protein (e.g., Western blot, immunoprecipitation followed by sodium dodecyl sulfate polyacrylamide gel electrophoresis, immunocytochemistry, etc.) and/or hybridization assays to detect concurrent expression of CDK2 and a CDK2-IP, or hsReq*-1 or hsReq*-2 mRNA (e.g., Northern assays, dot blots, in situ hybridization, etc.).

A more specific embodiment includes methods of reducing CDK2:CDK2-IP complex expression (i.e., the expression of the two components of the CDK2:CDK2-IP complex and/or formation of the complex), or hsReq*-1 or hsReq*-2 expression, by targeting mRNAs that express the protein moieties. RNA therapeutics currently fall within three classes, antisense species, ribozymes, or RNA aptamers (Good et al., 1997, Gene Therapy 4: 45–54).

Antisense oligonucleotides have been the most widely used. By way of example, but not for limitation, antisense oligonucleotide methodology to reduce CDK2 complex formation is presented below in subsection 5.5.7 infra. Ribozyme therapy involves the administration, induced expression, etc., of small RNA molecules with enzymatic ability to cleave, bind, or otherwise inactivate specific RNAs to reduce or eliminate expression of particular proteins (Grassi and Marini, 1996, Annals of Medicine 28: 499–510; Gibson, 1996, Cancer and Metastasis Reviews 15: 287–299). At present, the design of "hairpin" and "hammerhead" RNA ribozymes is necessary to specifically target a particular mRNA such as that for CDK2. RNA aptamers are specific RNA ligands for proteins, such as for Tat and Rev RNA (Good et al., 1997, Gene Therapy 4: 45–54) that can specifically inhibit their translation. Aptamers specific for CDK2 or a CDK2-IP can be identified by many methods well known in the art, for example but not limited to the protein-protein interaction assay described in Section 5.7.1 infra.

In another embodiment, the activity or level of CDK2 is reduced by administration of a CDK2-IP, or a nucleic acid that encodes the CDK2-IP, or antibody that immunospecifically binds to the CDK2-IP, or a fragment or a derivative of the antibody containing the binding domain thereof. Additionally, the levels or activity of a CDK2-IP may be reduced by administration of CDK2 or a nucleic acid encoding CDK2, or an antibody that immunospecifically binds CDK2, or a fragment or derivative of the antibody containing the binding domain thereof.

In another aspect of the invention, diseases or disorders associated with increased levels of CDK2 or a particular CDK2-IP (e.g. cyclin H, cyclin I, ERH, hsReq*-1 or hsReq*-2) may be treated or prevented by administration of a Therapeutic that increases CDK2:CDK2-IP complex formation if the complex formation acts to reduce or inactivate CDK2 or the particular CDK2-IP through the CDK2:CDK2-IP complex formation. Such diseases or disorders can be treated or prevented by administration of one member of the CDK2:CDK2-IP complex, including mutants of a member of the CDK2:CDK2-IP that have increased affinity for the other member of the CDK2:CDK2-IP complex (to cause increased complex formation), administration of antibodies or other molecules that stabilize the CDK2:CDK2-IP complex, etc.

Diseases and disorders associated with underexpression of a CDK2:CDK2-IP, or CDK2, or a particular CDK2-IP, are treated or prevented by administration of a Therapeutic that promotes (i.e., increases or supplies) CDK2:CDK2-IP complex or CDK2 or the CDK2-IP function. Examples of such a Therapeutic include but are not limited to CDK2:CDK2-IP complexes and hsReq*-1 and hsReq*-2 proteins and derivatives, analogs and fragments thereof that are functionally active (e.g., active to form CDK2:CDK2-IP complexes), uncomplexed CDK2 and CDK2-IP proteins and derivatives, analogs, and fragments thereof, and nucleic acids encoding the members of a CDK2:CDK2-IP complex, or encoding hsReq*-1 or hsReq*-2 or functionally active derivatives or fragments thereof (e.g., for use in gene therapy). In a specific embodiment, derivatives, homologs or fragments of CDK2 and/or a CDK2-IP that increase and/or stabilize CDK2:CDK2-IP complex formation are used as therapeutics. Examples of other agonists can be identified using in vitro assays or animal models, examples of which are described in Section 5.6 infra.

In specific embodiments, Therapeutics that promote CDK2:CDK2-IP complex function, or hsReq*-1 or hsReq*-2 function, are administered therapeutically (including prophylactically): (1) in diseases or disorders involving an absence or decreased (relative to normal or desired) level of CDK2:CDK2-IP complex, or hsReq*-1 or hsReq*-2 proteins, for example, in patients where CDK2:CDK2-IP complexes (or the individual components necessary to form the complexes) or hsReq*-1 or hsReq*-2 is lacking, genetically defective, biologically inactive or underactive, or under-expressed; or (2) in diseases or disorders wherein in vitro (or in vivo) assays (see infra) indicate the utility of CDK2:CDK2-IP complex or hsReq*-1 or hsReq*-2 agonist administration. The absence or decreased level of CDK2:CDK2-IP complex or hsReq*-1 or hsReq*-2 protein or function can be readily detected, e.g., by obtaining a patient tissue sample (e.g., from biopsy tissue) and assaying it in vitro for RNA or protein levels, structure and/or activity of the expressed CDK2:CDK2-IP complex (or for the concurrent expression of mRNA encoding the two components of the CDK2:CDK2-IP complex) or hsReq*-1 or hsReq*-2 RNA or protein. Many methods standard in the art can be thus employed, including but not limited to immunoassays to detect and/or visualize CDK2:CDK2-IP complexes (or the individual components of CDK2:CDK2-IP complexes), or hsReq*-1 or hsReq*-2 (e.g., Western blot, immunoprecipitation followed by sodium dodecyl sulfate polyacrylamide gel electrophoresis, immunocytochemistry, etc.) and/or hybridization assays to detect expression of the mRNA encoding the individual protein components of the CDK2:CDK2-IP complexes by detecting and/or visualizing CDK2 and a CDK2-IP mRNA concurrently or separately using, e.g., Northern assays, dot blots, in situ hybridization, etc.

In specific embodiments, the activity of levels of CDK2 are increased by administration of a CDK2-IP, or derivative or analog thereof, a nucleic acid encoding a CDK2-IP, or an antibody that immunospecifically binds a CDK2-IP, or a fragment or derivative of the antibody containing the binding domain thereof. In another specific embodiment, the activity or levels of a CDK2-IP are increased by administration of CDK2, or derivative or analog thereof, a nucleic acid encoding CDK2, or an antibody that immunospecifically binds CDK2, or a fragment or derivative of the antibody containing the binding domain thereof.

Generally, administration of products of a species origin or species reactivity (in the case of antibodies) that is the same species as that of the patient is preferred. Thus, in a preferred embodiment, a human CDK2:CDK2-IP complex, or hsReq*-1 or hsReq*-2 protein, or derivative or analog thereof, nucleic acids encoding the members of the human CDK2:CDK2-IP complex or human hsReq*-1 or human hsReq*-2 or derivative or analog thereof, an antibody to a human CDK2:CDK2-IP complex or hsReq*-1 or hsReq*-2 or derivative thereof, is therapeutically or prophylactically administered to a human patient.

Preferably, suitable in vitro or in vivo assays are utilized to determine the effect of a specific Therapeutic and whether its administration is indicated for treatment of the affected tissue.

In various specific embodiments, in vitro assays can be carried out with representative cells of cell types involved in a patient's disorder, to determine if a Therapeutic has a desired effect upon such cell types.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used. Additional descriptions and sources of Therapeutics that can be used according to the invention are found in Sections 5.1–5.3 and 5.8 herein.

5.5.1 Malignancies

Components of the CDK2:CDK2-IP complexes (i.e., CDK2, cyclin H, cyclin I, ERH, hsReq*-1 and hsReq*-2) have been implicated in regulation of cell proliferation. Accordingly, Therapeutics of the invention may be useful in treating or preventing diseases or disorders associated with cell hyperproliferation or loss of control of cell proliferation, particularly cancers, malignancies and tumors. Therapeutics of the invention can be assayed by any method known in the art for efficacy in treating or preventing malignancies and related disorders. Such assays include in vitro assays using transformed cells or cells derived from the tumor of a patient or in vivo assays using animal models of cancer or malignancies, or any of the assays described in Sections 5.6 infra. Potentially effective Therapeutics, for example but not by way of limitation, inhibit proliferation of tumor or transformed cells in culture or cause regression of tumors in animal models in comparison to controls.

Accordingly, once a malignancy or cancer has been shown to be amenable to treatment by modulating (i.e., inhibiting, antagonizing or agonizing) CDK2:CDK2-IP complex activity or hsReq*-1 or hsReq*-2 activity, that cancer or malignancy can be treated or prevented by administration of a Therapeutic that modulates CDK2:CDK2-IP complex formation and function, including supplying CDK2:CDK2-IP complexes and the individual binding partners of a CDK2:CDK2-IP complex, e.g., CDK2, cyclin H, cyclin I, ERH, hsReq*-1 or hsReq*-2. Such cancers and malignancies include but are not limited to those listed in Table 1 (for a review of such disorders, see Fishman et al., 1985, Medicine, 2d Ed., J.B. Lippincott Co., Philadelphia).

TABLE 1

MALIGNANCIES AND RELATED DISORDERS

Leukemia
acute leukemia acute lymphocytic leukemia
acute myelocytic leukemia
myeloblastic
promyelocytic
myelomonocytic
monocytic
erythroleukemia
chronic leukemia
chronic myelocytic (granulocytic) leukemia
chronic lymphocytic leukemia
Polycythemia vera
Lymphoma Hodgkin's disease
non-Hodgkin's disease
Multiple myeloma
Waldenström's macroglobulinemia
Heavy chain disease
Solid tumors
sarcomas and carcinomas fibrosarcoma
myxosarcoma
liposarcoma
chondrosarcoma
osteogenic sarcoma
chordoma
angiosarcoma
endotheliosarcoma
lymphangioendotheliosarcoma
synovioma
mesothelioma
Ewing's tumor
leiomyosarcoma
rhabdomyosarcoma
colon carcinoma
pancreatic cancer
breast cancer
ovarian cancer
prostate cancer
squamous cell carcinoma
basal cell carcinoma
adenocarcinoma
sweat gland carcinoma
sebaceous gland carcinoma
papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
uterine cancer
testicular tumor
lung carcinoma
small cell lung carcinoma
bladder carcinoma
epithelial carcinoma
glioma
astrocytoma
medul loblastoma
craniopharyngioma
ependymoma TABLE 1-continued

MALIGNANCIES AND RELATED DISORDERS pinealoma
hemangioblastoma
acoustic neuroma
oligodendroglioma
menangioma
melanoma
neuroblastoina
retinoblastoma In specific embodiments, malignancy or dysproliferative changes (such as metaplasias and dysplasias), or hyperproliferative disorders, are treated or prevented in the bladder, breast, colon, lung, melanoma, pancreas, or uterus.

5.5.2 Premalignant Conditions

The Therapeutics of the invention that are effective in treating cancer or malignancies (e.g., as described above) can also be administered to treat premalignant conditions and to prevent progression to a neoplastic or malignant state, including but not limited to those disorders listed in Table Such prophylactic or therapeutic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68–79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult cell or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a Therapeutic of the invention that modulates CDK2:CDK2-IP complex activity, or hsReq*-1 or hsReq*-2 activity. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also Robbins and Angell, 1976, Basic Pathology, 2d Ed., W.B. Saunders Co., Philadelphia, at pp. 84–90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

In other embodiments, a patient that exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W.B. Saunders Co., Philadelphia, pp. 112–113) etc.

In another specific embodiment, a Therapeutic of the invention is administered to a human patient to prevent progression to breast, colon, lung, pancreatic, or uterine cancer, or melanoma or sarcoma.

5.5.3 Hyperproliferative and Dysproliferative Disorders

In another embodiment of the invention, a Therapeutic is administered to treat or prevent hyperproliferative or benign dysproliferative disorders. Therapeutics of the invention can be assayed by any method known in the art for efficacy in treating or preventing hyperproliferative diseases or disorders, such assays include in vitro cell proliferation assays, in vitro or in vivo assays using animal models of hyperproliferative diseases or disorders, or any of the assays described in Sections 5.6 infra. Potentially effective Therapeutics, for example but not limited to, promote cell proliferation in culture or cause growth or cell proliferation in animal models in comparison to controls.

Accordingly, once a hyperproliferative disorder has been shown to be amenable to treatment by modulation of CDK2:CDK2-IP complex activity, or hsReq*-1 or hsReq*-2 activity, that hyperproliferative disease or disorder can be treated or prevented by administration of a Therapeutic that modulates CDK2:CDK2-IP complex formation (including supplying CDK2:CDK2-IP complexes and the individual binding partners of a CDK2:CDK2-IP complex, e.g., CDK2, cyclin H, cyclin I, ERH, hsReq*-1 and hsReq*-2).

Specific embodiments are directed to treatment or prevention of cirrhosis of the liver (a condition in which scarring has overtaken normal liver regeneration processes), treatment of keloid (hypertrophic scar) formation (disfiguring of the skin in which the scarring process interferes with normal renewal), psoriasis (a common skin condition characterized by excessive proliferation of the skin and delay in proper cell fate determination), benign tumors, fibrocystic conditions, and tissue hypertrophy (e.g., prostatic hyperplasia).

5.5.4 Neurodegenerative Disorders

CDK2 and certain binding partners of CDK2 (e.g., cyclin H, cyclin I, hsReq*-1 and hsReq*-2) have been implicated in the deregulation of cellular maturation and apoptosis, which are characteristic of neurodegenerative disease. Accordingly, Therapeutics of the invention, particularly those that modulate (or supply) CDK2:cyclin H, CDK2:cyclin I, CDK2: hsReq*-1 or CDK2: hsReq*-2 complexes maybe effective in treating or preventing neurodegenerative disease. Therapeutics of the invention (particularly those that modulate the levels or activity of CDK2:cyclin H, CDK2:cyclin I, CDK2:hsReq*-1 or CDK2:hsReq*-2 complexes) can be assayed by any method known in the art for efficacy in treating or preventing such neurodegenerative diseases and disorders, such assays include in vitro assays for regulated cell maturation or inhibition of apoptosis or in vivo assays using animal models of neurodegenerative diseases or disorders, or any of the assays described in Sections 5.6 infra. Potentially effective Therapeutics, for example but not by way of limitation, promote regulated cell maturation and prevent cell apoptosis in culture or reduce neurodegeneration in animal models in comparison to controls.

Once a neurodegenerative disease or disorder has been shown to be amenable to treatment by modulation of CDK2:CDK2-IP complex activity or hsReq*-1 or hsReq*-2 activity, that neurodegenerative disease or disorder can be treated or prevented by administration of a Therapeutic that modulates CDK2:CDK2-IP complex formation (including supplying CDK2:CDK2-IP complexes, e.g., CDK2:cyclin H, CDK2:cyclin I, CDK2:hsReq*-1 or CDK2:hsReq*-2 function).

Neurodegenerative disorders that can be treated or prevented include but are not limited to those listed in Table 2 (see Isslebacher et al., 1997, in: Harrison's Principals of Internal Medicine, 13th Ed., McGraw Hill, New York).

TABLE 2

NEURODEGENERATIVE DISORDERS

Progressive dementia in the absence of other neurological signs

Alzheimer's Disease (or early-onset AD)
Senile dementia of the Alzheimer's type (or late onset AD)
Pick's Disease
Syndromes combining progressive dementia with prominent neurological abnormalities Huntington's disease
Multiple system atrophy (dementia combined with ataxia, Parkinson's disease, etc.)
Progressive supranuclear palsy
Diffuse Lewy body disease
Corticodentatonigral degeneration
Hallervorden-Spatz disease
Progressive familial myoclonic epilepsy
Syndromes of gradually developing abnormalities of posture and movement Parkinson's disease
Striatonigral degeneration
Progressive supranuclear palsy
Torsion dystonia TABLE 2-continued

NEURODEGENERATIVE DISORDERS

Spasmodic torticollis and other restricted dyskinesias
Familial tremor
Gilles de la Tourette syndrome
Syndromes of progressive ataxia
Cerebeliar cortical degeneration Olivopontocerebellar atrophy
Friedrich's ataxia and related spinocerebellar degenerations
Shy-Drager syndrome
Subacute necrotizing encephalopathy
Motor neuron disease without sensory changes
Amyotrophic lateral sclerosis
Infantile spinal muscular atrophy
Juvenile spinal muscular atrophy
Other forms of familial spinal muscular atrophy
Primary lateral sclerosis
Hereditary spastic paraplegia
Motor neuron disease with sensory changes
Peroneal muscular atrophy
Hypertrophic interstitial polyneuropathy
Other forms of chronic progressive neuropathy
Syndromes of progressive visual loss
Retinitis pigmentosa

5.5.5 Cardiovascular Disease

CDK2 has been implicated in cardiovascular disorders, including intimal hyperplasia, the initial step in atherosclerotic plaque formation and in neovascularization seen in myocardial ischemia. All diseases shown in Table 3, infra, are, either directly or indirectly, associated with atherosclerosis. Accordingly, Therapeutics of the invention, particularly those that modulate (or supply) CDK2:CDK2-IP complex activity, may be effective in treating or preventing atherosclerosis-associated diseases or disorders. Therapeutics of the invention (particularly Therapeutics that modulate the levels or activity or CDK2:CDK2-IP) can be assayed by any method known in the art, including those described in Section 5.6, infra, for efficacy in treating or preventing such diseases and disorders.

A vast array of animal and cell culture models exist for processes involved in atherosclerosis. A limited and non-exclusive list of animal models includes knockout mice for premature atherosclerosis (Kurabayashi and Yazaki, 1996, Int. Angiol. 15:187–194), transgenic mouse models of atherosclerosis (Kappel et al., 1994, FASEB J. 8:583–592), antisense oligonucleotide treatment of animal models (Callow, 1995, Curr. Opin. Cardiol. 10:569–576), transgenic rabbit models for atherosclerosis (Taylor, 1997, Ann. N.Y. Acad. Sci 811:146–152), hypercholesterolemic animal models (Rosenfeld, 1996, Diabetes Res. Clin. Pract. 30 Suppl.:1–11), hyperlipidemic mice (Paigen et al., 1994, Curr. Opin. Lipidol. 5:258–264), and inhibition of lipoxygenase in animals (Sigal et al., 1994, Ann. N.Y. Acad. Sci. 714:211–224). In addition, in vitro cell models include but are not limited to monocytes exposed to low density lipoprotein (Frostegard et al., 1996, Atherosclerosis 121:93–103), cloned vascular smooth muscle cells (Suttles et al., 1995, Exp. Cell Res. 218:331–338), endothelial cell-derived chemoattractant exposed T cells (Katz et al., 1994, J. Leukoc. Biol. 55:567–573), cultured human aortic endothelial cells (Farber et al., 1992, Am. J. Physiol. 262: H1088–1085), and foam cell cultures (Libby et al., 1996, Curr Opin Lipidol 7:330–335). Potentially effective Therapeutics, for example but not by way of limitation, reduce foam cell formation in cell culture models, or reduce atherosclerotic plaque formation in hypercholesterolemic mouse models of atherosclerosis responses in animal models in comparison to controls.

Accordingly, once an atherosclerosis-associated disease or disorder has been shown to be amenable to treatment by modulation of CDK2:CDK2-IP complex activity, that disease or disorder can be treated or prevented by administration of a Therapeutic that modulates CDK2:CDK2-IP complex formation (including supplying CDK2:CDK2-IP complexes).

Diseases associated with atherosclerosis that can be treated or prevented include but are not limited to those listed in Table 3 (see Isslebacher et al., 1997, in Harrison's Principals of Internal Medicine, 13th Ed., McGraw Hill, New York, p.1107).

TABLE 3

DISEASES ASSOCIATED WITH ATHEROSCLEROSIS

Cardiovascular disease

Cerebral thrombosis
Cerebral hemorrhage
Ischemic heart disease
Peripheral vascular disease
Ischemic renal disease
Thrombosis of other major vessels
Other Diabetes mellitus
Hypertension
Familial hypercholesterolemia
Familal combined hyperlipidemia
Familial dysbetalipoproteinemia
Familial hypoalphalipoproteinemia
Hypothyroidism
Cholesterol ester storage disease
systemic lupus erythematosis
Homocysteinemia

5.5.6 Gene Therapy

In a specific embodiment, nucleic acids comprising a sequence encoding a CDK2 and/or a CDK2-IP, or hsReq*-1 or hsReq*-2, or functional derivatives thereof, are administered to modulate CDK2:CDK2-IP complex or hsReq*-1 or hsReq*-2 function, by way of gene therapy. In more specific embodiments, a nucleic acid or nucleic acids encoding both CDK2 and a CDK2-IP (e.g., cyclin H, cyclin I, ERH, hsReq*-1 or hsReq*-2) or functional derivatives thereof, are administered by way of gene therapy. Gene therapy refers to therapy performed by the administration of a nucleic acid to a subject. In this embodiment of the invention, the nucleic acid produces its encoded protein(s) that mediates a therapeutic effect by modulating CDK2:CDK2-IP complex, or hsReq*-1 or hsReq*-2, function.

Any of the methods for gene therapy available in the art can be used according to the present invention. Exemplary methods are described below.

For general reviews of the methods of gene therapy, see Goldspiel et al., 1993, Clinical Pharmacy 12: 488–505; Wu and Wu, 1991, Biotherapy 3: 87–95; Tolstoshev, 1993, Ann. Rev. Pharmacol. Toxicol. 32: 573–596; Mulligan, 1993, Science 260: 926–932; and Morgan and Anderson, 1993, Ann. Rev. Biochem. 62: 191–217; May, 1993, TIBTECH 11: 155–215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the Therapeutic comprises a CDK2 and a CDK2-IP nucleic acid, or hsReq*-1 or hsReq*-2 nucleic acid that is part of an expression vector that expresses the proteins CDK2 and a CDK2-IP or expresses hsReq*-1 or hsReq*-2, or fragments or chimeric proteins thereof in a suitable host. In particular, such a nucleic acid has a promoter operably linked to the CDK2 and the CDK2-IP coding region(s) (or, less preferably two separate promoters linked to the CDK2 and the CDK2-IP coding regions separately), or linked to the hsReq*-1 or hsReq*-2 coding region, said promoter being inducible or constitutive, and, optionally, tissue-specific. In another particular embodiment, a nucleic acid molecule is used in which the CDK2 and CDK2-IP coding sequences or hsReq*-1 or hsReq*-2 coding sequences, and any other desired sequences, are flanked by regions that promote homologous recombination at a desired site in the genome, thus providing for intra-chromosomal expression of the CDK2 and the CDK2-IP nucleic acids, or hsReq*-1 or hsReq*-2 nucleic acids (Koller and Smithies, 1989, Proc. Natl. Acad. Sci. USA 86:8932–8935; Zijlstra et al., 1989, Nature 342:435–438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol. Chem. 262:4429–4432) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.); WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, a viral vector that contains the CDK2 and/or the CDK2-IP nucleic acids or hsReq*-1 or hsReq*-2 nucleic acid is used. For example, a retroviral vector can be used (see Miller et al., 1993, Meth. Enzymol. 217:581–599). These retroviral vectors have been modified to delete retroviral sequences that are not necessary for packaging of the viral genome and integration into host cell DNA. The CDK2 and/or CDK2-IP (preferably both CDK2 and CDK2-IP) nucleic acids, or hsReq*-1 or hsReq*-2 nucleic acids, to be used in gene therapy is/are cloned into the vector, which facilitates delivery of the gene into a patient. More detail about retroviral vectors can be found in Boesen et al., 1994, Biotherapy 6: 291–302, which describes the use of a retroviral vector to deliver the mdr1 gene to hematopoetic stem cells in order to make the stem cells more resistant to chemotherapy. Other references illustrating the use of retroviral vectors in gene therapy are: Clowes et al., 1994, J. Clin. Invest. 93: 644–651; Kiem et al., 1994, Blood 83: 1467–1473; Salmons and Gunzberg, 1993, Human Gene Therapy 4: 129–141; and Grossman and Wilson, 1993, Curr. Opin. in Genetics and Devel. 3: 110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson (1993, Current Opinion in Genetics and Development 3: 499–503) present a review of adenovirus-based gene therapy. Bout et al. (1994, Human Gene Therapy 5: 3–10) demonstrated the use of adenovirus vectors to transfer genes to the respiratory epithelia of rhesus monkeys. Other instances of the use of adenoviruses in gene therapy can be found in Rosenfeld et al., 1991, Science 252: 431–434; Rosenfeld et al., 1992, Cell 68: 143–155; and Mastrangeli et al., 1993, J. Clin. Invest. 91: 225–234.

Adeno-associated virus (AAV) has also been proposed for use in gene therapy (Walsh et al., 1993, Proc. Soc. Exp. Biol. Med. 204: 289–300.

Another approach to gene therapy involves transferring a gene into cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217: 599–618; Cohen et al., 1993, Meth. Enzymol. 217: 618–644; Cline, 1985, Pharmac. Ther. 29: 69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoetic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoetic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, a CDK2 and/or a CDK2-IP (preferably both a CDK2 and a CDK2-IP) nucleic acid or hsReq*-1 or hsReq*-2 nucleic acid is/are introduced into the cells such that the gene or genes are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention. Such stem cells include but are not limited to hematopoetic stem cells (HSC), stem cells of epithelial tissues such as the skin and the lining of the gut, embryonic heart muscle cells, liver stem cells (PCT Publication WO 94/08598, dated Apr. 28, 1994), and neural stem cells (Stemple and Anderson, 1992, Cell 71: 973–985).

Epithelial stem cells (ESCs) or keratinocytes can be obtained from tissues such as the skin and the lining of the gut by known procedures (Rheinwald, 1980, Meth. Cell Bio. 2A: 229). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture (Rheinwald, 1980, Meth. Cell Bio. 2??: 229; Pittelkow and Scott, 1986, Mayo Clinic Proc. 61: 771). If the ESCs are provided by a donor, a method for suppression of host versus graft reactivity (e.g., irradiation, drug or antibody administration to promote moderate immunosuppression) can also be used.

With respect to hematopoetic stem cells (HSC), any technique which provides for the isolation, propagation, and maintenance in vitro of HSC can be used in this embodiment of the invention. Techniques by which this may be accomplished include (a) the isolation and establishment of HSC cultures from bone marrow cells isolated from the future host, or a donor, or (b) the use of previously established long-term HSC cultures, which may be allergenic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see, e.g., Kodo et al., 1984, J. Clin. Invest. 73: 1377–1384). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, J. Cell Physiol. 91: 335) or Witlock-Witte culture techniques (Witlock and Witte, 1982, Proc. Natl. Acad. Sci. USA 79: 3608–3612).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Additional methods can be adapted for use to deliver a nucleic acid encoding the CDK2 and/or CDK2-IP proteins or hsReq*-1 or hsReq*-2 proteins, or functional derivatives thereof, e.g., as described in Section 5.8 supra.

5.5.7 Use of Antisense Oligonucleotides for Suppression of CDK2:CDK2-IP Complexes and hsREQ*-1 OR hsREQ*-2

In a specific embodiment, CDK2:CDK2-IP complex function or hsReq*-1 or hsReq*-2 protein function is inhibited by use of antisense nucleic acids for CDK2 and/or a CDK2-IP (e.g., cyclin H, cyclin I, ERH, hsReq*-1 or hsReq*-2) (preferably both CDK2 and the CDK2-IP) or antisense nucleic acids for hsReq*-1 or hsReq*-2. The present invention provides the therapeutic or prophylactic use of nucleic acids of at least six nucleotides that are antisense to a gene or cDNA encoding CDK2 and/or a CDK2-IP or encoding hsReq*-1 or hsReq*-2, or portions thereof. A CDK2, CDK2-IP, hsReq*-1 or hsReq*-2 "antisense" nucleic acid as used herein refers to a nucleic acid capable of hybridizing to a portion of a CDK2 or CDK2-IP RNA (preferably mRNA) by virtue of some sequence complementarity. The antisense nucleic acid may be complementary to a coding and/or noncoding region of a CDK2, CDK2-IP, hsReq*-1 or hsReq*-2 mRNA. However, preferably the hsReq*-1 and hsReq*-2 antisense nucleic acids hybridize to the portion of the hsReq*-1 or hsReq*-2 sequence containing the alternate splice junction and do not hybridize to the hsReq coding sequence. Such antisense nucleic acids have utility as Therapeutics that inhibit CDK2:CDK2-IP complex formation or activity, or hsReq*-1 or hsReq*-2 function or activity, and can be used in the treatment or prevention of disorders as described supra.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

In another embodiment, the invention is directed to methods for inhibiting the expression of CDK2 and a CDK2-IP nucleic acid sequences, or hsReq*-1 or hsReq*-2 nucleic acid sequence in a prokaryotic or eukaryotic cell comprising providing the cell with an effective amount of a composition comprising an antisense nucleic acid of CDK2 and CDK2-IP, or an antisense nucleic acid of hsReq*-1 or hsReq*-2, or derivatives thereof, of the invention.

The CDK2 and CDK2-IP antisense nucleic acids are of at least six nucleotides and are preferably oligonucleotides (ranging from 6 to about 200 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86: 6553–6556; Lemaitre et al., 1987, Proc. Natl. Acad. Sci. 84: 648–652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6: 958–976) or intercalating agents (see, e.g., Zon, 1988, Pharm. Res. 5: 539–549).

In a preferred aspect of the invention, a CDK2 and/or CDK2-IP antisense oligonucleotide or a hsReq*-1 or hsReq*-2 antisense oligonucleotide is provided, preferably as single-stranded DNA. The oligonucleotide may be modified at any position on its structure with constituents generally known in the art.

The CDK2, CDK2-IP, hsReq*-1 and hsReq*-2 antisense oligonucleotides may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5N-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an 2-α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15: 6625–6641).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16: 3209), methylphosphonate oligonucleotides can be prepared by use of controlled pore glass polymer supports (Sarin et al., 1988, Proc. Natl. Acad. Sci. U.S.A. 85: 7448–7451), etc.

In a specific embodiment, the CDK2 and CDK2-IP antisense oligonucleotides comprise catalytic RNAs, or ribozymes (see, e.g., PCT International Publication WO 90/11364, published Oct. 4, 1990; Sarver et al., 1990, Science 247: 1222–1225). In another embodiment, the oligonucleotide is a 2N-O-methylribonucleotide (Inoue et al., 1987, Nucl. Acids Res. 15: 6131–6148), or a chimeric RNA-DNA analog (Inoue et al., 1987, FEBS Lett. 215: 327–330). In an alternative embodiment, the CDK2 and CDK2-IP antisense nucleic acids of the invention are produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding a CDK2 and/or CDK2-IP anti-sense nucleic acid (preferably, a CDK2 and a CDK2-IP anti-sense nucleic acid), or individual hsReq*-1 or hsReq*-2 antisense nucleic acids. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequences encoding the CDK2 and CDK2-IP antisense RNAs can be by any promoter known in the art to act in mammalian, preferably human, cells. Such promoters can be inducible or constitutive. Such promoters include but are not limited to: the SV40 early promoter region (Bernoist and Chambon, 1981, Nature 290: 304–310), the promoter contained in the 3' long terminal repeat of Rous sarcoma virus (Yamamoto et al., 1980, Cell 22: 787–797), the herpes thymidine kinase promoter (Wagner et al., 1981, Proc. Natl. Acad. Sci. U.S.A. 78: 1441–1445), the regulatory sequences of the metallothionein gene (Brinster et al., 1982, Nature 296: 39–42), etc.

The antisense nucleic acids of the invention comprise a sequence complementary to at least a portion of an RNA transcript of a CDK2 and CDK2-IP gene, preferably a human CDK2 or CDK2-IP gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded CDK2 or CDK2-IP antisense nucleic acids, a single strand of the duplex DNA may thus be tested, or triplex formation may be assayed. The ability to hybridize will depend on both the degree of complementarity and the length of the antisense nucleic acid.

Generally, the longer the hybridizing nucleic acid, the more base mismatches with a CDK2 or CDK2-IP RNA it may contain and still form a stable duplex (or triplex, as the case may be). One skilled in the art can ascertain a tolerable degree of mismatch by use of standard procedures to determine the melting point of the hybridized complex.

The CDK2 and CDK2-IP antisense nucleic acid can be used to treat (or prevent) disorders of a cell type that expresses, or preferably overexpresses, the CDK2:CDK2-IP complex, or hsReq*-1 or hsReq*-2 protein. In a preferred embodiment, a CDK2 and CDK2-IP single stranded antisense nucleic acid or antisense oligonucleotide, or hsReq*-1 or hsReq*-2 antisense oligonucleotide or single-stranded antisense nucleic acid, is used.

Cell types that express or overexpress CDK2 and CDK2-IP RNA, or hsReq*-1 or hsReq*-2 RNA can be identified by various methods known in the art. Such methods include, but are not limited to, hybridization with CDK2- and CDK2-IP-specific nucleic acids (e.g. by northern hybridization, dot blot hybridization, in situ hybridization), or by observing the ability of RNA from the cell type to be translated in vitro into CDK2 and the CDK2-IP by immunohistochemistry. In a preferred aspect, primary tissue from a patient can be assayed for CDK2 and/or CDK2-IP expression prior to treatment, e.g., by immunocytochemistry or in situ hybridization.

Pharmaceutical compositions of the invention (see Section 5.8 infra), comprising an effective amount of a CDK2 and a CDK2-IP antisense nucleic acid in a pharmaceutically acceptable carrier can be administered to a patient having a disease or disorder which is of a type that expresses or overexpresses CDK2:CDK2-IP complexes or hsReq*-1 or hsReq*-2 RNA or protein.

The amount of CDK2 and/or CDK2-IP antisense nucleic acid that will be effective in the treatment of a particular disorder or condition will depend on the nature of the disorder or condition, and can be determined by standard clinical techniques. Where possible, it is desirable to determine the antisense cytotoxicity in vitro, and then in useful animal model systems prior to testing and use in humans.

In a specific embodiment, pharmaceutical compositions comprising CDK2 and CDK2-IP antisense nucleic acids are administered via liposomes, microparticles, or microcapsules. In various embodiments of the invention, it may be useful to use such compositions to achieve sustained release of the CDK2 and/or CDK2-IP antisense nucleic acids. In a specific embodiment, it may be desirable to utilize liposomes targeted via antibodies to specific identifiable central nervous system cell types (Leonetti et al., 1990, Proc. Natl. Acad. Sci. U.S.A. 87: 2448–2451; Renneisen et al., 1990, J. Biol. Chem. 265: 16337–16342).

5.6 Assays of CDK2:CDK2-IP Complexes, hsREQ*-1 and hsREQ*-2 and Derivatives and Analogs The functional activity of CDK2:CDK2-IP complexes and hsReq*-1 or hsReq*-2 proteins, and derivatives, fragments and analogs thereof can be assayed by various methods. Potential modulators (e.g., inhibitors, agonists and antagonists) of CDK2:CDK2 complex activity, or hsReq*-1 or hsReq*-2 activity, e.g., anti-CDK2:CDK2-IP complex, anti-hsReq*-1 or anti-hsReq*-2 antibodies, and CDK2, CDK2-IP, hsReq*-1 or hsReq*-2 antisense nucleic acids, can be assayed for the ability to modulate CDK2:CDK2-IP complex formation and/or activity or hsReq*-1 or hsReq*-2 level or activity.

For example, in one embodiment, where one is assaying for the ability to bind or compete with wild-type CDK2:CDK2-IP complexes or hsReq*-1 or hsReq*-2 for binding to anti-CDK2:CDK2-IP antibody or anti-hsReq*-1 or anti-hsReq*-2 antibodies, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by assaying a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

The expression of the CDK2, CDK2-IP, hsReq*-1 or hsReq*-2 genes (both endogenous genes and those expressed from cloned DNA containing these genes) can be detected using techniques known in the art, including but not limited to Southern hybridization (Southern, 1975, J. Mol. Biol. 98: 503–517), Northern hybridization (e.g. Freeman et al., 1983, Proc. Natl. Acad. Sci. USA 80: 4094–4098), restriction endonuclease mapping (Sambrook et al., 1982, Molecular Cloning, A Laboratory Manual, Cold Spring Harbor Laboratory Press, New York), and DNA sequence analysis. Polymerase chain reaction amplification (PCR; U.S. Pat. Nos. 4,683,202, 4,683,195, and 4,889,818; Gyllenstein et al., 1988, Proc. Natl. Acad. Sci. USA 85: 7652–7657; Ochman et al., 1988, Genetics 120: 621–623; Loh et al., 1989, Science 243: 217–220) followed by Southern hybridization or RNase protection (Current Protocols in Molecular Biology, John Wiley and Sons, New York, 1997) with probes specific for CDK2 and the CDK2-IP genes in various cell types. Methods of amplification, other than PCR, commonly known in the art can be employed. In one embodiment, Southern hybridization can be used to detect genetic linkage of CDK2 and/or CDK2-IP gene mutations to physiological or pathological states. Various cell types, at various stages of development, can be characterized for their expression of CDK2 and a CDK2-IP (particularly expression of CDK2 and CDK2-IP at the same time and in the same cells), or hsReq*-1 or hsReq*-2 expression. The stringency of the hybridization conditions for northern or Southern blot analysis can be manipulated to ensure detection of nucleic acids with the desired degree of relatedness to the specific probes used. Modifications to these methods and other methods commonly known in the art can be used.

Derivatives (e.g., fragments) and analogs of CDK2-IPs, including cyclin H, cyclin I, ERH, hsReq*-1 or hsReq*-2 (and fragments and other derivatives and analogs of CDK2-IPs) can be assayed for binding to CDK2 by any method known in the art, for example by the modified yeast two hybrid assay system described in Section 5.7.1 infra, immunoprecipitation with an antibody that binds to CDK2 in a complex followed by analysis by size fractionation of the immunoprecipitated proteins (e.g. by denaturing or nondenaturing polyacrylamide gel electrophoresis), Western analysis, non-denaturing gel electrophoresis, etc.

One embodiment of the invention provides a method for screening a derivative or analog of CDK2 for biological activity comprising contacting said derivative or analog of CDK2 with a protein selected from the group consisting of cyclin H, cyclin I, ERH, hsReq*-1 and hsReq*-2; and detecting the formation of a complex between said derivative or analog of CDK2 and said protein; wherein detecting formation of said complex indicates that said derivative or analog of CDK2 has biological (e.g., binding) activity.

Additionally, another embodiment of the invention relates to a method for screening a derivative or analog of a protein selected from the group consisting of cyclin H, cyclin I, ERH, hsReq*-1 and hsReq*-2 for biological activity comprising contacting said derivative or analog of said protein with CDK2; and detecting the formation of a complex between said derivative or analog of said protein and CDK2; wherein detecting the formation of said complex indicates that said derivative or analog of said protein has biological activity.

The invention also provides methods of modulating the activity of a protein that can participate in a CDK2:CDK2-IP complex (e.g. CDK2, cyclin H, cyclin I, ERH, hsReq*-1 and hsReq*-2) by administration of a binding partner of that protein or derivative or analog thereof. CDK2, and derivatives and analogs thereof, can be assayed for the ability to modulate the activity or levels of a CDK2-IP by contacting a cell or administering an animal expressing a CDK2-IP gene with a CDK2 protein, or a nucleic acid encoding a CDK2 protein or an antibody that immunospecifically binds the CDK2 protein or a fragment or derivative of said antibody containing the binding domain thereof and measuring a change in CDK2-IP levels or activity, wherein a change in CDK2-IP levels or activity indicates that CDK2 can modulate CDK2-IP levels or activity. Alternatively, a CDK2-IP can be assayed for the ability to modulate the activity or levels of a CDK2 protein by contacting a cell or administering an animal expressing a gene encoding said protein with CDK2, or a nucleic acid encoding CDK2, or an antibody that immunospecifically binds CDK2, or a fragment or derivative of said antibody containing the binding domain thereof, wherein a change in CDK2 levels or activity indicates that the CDK2-IP can modulate CDK2 levels or activity.

CDK2, and several of the identified binding partners of CDK2, e.g., cyclin H and cylin I, have roles in the control of cell proliferation and, therefore, cell-transformation and tumorigenesis. Accordingly, methods of the invention are provided for screening CDK2:CDK2-IP complexes and the individual binding partners and fragments, derivatives and analogs of the foregoing, for activity in altering cell proliferation, cell transformation and/or tumorigenesis in vitro and in vivo.

The CDK2:CDK2-IP complexes and the individual binding partners and derivatives, fragments, and analogs thereof, can be assayed for activity to alter (i.e., increase or decrease) cell proliferation in cultured cells in vitro using methods which are well known in the art for measuring cell proliferation.

For example, but not by way of limitation, cell proliferation can be assayed by measuring $^3$H-thymidine incorporation, by direct cell count, by detecting changes in transcriptional activity of known genes such as proto-oncogenes (e.g., fos, myc) or cell cycle markers, etc. Accordingly, one embodiment of the invention provides a method of screening CDK2:CDK2-IP complexes and individual binding partners and fragments, derivatives, and analogs thereof, for activity in altering (i.e., increasing or decreasing) proliferation of cells in vitro comprising contacting the cells with a CDK2:CDK2-IP complex and individual binding partner or derivative, analog, or fragment thereof, measuring the proliferation of cells that have been so contacted, and comparing the proliferation of the cells so contacted with a complex or protein of the invention with the proliferation of cells not so contacted with the complex or protein of the invention, wherein in a change in the level of proliferation in said contacted cells indicates that the complex or protein of the invention has activity to alter cell proliferation.

The CDK2:CDK2-IP complexes and individual binding partners and derivatives, fragments and analogs, thereof, can also be screened for activity in inducing or inhibiting cell transformation (or progression to malignant phenotype) in vitro. The complexes and proteins of the invention can be screened by contacting either cells with a normal phenotype (for assaying for cell transformation) or a transformed cell phenotype (for assaying for inhibition of cell transformation) with the complex or protein of the invention and examining the cells for acquisition or loss of characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, General Virology, 3d Ed., John Wiley & Sons, New York, pp. 436–446).

The CDK2:CDK2-IP complexes, and hsReq*-1 and hsReq*-2 proteins, and derivatives, fragments, and analogs thereof can also be screened for activity to promote or inhibit tumor formation in vivo in non-human test animal. A vast number of animal models of hyperproliferative disorders, including tumorigenesis and metastatic spread, are known in the art (see Table 317-1, Chapter 317, "Principals of Neoplasia," in Harrison's Principals of Internal Medicine, 13th Edition, Isselbacher et al., eds., McGraw-Hill, New York, p.1814; Lovejoy et al., 1997, J. Pathol. 181:130–135). Specific examples include: transplantation of tumor modules into rats for lung cancer (Wang et al., 1997, Ann. Thorac. Surg. 64:216–219) or establishment of lung cancer metastases in SCID mice depleted of NK cells (Yono and Sone, 1997, Gan To Kagaku Ryoho, 24:489–494); colon cancer transplantation of human colon cancer cells into nude mice (Gutman and Fidler, 1995, World J. Surg., 19:226–234), the cotton top tamarin model of human ulcerative colitis (Warren, 1996, Aliment. Pharmacol. Ther., 10 Suppl2:45–47) and mouse models with mutations of the adenomatous polyposis coli tumor suppressor (Polakis, 1997, Biochim. Biophys. Acta 1332: F127–F147); for breast cancer, transgenic models of breast cancer (Dankort and Muller, 1996, Cancer Treat. Res. 83:71–88; Amundadittir et al., 1996, Breast Cancer Res. Treat. 39:119–135) and chemical induction of tumors in rats (Russo and Russo, 1996, Breast Cancer Res. Treat. 39:7–20); for prostate cancer, chemically-induced and transgenic rodent models, and human xenograft models (Royai et al., 1996, Semin. Oncol. 23:35–40); for genitourinary cancers, induced bladder neoplasm in rats and mice (Oyasu, 1995, Food Chem. Toxicol 33:747–755) and xenografts of human transitional cell carcinomas into nude rats (Jarrett et al., 1995, J. Endourol. 9:1–7); for hematopoietic cancers, transplanted allogeneic marrow in animals (Appelbaum, 1997, Leukemia 11 Suppl 4:S 15–S17). Further, general animal models applicable to many types of cancer have been described, including but not restricted to the p53-deficient mouse model (Donehower, 1996, Semin. Cancer Biol. 7:269–278), the Min mouse (Shoemaker et al., 1997, Biochem. Biophys. Acta, 1332:F25–F48), and immune response to tumors in the rat (Frey, 1997, Methods, 12:173–188).

For example, the complexes and proteins of the invention can be administered to a non-human test animal (preferably a test animal predisposed to develop a type of tumor) and the non-human test animals subsequently examined for an increased incidence of tumor formation in comparison with controls not administered the complex or protein of the invention. Alternatively, the complexes and proteins of the invention can be administered to non-human test animals having tumors (e.g., animals in which tumors have been induced by introduction of malignant, neoplastic, or transformed cells or by administration of a carcinogen) and subsequently examining the tumors in the test animals for tumor regression in comparison to controls.

The CDK2:CDK2-IP complexes and individual members of the complexes, and derivatives, analogs, and fragments thereof, can also be screened for activity in modulating the activity of other CDK2 binding partners (i.e., the CDK2-IPs, particularly cyclin H, cyclin I, ERH, hsReq*-1 or hsReq*-2) involved in particular CDK2:CDK2-IP complexes. For example, CDK2 has been shown to bind the CDK2 kinase inhibitors $p_{21}^{waf}$ and $p27^{kip}$ (Adams et al. 1996, Mol. Cell. Biol. 16:6623–6633). Accordingly, complexes and proteins of the invention can be screened for the ability to modulate (i.e. increase or decrease) $p21^{waf}$ and $p27^{kip}$ effects on critical cell cycle proteins, including p53, cyclin A, etc. (Higashi et al., 1996, Eur. J. Biochem. 237:460–467). Similarly, CDK2 itself interacts with retinoblastoma protein, p53, the transcription factor E2F, histone H1, and other proteins central to cell cycle control (Higashi et al., 1996, Eur. J. Biochem. 237:460–467). Thus, the complexes and proteins of the invention can be screened by assaying for changes in the level of p53 phosphorylation, retinoblastoma protein phosphorylation, etc. (e.g., as described in Milne et al., 1994, J. Biol. Chem. 269:9253–9260) or the level of CDK2 binding to histone H1 (e.g., by methods described supra).

Cyclin H is centrally implicated in control of cell cycle progression. CAK is also associated with the mammalian transcription factor IIH (TFIIH), a multisubunit complex that is required for transcription and DNA nucleotide excision repair (Drapkin et al., 1996, Proc. Natl. Acad. Sci. USA 93: 6488–6493). Therefore, the role of cyclin H extends beyond cell cycle control to include coordination of the progression of the cell cycle with transcription and DNA repair. Dysfunction of TFIIH is implicated in various genetic disorders including xeroderma pigmentosum, Cockayne's syndrome and trichothiodystrophy (Seroz et al., 1995, Curr. Opin. Genet. Dev. 5: 217–222). Thus, both CDK2:CDK2-IP complexes and individual CDK2-IPs (including CDK) can be screened by assaying for changes in levels of KAP or TFIIH (e.g., by immunoassays with anti-KAP or anti-TFIIH antibodies).

Cyclin I contains a typical cyclin box near the N-terminus, implicating it in control of cell cycle progression and transcriptional control (Gibson et al., 1994, Nucleic Acids Res. 22: 946–952). It also has a PEST domain proximal to its C-terminus, and thus, may be the target of rapid inactivation via ubiquitin-mediated proteolysis, as are most transcription factors (Rechsteiner, 1990, Semin. Cell Biol. 1: 433–440). Thus, CDK2 and CDK2-IPs can be screened for PEST domain binding, especially ubiquitin, e.g., using binding assays described supra.

ERH functions in the pyrimidine metabolic pathway, and has a putative role in development. ERH is thus implicated in transcriptional control, DNA pyrimidine metabolism, and in development. Again, CDK2 and CDK2-IP complexes can be screened by assays that measure metabolic markers for pyrimidine metabolism, rates of DNA synthesis etc., using methods commonly known in the biochemical arts.

CDK2, cyclin H, and hsReq are strongly implicated in neurodegenerative disorders. The CDK2:CDK2-IP complexes (particularly the CDK2:cyclin H, CDK2:hsReq*-1 and CDK2:hsReq*-2 complexes) and derivatives, analogs and fragments thereof, nucleic acids encoding the CDK2 and CDK2-IP genes, anti-CDK2:CDK2-IP antibodies, and other modulators of CDK2:CDK2-IP complex activity can be tested for activity in treating or preventing neurodegenerative disease in in vitro and in vivo assays.

In one embodiment, a Therapeutic of the invention can be assayed for activity in treating or preventing neurodegenerative disease by contacting cultured cells, such as but not limited to, cultured rat endothelial cells from affected and unaffected individual humans (Maneiro et al., 1997, Methods Find. Exp. Clin. Pharmacol., 19:5–12), that exhibit an indicator of a neurodegenerative disease in vitro with the Therapeutic; and comparing the level of said indicator in the cells contacted with the Therapeutic, with said level of said indicator in cells not so contacted, wherein a lower level in said contacted cells indicates that the Therapeutic has activity in treating or preventing neurodegenerative disease. Specific examples of such cultured models for neurodegenerative disease include, but are not limited to: cultured rat endothelial cells from affected and unaffected individual humans (Maneiro et al., 1997, Methods Find. Exp. Clin. Pharmacol., 19:5–12); P19 murine embryonal carcinoma cells (Hung et al., 1992, Proc Natl Acad Sci USA 1992, 89:9439–9443); and dissociated cell cultures of cholinergic neurons from nucleus basalis of Meynert (Nakajima et al., 1985, Proc Natl Acad Sci USA, 82:6325–6329).

In another embodiment, a Therapeutic of the invention can be assayed for activity in treating or preventing neurodegenerative disease by administering the Therapeutic to a test animal, such as but not limited to the PDAPP transgenic mouse model of Alzheimer disease (Johnson-Wood et al., 1997, Proc. Natl. Acad. Sci. USA 94:1550–1555), that exhibits symptoms of a neurodegenerative disease or that is predisposed to develop symptoms of a neurodegenerative disease; and measuring the change in said symptoms of the neurodegenerative disease after administration of said Therapeutic, wherein a reduction in the severity of the symptoms of the neurodegenerative or prevention of the symptoms of the neurodegenerative disease indicates that the Therapeutic has activity in treating or preventing neurodegenerative disease. Such a test animal can be any one of a number of animal models known in the art for neurodegenerative disease. These models include those for Alzheimer's Disease and mental retardation of trisomy 21 accurately mimic natural human autoimmune diseases (Farine, 1997, Toxicol. 119:29–35). Examples of specific models include but are not limited to: the partial trisomy 16 mouse (Holtzman et al., 1996, Proc. Natl. Acad. Sci. USA 93:13333–13338); bilateral nucleus basalis magnocellularis-lesioned rats (Popovic et al., 1996, Int. J. Neurosci. 86:281–299); the aged rat (Muir, 1997, Pharmacol. Biochem. Behav. 56:687–696); the PDAPP transgenic mouse model of Alzheimer disease (Johnson-Wood et al., 1997, Proc. Natl. Acad. Sci. USA 94:1550–1555); and experimental autoimmune dementia (Oron et al., 1997, J. Neural Transm. Suppl. 49:77–84).

CDK2 is clearly implicated in atherosclerosis and associated disorders, including but not limited to myocardial ischemia and thrombotic stroke. Accordingly, Therapeutics of the invention, particularly those that modulate (or supply) CDK2:CDK2-IP complex activity, may be effective in treating or preventing atherosclerosis-associated diseases or disorders. Therapeutics of the invention can be assayed by any method known in the art for efficacy in treating or preventing such diseases and disorders.

In one embodiment, a Therapeutic of the invention can be assayed for activity in treating or preventing atherosclerosis and associated diseases by contacting cultured cells, such as but not limited to, monocytes exposed to low density lipoprotein (Frostegard et al., 1996, Atherosclerosis 121:93–103), that exhibit an indicator of a atherosclerosis-associated disease in vitro with the Therapeutic; and comparing the level of said indicator in the cells contacted with the Therapeutic, with said level of said indicator in cells not so contacted, wherein a lower level in said contacted cells indicates that the Therapeutic has activity in treating or preventing atherosclerosis-associated disease. Specific examples of such cultured models for atherosclerosis and associated diseases include, but are not limited to: monocytes exposed to low density lipoprotein (Frostegard et al., 1996, Atherosclerosis 121:93–103), cloned vascular smooth muscle cells (Suttles et al., 1995, Exp. Cell Res. 218:331–338), endothelial cell-derived chemoattractant exposed T cells (Katz et al., 1994, J. Leukoc. Biol. 55:567–573), cultured human aortic endothelial cells (Farber et al., 1992, Am. J. Physiol. 262: H1088–1085), and foam cell cultures (Libby et al., 1996, Curr. Opin. Lipidol. 7:330–335).

In another embodiment, a Therapeutic of the invention can be assayed for activity in treating or preventing atherosclerosis-associated diseases by administering the Therapeutic to a test animal, such as but not limited to a transgenic mouse model of atherosclerosis (Kappel et al., 1994, FASEB J. 8:583–592), that exhibits symptoms of a atherosclerosis or that is predisposed to develop symptoms of an atherosclerosis-associated disease; and measuring the change in said symptoms of the atherosclerosis-associated disease after administration of said Therapeutic, wherein a reduction in the severity of the symptoms of the atherosclerosis-associated disease or prevention of the symptoms of the atherosclerosis-associated disease indicates that the Therapeutic has activity in treating or preventing atherosclerosis-associated disease. Such a test animal can be any one of a number of animal models known in the art for atherosclerosis-associated disease. A limited and non-exclusive list of animal models includes knockout mice for premature atherosclerosis (Kurabayashi and Yazaki, 1996, Int. Angiol. 15:187–194), transgenic mouse models of atherosclerosis (Kappel et al., 1994, FASEB J. 8:583–592), antisense oligonucleotide treatment of animal models (Callow, 1995, Curr. Opin. Cardiol. 10:569–576), transgenic rabbit models for atherosclerosis (Taylor, 1997, Ann. N.Y. Acad. Sci 811:146–152), hypercholesterolemic animal models (Rosenfeld, 1996, Diabetes Res. Clin. Pract. 30 Suppl.:1–11), hyperlipidemic mice (Paigen et al., 1994, Curr. Opin. Lipidol. 5:258–264), and inhibition of lipoxygenase in animals (Sigal et al., 1994, Ann. N.Y. Acad. Sci. 714:211–224).

Accordingly, once a hyperproliferative disease or disorder has been shown to be amenable to treatment by modulation of CDK2:CDK2-IP complex activity, in particular CDK2:cyclin H activity, that disease or disorder can be treated or prevented by administration of a Therapeutic that modulates CDK2:CDK2-IP complex formation (including supplying CDK2:CDK2-IP complexes), in a specific embodiment, CDK2:cyclin H is administered.

Similarly, once a neurodegeneration disease or disorder has been shown to be amenable to treatment by modulation of CDK2:CDK2-IP complex activity, in particular, CDK2:cyclin H, CDK2:hsReq*-1 and CDK2:hsReq*-2 activity, or hsReq*-1 and hsReq*-2 activity, that disease or disorder can be treated or prevented by administration of a Therapeutic that modulates CDK2:CDK2-IP complex formation (including supplying CDK2:CDK2-IP complexes), in a specific embodiment, CDK2:cyclin H, CDK2:hsReq*-1 ,or CDK2:hsReq*-2, or hsReq*-1 or hsReq*-2 are administered to treat or prevent atherosclerosis-associated diseases or disorders.

Similarly, once an atherosclerosis-associated disease or disorder has been shown to be amenable to treatment by modulation of CDK2:CDK2-IP complex activity, that disease or disorder can be treated or prevented by administration of a Therapeutic that modulates CDK2:CDK2-IP complex formation (including supplying CDK2:CDK2-IP complexes).

5.7 Screening for Antagonists and Agonists of CDK2:CDK2-IP Complexes, and hsREQ*-1 AND hsREQ*-2

CDK2:CDK2-IP complexes, and hsReq*-1 and hsReq*-2, and derivatives, fragments and analogs thereof, as well as nucleic acids encoding CDK2 and CDK2-IPs and hsReq*-1 and hsReq*-2, as well as derivatives, fragments and analogs thereof, can be used to screen for compounds that bind to CDK2:CDK2-IP and hsReq*-1 or hsReq*-2 nucleic acids, proteins, or derivatives, and thus have potential use as agonists or antagonists of CDK2:CDK2-IP complexes or hsReq*-1 and hsReq*-2 protein function. The invention thus provides assays to detect molecules that specifically bind to CDK2 and CDK2-IP complexes, and hsReq*-1 and hsReq*-2 nucleic acids, proteins or derivatives. For example, recombinant cells expressing both CDK2 and CDK2-IP nucleic acids, or hsReq*-1 and hsReq*-2 nucleic acids, can be used to produce, using recombinant techniques, the complexes or proteins in these assays, to screen for molecules that bind or interfere with CDK2:CDK2-IP complexes or hsReq*-1 and hsReq*-2 function. In preferred embodiments, polypeptide analogs that have superior stabilities (but retain the ability to form CDK2:CDK2-IP complexes), e.g. CDK2 and CDK2-IPs modified to be resistant to proteolytic degradation in the binding assay buffers, or to be resistant to oxidative degradation are used to screen for modulators. (e.g., molecules generated by substitution of amino acids at proteolytic cleavage sites, the use of chemically-derivatized amino acids at proteolytic susceptible sites, and replacement of amino acid residues subject to oxidation, i.e., methionine and cysteine).

Molecules (e.g. putative binding partners of a CDK2:CDK2-IP complex or of hsReq*-1 or hsReq*-2) are contacted with the CDK2:CDK2-IP complex or hsReq*-1 or hsReq*-2 proteins (or fragment thereof) under conditions conducive to binding, and then molecules that specifically bind to CDK2:CDK2-IP complexes or hsReq*-1 and hsReq*-2 proteins are identified. Similar methods can be used to screen for molecules that bind to CDK2:CDK2-IP complexes or hsReq*-1 and hsReq*-2 nucleic acids or derivatives.

A particular aspect of the invention relates to identifying molecules that inhibit or promote formation or degradation of a CDK2:CDK2-IP complex, e.g., using the method described for screening described for screening inhibitors using the modified yeast two hybrid assay described in Section 5.7.1., infra and in U.S. patent application Ser. No. 08/663,824, filed Jun. 14, 1996, and Ser. No. 08/874,825, filed Jun. 13, 1997, both entitled "Identification and Comparison of Protein—Protein Interactions that Occur in Populations and Identification of Inhibitors of These Interactions", and both by Nandabalan et al., which are incorporated by reference herein in their entireties.

In one embodiment of the invention, a molecule that modulates activity of CDK2 or a protein selected from the group consisting of cyclin H, cyclin I, ERH, hsReq*-1 or hsReq*-2, or a complex of CDK2 and said protein is identified by contacting one or more candidate molecules with CDK2 in the presence of said protein; and measuring the amount of complex that forms between CDK2 and said protein; wherein an increase or decrease in the amount of complex that forms relative to the amount that forms in the absence of the candidate molecules indicates that the molecules modulate the activity of CDK2 or said protein or said complex of CDK2 and said protein. In preferred embodiments, the modulators are identified by administering the candidate molecules to a transgenic non-human animal expressing both CDK2 and a CDK2-IP from promoters that are not the native CDK2 or the native CDK2-IP promoters, more preferably where the candidate molecules are also recombinantly expressed in the transgenic non-human animal. Alternatively, the method for identifying such modulators can be carried out in vitro, preferably with purified CDK2, purified CDK2-IP, and purified candidate molecules.

Methods that can be used to carry out the foregoing are commonly known in the art. Agents to be screened can be provided as mixtures of a limited number of specified compounds, or as compound libraries, peptide libraries and the like. Agents to be screened may also include all forms of antisera, antisense nucleic acids, etc. that can modulate CDK2:CDK2-IP complex activity, or hsReq*-1 and hsReq*-2 activity.

By way of example, diversity libraries, such as random or combinatorial peptide or non-peptide libraries can be screened for molecules that specifically bind to a CDK2:CDK2-IP complex or hsReq*-1 and hsReq*-2 protein. Many libraries are known in the art that can be used, e.g., chemically synthesized libraries, recombinant (e.g., phage display libraries), and in vitro translation-based libraries.

Examples of chemically synthesized libraries are described in Fodor et al., 1991, Science 251:767–773; Houghten et al., 1991, Nature 354:84–86; Lam et al., 1991, Nature 354:82–84; Medynski, 1994, BioTechnology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott and Smith 1990, Science 249:386–390; Devlin et al., 1990, Science, 249:404–406; Christian, R. B., et al., 1992, J. Mol. Biol. 227:711–718; Lenstra, 1992, J. Immunol. Meth. 152:149–157; Kay et al., 1993, Gene 128:59–65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Natl. Acad. Sci. USA 91:9022–9026.

By way of examples of non-peptide libraries, a benzodiazepine library (see e.g., Bunin et al., 1994, Proc. Natl. Acad. Sci. USA 91:4708–4712) can be adapted for use.

Peptoid libraries (Simon et al., 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

Screening the libraries can be accomplished by any of a variety of commonly known methods. See, e.g., the following references, which disclose screening of peptide libraries: Parmley and Smith, 1989, Adv. Exp. Med. Biol. 251:215–218; Scott and Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. Nos. 5,096,815, 5,223,409, and 5,198,346, all to Ladner et al.; Rebar and Pabo, 1993, Science 263:671–673; and PCT Publication No. WO 94/18318.

In a specific embodiment, screening can be carried out by contacting the library members with a CDK2:CDK2-IP complex or an hsReq*-1 or hsReq*-2 protein (or nucleic acid or derivative) immobilized on a solid phase and harvesting those library members that bind to the protein (or nucleic acid or derivative). Examples of such screening methods, termed "panning" techniques are described by way of example in Parmley and Smith, 1988, Gene 73:305–318; Fowlkes et al., 1992, BioTechniques 13:422–427; PCT Publication No. WO 94/18318; and in references cited hereinabove.

In a specific embodiment, fragments and/or analogs of CDK2 or a CDK2-IP, especially peptidomimetics, are screened for activity as competitive or non-competitive inhibitors of CDK2:CDK2-IP complex formation, and thereby inhibit CDK2-IP complex activity.

In a preferred embodiment, molecules that bind to CDK2:CDK2-IP complexes or hsReq*-1 or hsReq*-2 proteins can be screened for using the yeast two hybrid system described in Section 5.7.1 infra and exemplified in Section 6.1 infra.

In one embodiment, agents that modulate (i.e. inhibit, antagonize, or agonize) CDK2:CDK2-IP complex activity can be screened using a binding inhibition assay, wherein agents are screened for their ability to inhibit formation of a CDK2:CDK2-IP complex under aqueous, or physiological, binding conditions in which CDK2:CDK2-IP complex formation occurs in the absence of the agent to be tested. Agents that interfere with the formation of CDK2:CDK2-IP complexes are identified as antagonists of complex formation.

Methods for screening may involve labeling the complex proteins with radioligands (e.g., $^{125}$I or $^{3}$H), magnetic ligands (e.g., paramagnetic beads covalently attached to photobiotin acetate), and fluorescent ligands (e.g., fluorescein or rhodamine) or enzyme ligands (e.g., luciferase or beta-galactosidase). The reactants that bind in solution can then be isolated by one of many techniques known in the art, including but not restricted to, co-immunoprecipitation of the labeled moiety using antisera against the unlabeled binding partner (or labeled binding partner with a distinguishable marker from that used on the labeled moiety) protein, immunoaffinity chromatography, size exclusion chromatography, and gradient density centrifugation. In a preferred embodiment, one binding partner is a small fragment or peptidomimetic that is not retained by a commercially available filter. Upon binding, the labeled species is then unable to pass through the filter, providing for a simple assay of complex formation.

Methods commonly known in the art are used to label at least one of the members of the CDK2:CDK2-IP complex. Suitable labeling includes, but is not limited to, radiolabeling by incorporation of radiolabeled amino acids, e.g. $^{3}$H-leucine of $^{35}$S-methionine, radiolabeling by post-translational iodination with $^{125}$I or $^{131}$I using the chloramine T method, Bolton-Hunter reagents, etc., or labeling with $^{32}$P using phosphorylase and inorganic radiolabeled phosphorous, biotin labeling with photobiotin-acetate and sunlamp exposure, etc. In cases where one of the members of the CDK2:CDK2-IP complex is immobilized, e.g. as described infra, the free species is labeled. Where neither of the interacting species is immobilized, each can be labeled with a distinguishable marker such that isolation of both moieties can be followed to provide for more accurate quantitation, and to distinguish the formation of homomeric from heteromeric complexes. Methods that utilize accessory proteins that bind to one of the modified interactants to improve the sensitivity of detection, increase the stability of the complex, etc. are provided.

Typical binding conditions are, for example, but not by way of limitation, in an aqueous salt solution of 10–250 mM NaCl, 5–50 mM Tris-HCl, pH 5–8, 0.5% Triton X-100 or other detergent that improves specificity of interaction. Metal chelators and/or divalent cations may be added to improve binding and/or reduce proteolysis. Reaction temperatures may include 4, 10, 15, 22, 25, 35, or 42 degrees Celsius, and time of incubation is typically at least 15 seconds, but longer times are preferred to allow binding equilibrium to occur. Particular CDK2:CDK2-IP complexes can be assayed using routine protein binding assays to determine optimal binding conditions for reproducible binding.

The physical parameters of complex formation can be analyzed by quantitation of complex formation using assay methods specific for the label used, e.g. liquid scintillation counting for radioactivity detection, enzyme activity measurements for enzyme label, etc. The reaction results are then analyzed utilizing Scatchard analysis, Hill analysis, and other methods commonly known in the arts (see, e.g., Proteins, Structures, and Molecular Principles, (1984) Creighton, ed., W.H. Freeman and Company, New York).

In a second common approach to binding assays, one of the binding species is immobilized on a filter, in a microtiter plate well, in a test tube, to a chromatography matrix, etc., either covalently or non-covalently. Proteins can be covalently immobilized using any method well known in the art, for example, but not limited to the method of Kadonaga and Tjian (1986, Proc. Natl. Acad. Sci. USA 83: 5889–5893, 1986), i.e., linkage to a cyanogen-bromide derivatized substrate such as CNBr-Sepahrose 4B. Where needed, the use of spacers can reduce steric hindrance from the substrate. Non-covalent attachment of proteins to a substrate include, but are not limited to, attachment of a protein to a charged surface, binding with specific antibodies, binding to a third unrelated IP, etc.

In one embodiment, immobilized CDK2 is used to assay for binding with a radioactively-labeled CDK2-IP in the presence and absence of a compound to be tested for its ability to modulate CDK2:CDK2-IP complex formation. The binding partners are allowed to bind under aqueous, or physiological, conditions (e.g. the conditions under which the original interaction was detected). Conversely, in another embodiment, the CDK2-IP is immobilized and contacted with the labeled CDK2 protein or derivative thereof under binding conditions.

Assays of agents (including cell extracts or library pool) for competition for binding of one member of a CDK2:CDK2-IP complex (or derivatives thereof) with the other member of the CDK2:CDK2-IP complex labeled by any means, e.g. those means described supra), are provided to screen for competitors of CDK2:CDK2-IP complex formation.

In specific embodiments, blocking agents to inhibit non-specific binding of reagents to other protein components, or absorptive losses of reagents to plastics, immobilization matrices, etc., are included in the assay mixture. Blocking agents include, but are not restricted to bovine serum albumin, beta-casein, nonfat dried milk, Denhardt's reagent, Ficoll, polyvinylpyrolidine, nonionic detergents (e.g., NP40, Triton X-100, Tween 20, Tween 80, etc.), ionic detergents (e.g. SDS, LDS, etc.), polyethyleneglycol, etc. Appropriate blocking agent concentrations allow CDK2:CDK2-IP complex formation.

After binding is performed, unbound, labeled protein is removed in the supernatant, and the immobilized protein with any bound, labeled protein is washed extensively. The amount of label bound is then quantitated using standard methods in the art to detect the label as described supra.

5.7.1. Assays for Protein-Protein Interactions

One aspect of the present invention provides methods for assaying and screening fragments, derivatives and analogs of derivatives, analogs and fragments of CDK2-interacting proteins (for binding to CDK2 peptides). Derivatives, analogs and fragments of CDK2-IPs that interact with CDK2 can be identified by means of a yeast two hybrid assay system (Fields and Song, 1989, Nature 340: 245–246; U.S. Pat. No. 5,283,173 by Fields and Song) or, more preferably, an improvement thereof as described in U.S. patent application Ser. No. 08/663,824, filed Jun. 14, 1996, and Ser. No. 08/874,825, filed Jun. 13, 1997, both entitled "Identification and Comparison of Protein—Protein Interactions that Occur in Populations and Identification of Inhibitors of These Interactions", and both by Nandabalan et al., which are incorporated by reference herein in their entireties. Because the interactions are screened for in yeast, the intermolecular protein interactions detected in this system generally occur under physiological conditions that mimic the conditions in mammalian cells (Chien et al., 1991, Proc. Natl. Acad. Sci. USA 88: 9578–9581.)

Identification of interacting proteins by the improved yeast two hybrid system is based upon the detection of the expression of a reporter gene ("Reporter Gene"), the transcription of which is dependent upon the reconstitution of a transcriptional regulator by the interaction of two proteins, each fused to one half of the transcriptional regulator. The bait (CDK2 or derivative or analog) and prey (proteins to be tested for ability to interact with the bait) proteins are expressed as fusion proteins to a DNA binding domain, and to a transcriptional regulatory domain, respectively, or vice versa. In various specific embodiments, the prey has a complexity of at least 50, 100, 500, 1,000, 5,000, 10,000, or 50,000; or has a complexity in the range of 25 to 100,000, 100 to 100,000, 50,000 to 100,000, or 100,000 to 500,000. For example, the prey population can be one or more nucleic acids encoding mutants of a CDK2-IP (e.g., as generated by site-directed mutagenesis or another method of making mutations in a nucleotide sequence). Preferably, the prey populations are proteins encoded by DNA, e.g., cDNA or genomic DNA or synthetically generated DNA. For example, the populations can be expressed from chimeric genes comprising cDNA sequences from an un-characterized sample of a population of cDNA from mammalian RNA. Preferably, the prey population are proteins encoded by DNA, e.g., cDNA or genomic DNA or synthetically generated DNA.

In a specific embodiment, recombinant biological libraries expressing random peptides can be used as the source of prey nucleic acids.

In another embodiment, the invention provides methods for screening for inhibitors of the interacting proteins identified herein. Briefly, the protein-protein interaction assay can be carried out as described herein, except that it is done in the presence of one or more candidate molecules. An increase or decrease in Reporter Gene activity relative to that present when the one or more candidate molecules are absent indicates that the candidate molecule has an effect on the interacting pair. In a preferred method, inhibition of the interaction is selected for (i.e. inhibition of the interaction is necessary for the cells to survive), for example, where the interaction activates the URA3 gene, causing yeast to die in medium containing the chemical 5-fluoroorotic acid (Rothstein, 1983, Meth. Enzymol. 101:167–180). The identification of inhibitors of such interactions can also be accomplished, for example, but not by way of limitation, using competitive inhibitor assays, as described supra.

In general, proteins of the bait and prey populations are provided as fusion (chimeric) proteins (preferably by recombinant expression of a chimeric coding sequence) containing each protein contiguous to a pre-selected sequence. For one population, the pre-selected sequence is a DNA binding domain. The DNA binding domain can be any DNA binding domain, as long as it specifically recognizes a DNA sequence within a promoter. For example, the DNA binding domain is of a transcriptional activator or inhibitor. For the other population, the pre-selected sequence is an activator or inhibitor domain of a transcriptional activator or inhibitor, respectively. The regulatory domain alone (not as a fusion to a protein sequence) and the DNA-binding domain alone (not as a fusion to a protein sequence) preferably do not detectably interact (so as to avoid false positives in the assay). The assay system further includes a reporter gene operably linked to a promoter that contains a binding site for the DNA binding domain of the transcriptional activator (or inhibitor). Accordingly, in the method of the invention, binding of a CDK2 fusion protein to a prey fusion protein leads to reconstitution of a transcriptional activator (or inhibitor) which activates (or inhibits) expression of the Reporter Gene. The activation of transcription of the Reporter Gene occurs intracellularly, e.g., in prokaryotic or eukaryotic cells, preferably in cell culture.

The promoter that is operably linked to the reporter gene nucleotide sequence can be a native or non-native promoter of the nucleotide sequence, and the DNA binding site(s) that are recognized by the DNA binding domain portion of the fusion protein can be native to the promoter (if the promoter normally contains such binding site(s)) or non-native. Thus, for example, one or more tandem copies (e.g., 4 or 5 copies) of the appropriate DNA binding site can be introduced upstream of the TATA box in the desired promoter (e.g., in the area of position −100 to −400). In a preferred aspect, 4 or 5 tandem copies of the 17 bp UAS (GAL4 DNA binding site) are introduced upstream of the TATA box in the desired promoter, which is upstream of the desired coding sequence for a selectable or detectable marker. In a preferred embodiment, the GAL1-10 promoter is operably fused to the desired nucleotide sequence; the GAL1-10 promoter already contains 5 binding sites for GAL4. Alternatively, the transcriptional activation binding site of the desired gene(s) can be deleted and replaced with GAL4 binding sites (Bartel et al., 1993, BioTechniques 14(6):920–924; Chasman et al., 1989, Mol. Cell. Biol. 9:4746–4749). The Reporter Gene preferably contains the sequence encoding a detectable or selectable marker the expression of which is regulated by the transcriptional activator, such that the marker is either turned on or off in the cell in response to the presence of a specific interaction. Preferably, the assay is carried out in the absence of background levels of the transcriptional activator (e.g., in a cell that is mutant or otherwise lacking in the transcriptional activator). In one embodiment, more than one Reporter Gene is used to detect transcriptional activation, e.g., one Reporter Gene encoding a detectable marker and one or more Reporter Genes encoding different selectable markers. The detectable marker can be any molecule that can give rise to a detectable signal, e.g., a fluorescent protein or a protein that can be readily visualized or that is recognizable by a specific antibody. The selectable marker can be any protein molecule that confers ability to grow under conditions that do not support the growth of cells not expressing the selectable marker, e.g., the selectable marker is an enzyme that provides an essential nutrient and the cell in which the interaction assay occurs is deficient in the enzyme and the selection medium lacks such nutrient. The Reporter Gene can either be under the control of the native promoter that naturally contains a binding site for the DNA binding protein, or under the control of a heterologous or synthetic promoter.

The activation domain and DNA binding domain used in the assay can be from a wide variety of transcriptional activator proteins, as long as these transcriptional activators have separable binding and transcriptional activation domains. For example, the GAL4 protein of S. cerevisiae, the GCN4 protein of S. cerevisiae (Hope and Struhl, 1986, Cell 46:885–894), the ARD1 protein of S. cerevisiae (Thukral et al., 1989, Mol. Cell. Biol. 9:2360–2369), and the human estrogen receptor (Kumar et al., 1987, Cell 51:941–951) have separable DNA binding and activation domains. The DNA binding domain and activation domain that are employed in the fusion proteins need not be from the same transcriptional activator. In a specific embodiment, a GAL4 or LEXA DNA binding domain is employed. In another specific embodiment, a GAL4 or herpes simplex virus VP16 (Triezenberg et al., 1988, Genes Dev. 2:730–742) activation domain is employed. In a specific embodiment, amino acids 1–147 of GAL4 (Ma et al., 1987, Cell 48:847–853; Ptashne et al., 1990, Nature 346:329–331) is the DNA binding domain, and amino acids 411–455 of VP16 (Triezenberg et al., 1988, Genes Dev. 2:730–742; Cress et al., 1991, Science 251:87–90) is the activation domain.

In a preferred embodiment, the yeast transcription factor GAL4 is reconstituted by the protein-protein interaction and the host strain is mutant for GAL4. In another embodiment, the DNA-binding domain is Ace1N and/or the activation domain is Ace1, the DNA binding and activation domains of the Ace1 protein, respectively. Ace1 is a yeast protein that activates transcription from the CUP1 operon in the presence of divalent copper. CUP1 encodes metallothionein, which chelates copper, and the expression of CUP1 protein allows growth in the presence of copper, which is otherwise toxic to the host cells. The Reporter Gene can also be a CUP1-lacZ fusion that expresses the enzyme β-galactosidase (detectable by routine chromogenic assay) upon binding of a reconstituted Ace1N transcriptional activator (see Chaudhuri et al., 1995, FEBS Letters 357:221–226). In another specific embodiment, the DNA binding domain of the human estrogen receptor is used, with a Reporter Gene driven by one or three estrogen receptor response elements (Le Douarin et al., 1995, Nucl. Acids. Res. 23:876–878).

The DNA binding domain and the transcription activator/inhibitor domain each preferably has a nuclear localization signal (see Ylikomi et al., 1992, EMBO J. 11:3681–3694; Dingwall and Laskey, 1991, TIBS 16:479–481) functional in the cell in which the fusion proteins are to be expressed.

To facilitate isolation of the encoded proteins, the fusion constructs can further contain sequences encoding affinity tags such as glutathione-S-transferase or maltose-binding protein or an epitope of an available antibody, for affinity purification (e.g., binding to glutathione, maltose, or a particular antibody specific for the epitope, respectively) (Allen et al., 1995, TIBS 20:511–516). In another embodiment, the fusion constructs further comprise bacterial promoter sequences for recombinant production of the fusion protein in bacterial cells (see Allen et al., 1995, TIBS 20:511–516).

The host cell in which the interaction assay occurs can be any cell, prokaryotic or eukaryotic, in which transcription of the Reporter Gene can occur and be detected, including but not limited to mammalian (e.g., monkey, chicken, mouse, rat, human, bovine), bacteria, and insect cells, and is preferably a yeast cell. Expression constructs encoding and capable of expressing the binding domain fusion proteins, the transcriptional activation domain fusion proteins, and the Reporter Gene product(s) are provided within the host cell, by mating of cells containing the expression constructs, or by cell fusion, transformation, electroporation, microinjection, etc. In a specific embodiment in which the assay is carried out in mammalian cells (e.g., hamster cells), the DNA binding domain is the GAL4 DNA binding domain, the activation domain is the herpes simplex virus VP16 transcriptional activation domain, and the Reporter Gene contains the desired coding sequence operably linked to a minimal promoter element from the adenovirus E1B gene driven by several GAL4 DNA binding sites (see Fearon et al., 1992, Proc. Natl. Acad. Sci. USA 89:7958–7962). The host cell used should not express an endogenous transcription factor that binds to the same DNA site as that recognized by the DNA binding domain fusion population. Also, preferably, the host cell is mutant or otherwise lacking in an endogenous, functional form of the Reporter Gene(s) used in the assay.

Various vectors and host strains for expression of the two fusion protein populations in yeast are known and can be used (see, e.g., Fields et al., U.S. Pat. No. 5,1468,614 dated Nov. 21, 1995; Bartel et al., 1993, "Using the two-hybrid system to detect protein-protein interactions," in Cellular Interactions in Development, Hartley, D. A. (ed.), Practical Approach Series xviii, IRL Press at Oxford University Press, New York, N.Y., pp. 153–179; Fields and Sternglanz, 1994, TIG 10:286–292). By way of example but not limitation, yeast strains or derivative strains made therefrom, which can be used are N105, N106, N1051, N1061, and YULH, as described in Section 6.3, infra. Exemplary strains that can be used in the assay of the invention also include, but are not limited to, the following:

Y190: MATa, ura3-52, his3-200, lys2-801, ade2-101, trp1-901, leu2-3,112, gal4Δ, gal80Δ, cyh$^r$2, LYS2::GAL1$_{UAS}$-HIS3$_{TATA}$HIS3, URA3::GAL1$_{UAS}$-GAL1$_{TATA}$-lacZ (available from Clontech, Palo Alto, Calif.; Harper et al., 1993, Cell 75:805–816). Y190 contains HIS3 and lacZ Reporter Genes driven by GAL4 binding sites.

CG-1945: MATa, ura3-52, his3-200, lys2-801, ade2-101, trp1-901, leu2-3,112, gal4-542, gal80-538, cyh'2, LYS2::GAL1$_{UAS}$-HIS3$_{TATA}$HIS3, URA3::GAL1$_{UAS17mers(x3)}$-CYC1$_{TATA}$-lacZ (available from Clontech). CG-1945 contains HIS3 and lacZ Reporter Genes driven by GAL4 binding sites.

Y187: MAT-α, ura3-52, his3-200, ade2-101, trp1-901, leu2-3,112, gal4Δ, gal80Δ, URA3:: GAL1$_{UAS}$-GAL1$_{TATA}$-lacZ (available from Clontech). Y187 contains a lacZ Reporter Gene driven by GAL4 binding sites.

SFY526: MATa, ura3-52, his3-200, lys2-801, ade2-101, trp1-901, leu2-3,112, gal4-542, gal80-538, can$^r$, URA3:: GAL1-lacZ (available from Clontech). SFY526 contains HIS3 and lacZ Reporter Genes driven by GAL4 binding sites.

HF7c: MATa, ura3-52, his3-200, lys2-801, ade2-101, trp1-901, leu2-3,112, gal4-542, gal80-538, LYS2::GAL1-HIS3. URA3::GAL1$_{UAS17MERS(x3)}$-CYC1-lacZ (available from Clontech). HF7c contains HIS3 and lacZ Reporter Genes driven by GAL4 binding sites.

YRG-2: MATa, ura3-52, his3-200, lys2-801, ade2-101, trp1-901, leu2-3,112, gal4-542, gal80-538 LYS2::GAL1$_{UAS}$-GAL1$_{TATA}$-HIS3, URA3::GAL1$_{UAS17mers(x3)}$-CYC1-lacZ (available from Stratagene). YRG-2 contains HIS3 and lacz Reporter Genes driven by GAL4 binding sites.

Many other strains commonly known and available in the art can be used.

If not already lacking in endogenous Reporter Gene activity, cells mutant in the Reporter Gene may be selected by known methods, or the cells can be made mutant in the target Reporter Gene by known gene-disruption methods prior to introducing the Reporter Gene (Rothstein, 1983, Meth. Enzymol. 101:202–211).

In a specific embodiment, plasmids encoding the different fusion protein populations can be both introduced into a single host cell (e.g., a haploid yeast cell) containing one or more Reporter Genes, by co-transformation, to conduct the assay for protein-protein interactions. Or, preferably, the two fusion protein populations are introduced into a single cell either by mating (e.g. for yeast cells) or cell fusions (e.g., of mammalian cells). In a mating type assay, conjugation of haploid yeast cells of opposite mating type that have been transformed with a binding domain fusion expression construct (preferably a plasmid) and an activation (or inhibitor) domain fusion expression construct (preferably a plasmid), respectively, delivers both constructs into the same diploid cell. The mating type of a yeast strain may be manipulated by transformation with the HO gene (Herskowitz and Jensen, 1991, Meth. Enzymol. 194:132–146).

In a preferred embodiment, a yeast interaction mating assay is employed, using two different types of host cells, strain-types a and alpha, of the yeast *Saccharomyces cerevisiae*. The host cell preferably contains at least two Reporter Genes, each with one or more binding sites for the DNA-binding domain (e.g., of a transcriptional activator). The activator domain and DNA binding domain are each parts of chimeric proteins formed from the two respective populations of proteins. One set of host cells, for example the a strain cells, contains fusions of the library of nucleotide sequences with the DNA-binding domain of a transcriptional activator, such as GAL4. The hybrid proteins expressed in this set of host cells are capable of recognizing the DNA-binding site on the Reporter Gene. The second set of yeast host cells, for example alpha strain cells, contains nucleotide sequences encoding fusions of a library of DNA sequences fused to the activation domain of a transcriptional activator. In a preferred embodiment, the fusion protein constructs are introduced into the host cell as a set of plasmids. These plasmids are preferably capable of autonomous replication in a host yeast cell and preferably can also be propagated in *E. coli*. The plasmid contains a promoter directing the transcription of the DNA binding or activation domain fusion genes, and a transcriptional termination signal. The plasmid also preferably contains a selectable marker gene, permitting selection of cells containing the plasmid. The plasmid can be single-copy or multi-copy. Single-copy yeast plasmids that have the yeast centromere may also be used to express the activation and DNA binding domain fusions (Elledge et al., 1988, Gene 70:303–312). In another embodiment, the fusion constructs are introduced directly into the yeast chromosome via homologous recombination. The homologous recombination for these purposes is mediated through yeast sequences that are not essential for vegetative growth of yeast, e.g., MER2, MER1, ZIP1, REC102, or ME14 gene.

Bacteriophage vectors can also be used to express the DNA binding domain and/or activation domain fusion proteins. Libraries can generally be prepared faster and more easily from bacteriophage vectors than from plasmid vectors.

In a specific embodiment, the invention provides a method of detecting one or more protein-protein interactions comprising (a) recombinantly expressing CDK2 or a derivative or analog thereof in a first population of yeast cells being of a first mating type and comprising a first fusion protein containing the CDK2 sequence and a DNA binding domain, wherein said first population of yeast cells contains a first nucleotide sequence operably linked to a promoter driven by one or more DNA binding sites recognized by said DNA binding domain such that an interaction of said first fusion protein with a second fusion protein, said second fusion protein comprising a transcriptional activation domain, results in increased transcription of said first nucleotide sequence; (b) negatively selecting to eliminate those yeast cells in said first population in which said increased transcription of said first nucleotide sequence occurs in the absence of said second fusion protein; (c) recombinantly expressing in a second population of yeast cells of a second mating type different from said first mating type, a plurality of said second fusion proteins, each second fusion protein comprising a sequence of a fragment, derivative or analog of a CDK2-IP and an activation domain of a transcriptional activator, in which the activation domain is the same in each said second fusion protein; (d) mating said first population of yeast cells with said second population of yeast cells to form a third population of diploid yeast cells, wherein said third population of diploid yeast cells contains a second nucleotide sequence operably linked to a promoter driven by a DNA binding site recognized by said DNA binding domain such that an interaction of a first fusion protein with a second fusion protein results in increased transcription of said second nucleotide sequence, in which the first and second nucleotide sequences can be the same or different; and (e) detecting said increased transcription of said first and/or second nucleotide sequence, thereby detecting an interaction between a first fusion protein and a second fusion protein.

In a preferred embodiment, the bait CDK2 sequence and the prey library of chimeric genes are combined by mating the two yeast strains on solid media for a period of approximately 6–8 hours. In a less preferred embodiment, the mating is performed in liquid media. The resulting diploids contain both kinds of chimeric genes, i.e., the DNA-binding domain fusion and the activation domain fusion.

Preferred reporter genes include URA3, HIS3 and/or the lacZ genes (see, e.g., Rose and Botstein, 1983, Meth. Enzymol. 101:167–180) operably linked to GAL4 DNA-binding domain recognition elements. Other reporter genes comprise the functional coding sequences for, but not limited to, Green Fluorescent Protein (GFP) (Cubitt et al., 1995, Trends Biochem. Sci. 20:448–455), luciferase, LEU2, LYS2, ADE2, TRP1, CAN1, CYH2, GUS, CUP1 or chloramphenicol acetyl transferase (CAT). Expression of LEU2, LYS2, ADE2 and TRP1 are detected by growth in a specific defined media; GUS and CAT can be monitored by well known enzyme assays; and CAN1 and CYH2 are detected by selection in the presence of canavanine and cycloheximide. With respect to GFP, the natural fluorescence of the protein is detected.

In a specific embodiment, transcription of the Reporter Gene is detected by a linked replication assay. For example, as described by Vasavada et al. (1991, Proc. Natl. Acad. Sci. USA 88:10686–10690), expression of SV40 large T antigen is under the control of the E1B promoter responsive to GAL4 binding sites. The replication of a plasmid containing the SV40 origin of replication, indicates the reconstitution of the GAL4 protein and a protein-protein interaction. Alternatively, a polyoma virus replicon can be employed (Vasavada et al., 1991, Proc. Natl. Acad. Sci. USA 88:10686–10690).

In another embodiment, the expression of Reporter Genes that encode proteins can be detected by immunoassay, i.e., by detecting the immunospecific binding of an antibody to such protein, which antibody can be labeled, or alternatively, which antibody can be incubated with a labeled binding partner to the antibody, so as to yield a detectable signal. Alam and Cook (1990, Anal. Biochem. 188:245–254) disclose non-limiting examples of detectable marker genes that can be operably linked to a transcriptional regulatory region responsive to a reconstituted transcriptional activator, and thus used as Reporter Genes.

The activation of Reporter Genes like URA3 or HIS3 enables the cells to grow in the absence of uracil or histidine, respectively, and hence serves as a selectable marker. Thus, after mating, the cells exhibiting protein-protein interactions are selected by the ability to grow in media lacking a nutritional component, such as uracil or histidine, respectively (referred to as –URA (minus URA) and –HIS (minus HIS) medium, respectively). The –HIS medium preferably contains 3-amino-1,2,4-triazole (3-AT), which is a competitive inhibitor of the HIS3 gene product and thus requires higher levels of transcription in the selection (see Durfee et al., 1993, Genes Dev. 7:555–569). Similarly, 6-azauracil, which is an inhibitor of the URA3 gene product, can be included in –URA medium (Le Douarin et al., 1995, Nucl. Acids Res. 23:876–878). URA3 gene activity can also be detected and/or measured by determining the activity of its gene product, orotidine-51-monophosphate decarboxylase (Pierrat et al., 1992, Gene 119:237–245; Wolcott et al., 1966, Biochem. Biophys. Acta 122:532–534). In other embodiments of the invention, the activities of the reporter genes like lacZ or GFP are monitored by measuring a detectable signal (e.g., fluorescent or chromogenic) that results from the activation of these Reporter Genes. For example, lacZ transcription can be monitored by incubation in the presence of a chromogenic substrate, such as X-gal (5-bromo-4-chloro-3-indolyl-α-D-galactoside), for its encoded enzyme, β-galactosidase. The pool of all interacting proteins isolated by this manner from mating the CDK2 sequence product and the library identifies the "CDK2 interactive population".

In a preferred embodiment of the invention, false positives arising from transcriptional activation by the DNA binding domain fusion proteins in the absence of a transcriptional activator domain fusion protein are prevented or reduced by negative selection for such activation within a host cell containing the DNA binding fusion population, prior to exposure to the activation domain fusion population. By way of example, if such cell contains URA3 as a Reporter Gene, negative selection is carried out by incubating the cell in the presence of 5-fluoroorotic acid (5-FOA, which kills URA+ cells (Rothstein, 1983, Meth. Enzymol. 101:167–180). Hence, if the DNA-binding domain fusions by themselves activate transcription, the metabolism of 5-FOA will lead to cell death and the removal of self-activating DNA-binding domain hybrids.

Negative selection involving the use of a selectable marker as a Reporter Gene and the presence in the cell medium of an agent toxic or growth inhibitory to the host cells in the absence of Reporter Gene transcription is preferred, since it allows a higher rate of processing than other methods. As will be apparent, negative selection can also be carried out on the activation domain fusion population prior to interaction with the DNA binding domain fusion population, by similar methods, either alone or in addition to negative selection of the DNA binding fusion population.

Negative selection can also be carried out on the recovered CDK2:CDK2-IP pairs by known methods (see, e.g., Bartel et al., 1993, BioTechniques 14:920–924) although pre-negative selection (prior to the interaction assay), as described above, is preferred. For example, each plasmid encoding a protein (peptide or polypeptide) fused to the activation domain (one-half of a detected interacting pair) can be transformed back into the original screening strain, either alone or with a plasmid encoding only the DNA-binding domain, the DNA-binding domain fused to the detected interacting protein, or the DNA-binding domain fused to a protein that does not affect transcription or participate in the protein-protein interaction; a positive interaction detected with any plasmid other than that encoding the DNA-binding domain fusion to the detected interacting protein is deemed a false positive and eliminated from the screen.

In a preferred embodiment, the CDK2 plasmid population is transformed in a yeast strain of a first mating type (a or alpha), and the second plasmid population (containing the library of DNA sequences) is transformed in a yeast strain of different mating type. Both strains are preferably mutant for URA3 and HIS3, and contain HIS3, and optionally lacZ, as a Reporter Genes. The first set of yeast cells are positively selected for the CDK2 plasmids and are negatively selected for false positives by incubation in medium lacking the selectable marker (e.g., tryptophan) and containing 5-FOA. Yeast cells of the second mating type are transformed with the second plasmid population, and are positively selected for the presence of the plasmids containing the library of fusion proteins. Selected cells are pooled. Both groups of pooled cells are mixed together and mating is allowed to occur on a solid phase. The resulting diploid cells are then transferred to selective media that selects for the presence of each plasmid and for activation of Reporter Genes.

In a preferred embodiment of the invention, after an interactive population is obtained, the DNA sequences encoding the pairs of interactive proteins are isolated by a method wherein either the DNA-binding domain hybrids or the activation domain hybrids are amplified, in separate respective reactions. Preferably, the amplification is carried out by polymerase chain reaction (PCR) (U.S. Pat. Nos. 4,683,202, 4,683,195 and 4,889,818; Gyllenstein et al., 1988, Proc. Natl. Acad. Sci. USA 85:7652–7656; Ochman et al., 1988, Genetics 120:621–623; Loh et al., 1989, Science 243:217–220; Innis et al., 1990, PCR Protocols, Academic Press, Inc., San Diego, Calif.), using pairs of oligonucleotide primers specific for either the DNA-binding domain hybrids or the activation domain hybrids. This PCR reaction can also be performed on pooled cells expressing interacting protein pairs, preferably pooled arrays of interactants. Other amplification methods known in the art can be used, including but not limited to ligase chain reaction (see EP 320,308) use of $Q^\beta$ replicase, or methods listed in Kricka et al., 1995, Molecular Probing, Blotting, and Sequencing, Chap. 1 and Table IX, Academic Press, New York.

The plasmids encoding the DNA-binding domain hybrid and the activation domain hybrid proteins can also be isolated and cloned by any of the methods well known in the art. For example, but not by way of limitation, if a shuttle (yeast to E. coli) vector is used to express the fusion proteins, the genes can be recovered by transforming the yeast DNA into E. coli and recovering the plasmids from E. coli (see, e.g., Hoffman et al., 1987, Gene 57:267–272). Alternatively, the yeast vector can be isolated, and the insert encoding the fusion protein subcloned into a bacterial expression vector, for growth of the plasmid in E. coli.

5.8 Pharmaceutical Compositions

The invention provides methods of treatment (and prophylaxis) by administration to a subject of an effective amount of a Therapeutic of the invention. In a preferred aspect, the Therapeutic is substantially purified. The subject is preferably an animal, including but not limited to animals such as cows, pigs, horses, chickens, cats, dogs, etc., and is preferably a mammal, and most preferably human. In a specific embodiment, a non-human mammal is the subject.

Formulations and methods of administration that can be employed when the Therapeutic comprises a nucleic acid are described in Sections 5.5.6 and 5.5.7 above; additional appropriate formulations and routes of administration can be selected from among those described hereinbelow.

Various delivery systems are known and can be used to administer a Therapeutic of the invention, e.g., encapsulation in liposomes, microparticles, microcapsules, recombinant cells capable of expressing the Therapeutic, receptor-mediated endocytosis (see, e.g., Wu and Wu, 1987, J. Biol. Chem. 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the Therapeutic can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the Therapeutic can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the Therapeutic is a nucleic acid encoding a protein Therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid Therapeutic can be introduced intracellularly and incorporated within host cell DNA for expression, by homologous recombination.

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.9 Animals Models

The invention also provides animal models. In one embodiment, animal models for diseases and disorders involving CDK2:CDK2-IP complexes are provided. These diseases and disorders include but are not limited to: cell proliferative disorders including tumorigenesis and tumor spread, degenerative disorders including neurodegenerative disorders, and vascular disorders including atherosclerosis-associated diseases and disorders. Such animals can be initially produced by promoting homologous recombination or insertional mutagenesis between CDK2 and CDK2-IP genes in the chromosome and exogenous CDK2 and CDK2-IP genes that have been rendered biologically inactive (preferably by insertion of a heterologous sequence, e.g., an antibiotic resistance gene) or deleted. In a preferred aspect, homologous recombination is carried out by transforming embryo-derived stem (ES) cells with a vector containing the insertionally inactivated CDK2 and CDK2-IP genes, such that homologous recombination occurs, followed by injecting the ES cells into a blastocyst, and implanting the blastocyst into a foster mother, followed by the birth of the chimeric animal ("knockout animal") in which a CDK2 gene and a CDK2-IP gene have been inactivated or deleted (see Capecchi, 1989, Science 244:1288–1292). The chimeric animal can be bred to produce additional knockout animals. Such animals can be mice, hamsters, sheep, pigs, cattle, etc., and are preferably non-human mammals. In a specific embodiment, a knockout mouse is produced.

Such knockout animals are expected to develop or be predisposed to developing diseases or disorders involving, but not restricted to, cell proliferative disorders including cancer and benign hypertrophy, various disorders involving cellular apoptosis and cellular differentiation, autoimmune diseases, etc., and thus can have use as animal models of such diseases and disorders, e.g., to screen for or test molecules (e.g., potential Therapeutics) for the ability to inhibit cell proliferative, autoimmune, and other diseases.

In a different embodiment of the invention, transgenic animals that have incorporated and express (or overexpress or mis-express) a functional CDK2 and/or CDK2-IP gene, e.g. by introducing the CDK2 and CDK2-IP genes under the control of a heterologous promoter (i.e., a promoter that is not the native CDK2 or CDK2-IP promoter) that either overexpresses the protein or proteins or expresses them in tissues not normally expressing the complexes or proteins can have use as animal models of diseases and disorders characterized by elevated levels of CDK2:CDK2-IP complexes. Such animals can be used to screen for or test molecules for the ability to treat or prevent the diseases and disorders cited supra.

In one embodiment, the invention provides a recombinant non-human animal in which both an endogenous CDK2 gene and an endogenous CDK2-IP gene selected from the group consisting of cyclin H, cyclin I, ERH, hsReq*-1, and hsReq*-2 have been deleted or inactivated by homologous recombination or insertional mutagenesis of said animal or an ancestor thereof. In another embodiment, the invention provides a recombinant non-human animal containing both a CDK2 gene and a CDK2-IP gene selected from the group consisting of cyclin H, cyclin I, ERH, hsReq*-1, and hsReq*-2 in which the CDK2 gene is under the control of a promoter that is not the native CDK2 gene promoter and the CDK2-IP gene is under the control of a promoter that is not the native CDK2-IP gene promoter. In a specific embodiment, the invention provides a recombinant non-human animal containing a transgene comprising a nucleic acid sequence encoding a chimeric protein comprising a fragment of CDK2 of at least 6 amino acids fused via a covalent bond to a fragment of a CDK2-IP protein of at least 6 amino acids.

In another specific embodiment, the invention provides transgenic animals that have incorporated and over express or misexpress mRNA encoding hsReq*-1 or hsReq*-2, which mRNA does not require splicing (i.e., the transgene encodes the mature form of the hsReq*-1 or hsReq*-2 RNA) and, therefore, does not encode hsReq, i.e., have incorporated a nucleic acid coding for hsReq*-1 or hsReq*-2 mRNA in which the transcription of this mRNA is under the control of either the hsReq promoter or a heterologous promoter.

6. EXAMPLES

6.1 Identification of CDK2:CDK2-IP Complexes

A modified, improved yeast two hybrid system was used to identify protein interactions. Yeast is a eukaryote, and therefore any intermolecular protein interactions detected in this type of system would be expected to demonstrate protein interactions that occur under physiological conditions (Chien et al., 1991, Proc. Natl. Acad. Sci. USA 88: 9578–9581.) Expression vectors were constructed to encode two hybrid proteins. For a "forward" screen, one hybrid consisted of the DNA binding domain of the yeast transcriptional activator Gal4 fused to a portion of CDK2. The other hybrid consisted of the Gal4 activator domain fused to "prey" protein sequences encoded by a mammalian cDNA library. Each of the vectors was then inserted into complementary (a and alpha) mating types of yeast using methods known in the art (Chien et al.,1991, supra). Mating was carried out to express both vector constructs within the same yeast cells, thus allowing interaction to occur. Interaction between the bait and prey domains led to transcriptional activation of reporter genes containing cis-binding elements for Gal4. The reporter genes encoding the indicator protein beta-galactosidase, and metabolic markers for uracil and histidine auxotrophy, were included in specific fashion in one or the other of the yeast strains used in the mating. In this way, yeast were selected for successful mating, expression of both fusion constructs, and expression of CDK2-IPs. Yeast clones that contained interacting regions were picked and grown in individual wells of microtiter plates. The plasmids containing the CDK2-IP sequences were then isolated and characterized.

The prey cDNAs were obtained from a commercial fetal brain cDNA library of $3.5 \times 10^6$ independent isolates (Clontech #HL4029AH, Palo Alto, Calif.). The library was synthesized from Xho 1-dT15 primed fetal brain mRNA (from five male/female 19–22 week fetuses) that was directionally cloned into pACT2, a yeast Gal4 activation domain cloning vector including the LEU2 gene for selection in yeast deficient in leucine biosynthesis.

A forward screen was used to test the interaction of prey cDNA products against an array of 18 bait proteins, one of which was encoded by the CDK2 nucleotide sequence of nucleotides 1–897 as depicted in FIG. 1 (SEQ ID NO:1), encoding the entire amino acids sequence from residues 1–298 of the CDK2 protein, as depicted in FIG. 1 (SEQ ID NO:2). The bait fragment was amplified from the Clontech pACT2 library by PCR using the forward primer 5'GATG-CAGAATTCCGACATGACTCAG3' (SEQ ID NO:14) and the reverse primer 5'ATGGTGGGCGGTGTTGTCAT-AGCG3' (SEQ ID NO:15) by standard techniques. The fragment was cloned into the SfiI site of the vector pASSfiI, constructed by introducing an SfiI-containing polylinker into the vector pAS2-1 (Clontech). This vector is a yeast DNA-binding domain cloning vector that contains the TRP1 gene for selection in yeast strains deficient in tryptophan biosynthesis. The bait sequence was confirmed by nucleic acid sequencing to confirm that PCR amplification reproduced an accurate copy of the CDK2 sequence. This test determined that as predicted, the bait sequence encoded an interacting domain identical to human CDK2.

The nucleic acid encoding the introduced bait was expressed by lithium acetate/polyethylene glycol transformation (Ito et al., 1983, J. Bacteriol. 153:163–168) into the yeast strain YULH (mating type a, ura3, his3, lys2, Ade2, trp1, leu2, gal4, gal80, GAL1-URA3, GAL1-lacZ), while the prey sequences were introduced by transformation into the yeast strain N106r (mating type α, ura3, his3, ade2, trp1, leu2, gal4, gal80, cyh$^r$, Lys2: :GAL1$_{UAS}$-HIS3$_{TATA}$-HIS3, ura3::GAL1$_{UAS}$-GAL$_{TATA}$-laCZ). The two transformed populations were then mated using standard methods in the art (Sherman et al., eds., 1991, Getting Started with Yeast, Vol. 194, Academic Press, New York). Briefly, cells were grown until mid-to-late log phase on media that selected for the presence of the appropriate plasmids. The two mating strains, alpha and a, were then diluted in YAPD media (Sherman et al., eds., 1991, Getting Started with Yeast, Vol. 194, Academic Press, New York), filtered onto nitrocellulose membranes, and incubated at 30 degrees Celsius for 6–8 hours. The cells were then transferred to media selective for the desired diploids, i.e., yeast harboring reporter genes for beta-galactosidase, uracil auxotrophy, and histidine auxotrophy, and expression of the vectors encoding the bait and prey. The mating products were plated on SC (synthetic complete) media (Kaiser, Michaelis and Mitchell, Eds, 1994, Methods in Yeast Genetics, 1994 Ed., Cold Spring Harbor Laboratory Press, New York, p.209) lacking adenine and lysine (to select for successful mating), leucine and tryptophan (to select for expression of genes encoded by both the bait and prey plasmids), and uracil and histidine (to select for protein interactions). This medium is herein referred to as SCS medium, for SC Selective medium.

Selected clones were tested for expression of β-galactosidase to confirm the formation of a CDK2:CDK2-IP interaction. Filter-lift β-galactosidase assays were performed as modified from the protocol of Breeden and Nasmyth (1985, Cold Spring Harbor Quant. Biol. 50: 643–650). Colonies were patched onto SCS plates, grown overnight, and replica plated onto Whatman No. 1 filters. The filters were then assayed for β-galactosidase activity. Colonies that were positive turned a visible blue.

Cells in colonies positive for protein interaction contained a mixture of DNA-binding and activation-domain plasmids. These cells were individually plated, and regrown as single isolates in individual wells of 96-well plates. Ten microliters of each isolate was lysed, the inserts within the pACT2 and pASSfiI plasmids were amplified by polymerase chain reaction using primers specific for the flanking sequences of each vector, and approximately 200 amino-terminal bases of each insert was determined using an ABI 377 sequenator. Comparison to known sequences was made using the "BLAST" program publicly available through the National Center for Biotechnology Information. Ten unique isolates were identified, identical to the known cyclin H nucleic acid sequence, starting at nucleotides 64, 76, 82, 94, 97, 100, 103, 163, 166, and 379 (as depicted in FIG. 2 (SEQ ID NO:3)). Others identified sequences included one isolate identical to the cyclin I sequence starting at nucleotide 46 (as depicted in FIG. 3 (SEQ ID NO:5)), one isolate identical to the ERH sequence starting from nucleotide 153 (as depicted in FIG. 4 (SEQ ID NO:7)), and two isolates identical to the hsReq sequence starting from nucleotides 1789 and 1819 (as depicted in FIG. 5 (SEQ ID NO:9)). The determined nucleic acid sequences and corresponding amino acid sequences of cyclin H, cyclin I, ERH, and splice variants hsReq*-1 and hsReq*-2 are shown in FIGS. 2–4, 6, and 7, respectively. A summary of the CDK2 and CDK2-IP interacting domains is shown in FIG. 8.

6.2 Verification of the Specificity of the CDK2:Cyclin H, CDK2:Cyclin I, CDK2:ERH, CDK2:hsReq*-1 and CDK2:hsReq*-2 Interactions To test for the specificity of bait:prey interaction, two general tests were first performed. In the first instance, N106r yeast cells were created that express the individual plasmids encoding CDK2, cyclin H, cyclin I, ERH, and the sequences encoding hsReq*-1 and/or hsReq*-2. These yeast cells were plated on SCS plates, grown overnight, and examined for growth. No growth was found for all five proteins, confirming that they were not "self-activating" proteins, that is, these proteins require interaction with a second protein domain for a functional activation complex.

In the second instance, plasmids containing cyclin H, cyclin I, ERH, or hsReq*-1 and hsReq*-2 inserts were transformed into strain N106r (mating type alpha) and mated with yeast strain YULH (mating type a) expressing proteins other than CDK2. Promiscuous binders, that is, inserts able to bind with many other proteins in a non-specific fashion, would interact non-specifically with non-CDK2 domains, and would be discarded as non-specific interactants. None of the interactants showed binding to protein other than those described in the next paragraph.

To recapitulate the detected interactions, and further demonstrate their specificity, the isolated bait plasmid for CDK2, along with the plasmid encoding human bait protein 1 (B1) were used to transform yeast strain YULH (mating type a). The interacting domains from cyclin H, ERH, p27, human prey protein 1 (P1), p21 and hsReq were transformed into strain N106r (mating type alpha). The transformants were reamplified, and a mating performed to recapitulate the identified CDK2:CDK2-IP interactions. As shown in FIG. 9, CDK2 complexed specifically with cyclin H (Box A), ERH (Box B), and hsReq*-1 and/or hsReq*-2 (Box E), as well as the known interactants p27 (Box C) and p21 (Box D). It did not react non-specifically with the prey P1. As illustrated in FIG. 9, the intersection of the CDK2 row (top) with the cyclin H, ERH, p21, p27, and hsReq*-1 and/or hsReq*-2 columns indicates growth (i.e. a positive interaction), but the intersection of the CDK2 row with the column for P1 indicates no growth, i.e., no protein interaction. Mating of B1 with P1 (Box F) indicates confirmed an interaction previously found in our studies (unpublished) and demonstrates that P1 is capable of forming functional interactions.

6.3 Assembly of the Sequences Encoding hsReq*-1 and hsReq*-2

Regions within the 3' untranslated regions of the known protein cDNAs for hsReq were identified as encoding a protein or proteins that interact with CDK2 using the modified yeast two hybrid system (as described in Section 6.1 supra). The present inventors identified interacting nucleic acid sequences identical to the nucleotide sequence of hsReq from nucleotide base 1788 to the end and from 1818 to the end (as depicted in FIG. 5 (SEQ ID NO:9)).

These regions did not encode open reading frames (ORFS) sufficient to encode a protein. This was determined by performing a "BLAST" analysis to determine translations in the three possible forward reading frames. Within the detected regions, no ORF of 60 amino acids or greater, beginning with an initiator methionine, and no ORF beginning from the 5' end that could represent the C-terminus of a protein of 60 amino acids or longer, was detected for any of the three detected inserts. Thus, the sequences were examined to determine if they could encode splice variants of the known hsReq protein that included the detected interacting sequences.

Determination of 5' and 3' splice points for protein splice variants was performed as follows: First, potential 5' splice sites were identified in the coding sequence of the known protein. The sequence must contain an invariant GT sequence at the start of the intron. The remaining bases of the consensus splice site are not invariant, but the preferred consensus sequence is AG:GTAAGT, with the colon indicating the splice point (Padgett et al., 1984, Ann. Rev. Biochem. 55:1119–1150). Potential splice sites were identified in order of their matching to this consensus, with a minimum of 4/6 matches required the bases other than the invariant GT (which must be matched).

Next, potential 3' intron:exon splice sites were identified based on the consensus analysis described by Padgett et al., 1984 (Ann. Rev. Biochem. 55:1119–1150). The sequence between potential 5' splice sites and the start of the detected interacting sequence was scanned for the invariant AG: sequence. The base preceding (i.e., 5' of) the AG sequence must be a C or T. Then, the 5 to 14 bases 5' to the last intronic G base were required to contain at most two non-T and non-C bases (Padgett et al., 1984, Ann. Rev. Biochem. 55:1119–1150).

Next, based on the known translational frame of the mature hsReq protein and each predicted 5' splice site, compatible translational frames for successful splicing were defined for potential 3' splice sites. Nucleic acid sequences were analyzed by ORF Finder in NCBI Blast Package (NCBI, Bethesda, Md.) to define possible protein translation products. Translation in the three forward translation frames was used to define possible open reading frames (contiguous spans of codons for amino acids without the presence of a stop codon). Only 3' sites that matched the necessary translational frame of a 5' prime splice junction were retained. Unmatched 5' or 3' splice sites were eliminated. In this case, where no ideal 3' splice site match was found based on the above analysis, which was true for the hsReq sequence, and thus, sites containing three non-C, non-T bases upstream of the splice site were included, resulting in two possible 3' splice sites for hsReq (for the splice variants hsReq*-1 and hsReq*-2, respectively).

Finally, for each possible 5':3' splice site pair, a search for a mammalian branch point consensus sequence was performed (Reed and Maniatis, 1988, Genes Dev. 2:1268–1276). This sequence (T/C N CTGAC) was selected if matches were found for 5 of the 6 defined bases, and if the consensus sequence were present in the requisite 20–60 bases 5' to the 3' splice site. Although not absolutely required for pre mRNA splicing, the efficiency of splicing is related to the presence of the consensus sequence. Thus, 5':3' splice site pairs with a branch point consensus sequence were retained over splice site pairs that did not have a branch point consensus sequence. Each splice variant for hsReq, i.e., hsReq*-1 and hsReq*-2, had a branch point consensus sequence (FIG. 5).

Final requirements were that splice variant proteins must encode at least 60 amino acid residues to constitute a viable in vivo product. Further, the 3' end of the splice variants must, by definition, extend into the identified interacting sequence. The splice sites for the splice variants hsReq*-1 and hsReq*-2 met these requirements. Specifically, for both hsReq*-1 and hsReq*-2, a 5' splice site was identified at nucleotides 563–570 of the hsreq sequence as depicted in FIG. 5 (SEQ ID NO:9), with this 5' splice site indicated as B in FIG. 5. For hsReq*-1, a 3' splice site was identified at nucleotides 1566 to 1580 and the branch point consensus sequence at nucleotides 1553 to 1544 of the hsReq nucleotide sequence (as depicted in FIG. 5) indicated in FIG. 5 as "E" and "D", respectively. For hsReq*-2, an alternative 3' splice site was identified at nucleotides 1776 to 1790 and the related branch point consensus sequence at nucleotides 1759–1765 of the hsReq nucleotide sequence (as depicted in FIG. 5 (SEQ ID NO:9)), indicated in FIG. 5 as "G" and "IF", respectively.

Splice variant sequences were subjected to a further searches of the NRDB, a non-redundant compilation of GenBank CDS translations+PDB+SwissProt+PIR SwissProt sequences, and "month", which includes all new or revised GenBank CDS translation+PDB+SwissProt+PIR sequences released in the last 30 days, to detect homologies to known protein sequences that were not detected over the span of the known protein sequences. No significant homologies to known proteins were detected for hsReq*-1 and hsReq*-2 utilizing this analysis.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A purified protein selelcted from the group consisting of human hsReq*-1 and hdReq*-2 proteins, wherein the protein binds CDK2 protein.

2. The protein of claim 1, which comprises an amino acid sequence selected from the group consisting of: SEQ ID NO:11 and SEQ ID NO:13.

3. A purified derivative or analog of the protein of claim 1, which derivative or analog can bind CDK2, which derivative or analog possesses at least a 95% identify to the protein of claim 1 and which comprises at least a 10 amino acid portion of amino acids 187–280 of SEQ ID NO:11 or of amino acids 188–210 of SEQ ID NO:13.

4. The derivative or analog of claim 3, which binds an antibody specific of a protein selected from the group consisting of: hdReq*-1 and hsReq*-2 proteins, which antibody does not bind hsReq.

5. A purified fragment of the protein of claim 1, which fragment comprises an at least 6 amino acid portion of said protein, the sequence of which portion is not contained in hsReq.

6. A purified protein comprising an amino acid sequence which possesses at least a 95% identify to the protein of claim 1, wherein the percentage of identify is determined over an amino acid sequence of identical size to said protein of claim 1, and which protein is not hsReq, and which protein can bind CDK2 protein.

7. A chimeric protein comprising a fragment of the protein of claim 1, said fragment consisting of at least 6 amino acids and said fragment not being identical to a fragment of hsReq, fused via a covalent bond to an amino acid sequence of a second protein, in which the second protein is not said protein of claim 1 and is not hsReq.

8. A composition comprising a protein of claim 1 and a pharmaceutically-acceptable carrier.

9. A composition comprising a protein of claim 2 and a pharmaceutically acceptable carrier.

10. A purified protein encoded by a nucleic acid hydrizable to the inverse complement of DNA having a nucleotide sequence consisting of a portion of the nucleotide sequence of SEQ ID NO:12, said portion containing the 5'splice site at nucleotides 563–570 of SEQ ID NO:9, the 3' splice site at nucleotides 1776–1790 of SEQ ID NO: 9 and the branch point consensus sequence at nucleotides 1759–1765 of SEQ ID NO:9, said nucleic acid comprising a sequence absolutely complementary to an at least 10 nucleotide sequence spanning said splice sites, wherein the protein binds CDK2 protein.

11. A purified protein encoded by a nucleic acid hybridizable to the inverse complement of DNA having a nucleotide sequence consisting of a portion of the nucleotide sequence of SEQ ID NO:10, said portion containing a 5' splice site a nucleotides 563–570 of SEQ ID NO:9, a 3' splice a nucleotides 1556–1580 of SEQ ID NO: 9 and a branch point consensus sequence at nucleotides 1553–1544 SEQ ID NO:9, said nuclei acid comprising a sequence absolutely complementary to an at least 10 nucleotide sequence spanning said splice sites, wherein the protein binds CDK2 protein.

12. A method to detected the presence of CDK2 in a sample, the method comprising:

a) providing the sample;
   b) contacting the sample with hsReq*1 or hsReq*2 in order to allow for the formation of an hsReq*1:CDK2 or hsReq*2:CDK2 complex; and
   c) detecting the presence or absence of the complex.

13. The method of claim 12, wherein the presence of the hsReq*1:CDK2 or hsReq*2:CDK2 complex is determined by immunoassay.

14. The method of claim 13, wherein the immunoassay further comprises contacting the sample with an antibody that binds immunospcecifically to the hsReq*1:CDK2 or hsReq*2:CDK2 complex, thereby determining the presence of the complex in the sample.

* * * * *

UNITED STATES PATENT AND TRADEMARK OFFICE
CERTIFICATE OF CORRECTION

PATENT NO.    : 6,521,412 B1
DATED         : February 18, 2003
INVENTOR(S)   : Meijia Yang, Krishnan Nandabalan and Vincent Peter Schulz It is certified that error appears in the above-identified patent and that said Letters Patent is hereby corrected as shown below:

Column 101,
Lines 23 and 36, after "95%", delete "identify", and insert -- identity --.
Line 28, after "specific", delete "of", and insert -- for --.
Line 28, after "of:", delete "hdReq*-1", and insert -- hsReq*1 --.
Line 37, after "of", delete "identify", and insert -- identity --.

Column 102,
Line 28, after "site", delete "a", and insert -- at --.
Line 29, after "splice", delete "a", and insert -- at --.
Line 30, after "nucleotides", delete "1556", and insert -- 1566 --.
Line 48, after "binds", delete "immunospcecifically", and insert -- immunospecifically --.

Signed and Sealed this

Twenty-second Day of July, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,521,412 B1
DATED        : February 18, 2003
INVENTOR(S)  : Meijia Yang, Krishnan Nandabalan and Vincent Peter Schulz It is certified that error appears in the above-identified patent and that said Letters Patent is hereby corrected as shown below:

Column 101,
Lines 23 and 36, after "95%", delete "identify", and insert -- identity --.
Line 28, after "specific", delete "of", and insert -- for --.
Line 29, after "of:", delete "hdReq*-1", and insert -- hsReq*1 --.
Line 37, after "of", delete "identify", and insert -- identity --.

Column 102,
Line 28, after "site", delete "a", and insert -- at --.
Line 29, after "splice", delete "a", and insert -- at --.
Line 29, after "nucleotides", delete "1556", and insert -- 1566 --.
Line 48, after "binds", delete "immunospcecifically", and insert -- immunospecifically --.

This certificate supersedes Certificate of Correction issued July 22, 2003.

Signed and Sealed this

Eighteenth Day of November, 2003

JAMES E. ROGAN
*Director of the United States Patent and Trademark Office*